US009909095B2

(12) United States Patent
Cimino et al.

(10) Patent No.: US 9,909,095 B2
(45) Date of Patent: *Mar. 6, 2018

(54) TISSUE PROCESSING APPARATUS WITH FILTER PIERCEABLE TO REMOVE PRODUCT AND METHOD FOR PROCESSING ADIPOSE TISSUE

(71) Applicant: The GID Group, Inc., Louisville, CO (US)

(72) Inventors: William W. Cimino, Louisville, CO (US); Adam J. Katz, Gainesville, FL (US); Ramon Llull, Palma de Mallorca (ES)

(73) Assignee: The GID Group, Inc., Louisville, CO (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/839,650

(22) Filed: Aug. 28, 2015

(65) Prior Publication Data

US 2015/0368603 A1 Dec. 24, 2015

Related U.S. Application Data

(63) Continuation of application No. 14/370,694, filed as application No. PCT/US2013/021156 on Jan. 11, (Continued)

(51) Int. Cl.
*C12M 1/26* (2006.01)
*A61L 27/36* (2006.01)
(Continued)

(52) U.S. Cl.
CPC ........... *C12M 33/04* (2013.01); *A61L 27/227* (2013.01); *A61L 27/3683* (2013.01);
(Continued)

(58) Field of Classification Search
CPC .............................. C12M 27/02; C12M 33/04
(Continued)

(56) References Cited

U.S. PATENT DOCUMENTS 3,854,704 A 12/1974 Balas
4,438,032 A 3/1984 Golde et al.
(Continued)

FOREIGN PATENT DOCUMENTS

EP 0512769 A2 11/1992
JP 2009189282 A 8/2009
(Continued)

*Primary Examiner* — Tatyana Zalukaeva
*Assistant Examiner* — Kai Weng
(74) *Attorney, Agent, or Firm* — Marsh Fischmann & Breyfogle LLP

(57) ABSTRACT

A portable apparatus for collection and processing of human biological material, such as containing adipose extracted during a lipoplasty procedure, is useful for multi-step processing to prepare a concentrated product (e.g., stromal vascular fraction). The apparatus has a container with a containment volume with a tissue retention volume and a filtrate volume separated by a filter and with a tapered portion to a collection volume for collecting concentrate product. Inlet and suction ports provide access to the tissue retention volume and filtrate volume, respectively, and an extraction port provides versatile access for removal of target processed concentrate material. Advancing a hollow member such as a hypodermic needle through the extraction port and into the collection volume pierces the filter with the hollow member, providing a safety feature to prevent reuse of the apparatus. Access ports may be configured for access only from above the container. A method of processing adipose tissue to concentrate stromal vascular cells includes multi-step processing using a portable container.

30 Claims, 29 Drawing Sheets

Related U.S. Application Data 2013, now Pat. No. 9,206,387, and application No. 14/370,694, which is a continuation-in-part of application No. 13/808,550, filed as application No. PCT/US2011/043451 on Jul. 8, 2011, now Pat. No. 9,260,697.

(60) Provisional application No. 61/585,566, filed on Jan. 11, 2012, provisional application No. 61/363,150, filed on Jul. 9, 2010.

(51) Int. Cl.
  *B01D 29/64* (2006.01)
  *A61L 27/38* (2006.01)
  *A61L 27/22* (2006.01)
  *C12M 1/00* (2006.01)

(52) U.S. Cl.
  CPC ...... *A61L 27/3834* (2013.01); *B01D 29/6476* (2013.01); *C12M 33/14* (2013.01); *C12M 47/00* (2013.01); *C12M 47/04* (2013.01)

(58) Field of Classification Search
  USPC .......................................................... 604/406
  See application file for complete search history.

(56) References Cited

U.S. PATENT DOCUMENTS

| | | |
|---|---|---|
| 4,820,626 A | 4/1989 | Williams et al. |
| 5,035,708 A | 7/1991 | Alchas et al. |
| 5,226,914 A | 7/1993 | Caplan et al. |
| 5,330,914 A | 7/1994 | Uhlen et al. |
| 5,336,616 A | 8/1994 | Livesey et al. |
| 5,372,945 A | 12/1994 | Alchas et al. |
| 5,409,833 A | 4/1995 | Hu et al. |
| 5,486,359 A | 1/1996 | Caplan et al. |
| 5,586,732 A | 12/1996 | Yamauchi et al. |
| 5,591,625 A | 1/1997 | Gerson et al. |
| 5,610,074 A | 3/1997 | Beritashvili et al. |
| 5,624,840 A | 4/1997 | Naughton et al. |
| 5,688,531 A | 11/1997 | Benayahu et al. |
| 5,728,739 A | 3/1998 | Ailhaud et al. |
| 5,736,396 A | 4/1998 | Bruder et al. |
| 5,786,207 A | 7/1998 | Katz et al. |
| 5,811,094 A | 9/1998 | Caplan et al. |
| 5,817,050 A | 10/1998 | Klein |
| 5,827,735 A | 10/1998 | Young et al. |
| 5,827,740 A | 10/1998 | Pittenger |
| 5,827,897 A | 10/1998 | Ailhaud et al. |
| 5,854,292 A | 12/1998 | Ailhaud et al. |
| 5,906,934 A | 5/1999 | Grande et al. |
| 5,908,784 A | 6/1999 | Johnstone et al. |
| 5,937,863 A | 8/1999 | Knowlton |
| 5,968,356 A | 10/1999 | Morsiani et al. |
| 6,200,606 B1 | 3/2001 | Peterson et al. |
| 6,261,549 B1 | 7/2001 | Fernandez et al. |
| 6,316,247 B1 | 11/2001 | Katz et al. |
| 6,391,297 B1 | 5/2002 | Halvorsen |
| 6,429,013 B1 | 8/2002 | Halvorsen et al. |
| 6,478,966 B2 | 11/2002 | Zhou et al. |
| 6,544,788 B2 | 4/2003 | Singh |
| 6,555,374 B1 | 4/2003 | Gimble et al. |
| 6,777,231 B1 | 8/2004 | Katz et al. |
| 6,841,150 B2 | 1/2005 | Halvorsen et al. |
| 6,852,533 B1 | 2/2005 | Rafii et al. |
| 7,001,746 B1 | 2/2006 | Halvorsen et al. |
| 7,033,587 B2 | 4/2006 | Halvorsen et al. |
| 7,078,230 B2 | 7/2006 | Wilkison et al. |
| 7,078,232 B2 | 7/2006 | Konkle et al. |
| 7,179,649 B2 | 2/2007 | Halvorsen |
| 7,266,457 B1 | 9/2007 | Hickman |
| 7,294,334 B1 | 11/2007 | Michal et al. |
| 7,361,368 B2 | 4/2008 | Claude et al. |
| 7,390,484 B2 | 6/2008 | Fraser et al. |
| 7,429,488 B2 | 9/2008 | Fraser et al. |
| 7,470,537 B2 | 12/2008 | Hedrick et al. |
| 7,473,420 B2 | 1/2009 | Fraser et al. |
| 7,501,115 B2 | 3/2009 | Fraser et al. |
| 7,514,075 B2 | 4/2009 | Hedrick et al. |
| 7,531,355 B2 | 5/2009 | Rodriguez et al. |
| 7,572,236 B2 | 8/2009 | Quick et al. |
| 7,582,292 B2 | 9/2009 | Wilkison et al. |
| 7,585,670 B2 | 9/2009 | Hedrick et al. |
| 7,595,043 B2 | 9/2009 | Hedrick et al. |
| 7,622,108 B2 | 11/2009 | Collins et al. |
| 7,641,643 B2 | 1/2010 | Michal et al. |
| 7,651,684 B2 | 1/2010 | Hedrick et al. |
| 7,659,118 B2 | 2/2010 | Furcht et al. |
| 7,670,596 B2 | 3/2010 | Collins et al. |
| 7,687,059 B2 | 3/2010 | Fraser et al. |
| 7,708,152 B2 | 5/2010 | Dorian et al. |
| 7,727,763 B2 | 6/2010 | McKenna, Jr. et al. |
| 7,732,190 B2 | 6/2010 | Michal et al. |
| 7,744,869 B2 | 6/2010 | Simon |
| 7,749,741 B2 | 7/2010 | Bullen et al. |
| 7,771,716 B2 | 8/2010 | Hedrick et al. |
| 7,780,649 B2 | 8/2010 | Shippert |
| 7,780,860 B2 | 8/2010 | Higgins et al. |
| 7,789,872 B2 | 9/2010 | Shippert |
| 7,794,449 B2 | 9/2010 | Shippert |
| 7,887,795 B2 | 2/2011 | Fraser et al. |
| 7,901,672 B2 | 3/2011 | Fraser et al. |
| 9,206,387 B2 | 12/2015 | Llull et al. |
| 9,260,697 B2 | 2/2016 | Cimino et al. |
| 9,296,984 B2 | 3/2016 | Cimino et al. |
| 2001/0030152 A1 | 10/2001 | Wright et al. |
| 2001/0033834 A1 | 10/2001 | Wilkison et al. |
| 2002/0076400 A1 | 6/2002 | Katz et al. |
| 2002/0119126 A1 | 8/2002 | Halvorsen |
| 2003/0082152 A1 | 5/2003 | Hedrick et al. |
| 2003/0161817 A1 | 8/2003 | Young et al. |
| 2003/0211602 A1 | 11/2003 | Atala |
| 2004/0067218 A1 | 4/2004 | Casteilla et al. |
| 2004/0097867 A1 | 5/2004 | Fraser et al. |
| 2004/0171146 A1 | 9/2004 | Katz et al. |
| 2005/0048034 A1 | 3/2005 | Fraser et al. |
| 2005/0076396 A1 | 4/2005 | Katz et al. |
| 2005/0153442 A1 | 7/2005 | Katz et al. |
| 2005/0282275 A1 | 12/2005 | Katz et al. |
| 2006/0051865 A1 | 3/2006 | Higgins et al. |
| 2007/0225665 A1 | 9/2007 | Perez-Cruet et al. |
| 2008/0014181 A1 | 1/2008 | Ariff et al. |
| 2008/0050275 A1 | 2/2008 | Bischof et al. |
| 2008/0319417 A1 | 12/2008 | Quijano et al. |
| 2009/0042267 A1 | 2/2009 | Park |
| 2010/0055087 A1 | 3/2010 | Higgins et al. |
| 2010/0285521 A1 | 11/2010 | Vossman et al. |
| 2010/0285588 A1 | 11/2010 | Stubbers et al. |
| 2011/0117650 A1 | 5/2011 | Riordan |
| 2012/0003733 A1 | 1/2012 | Gueneron |
| 2012/0214659 A1 | 8/2012 | Do et al. |

FOREIGN PATENT DOCUMENTS

| | | |
|---|---|---|
| JP | 2011125813 A | 6/2011 |
| JP | 2013-507983 A | 3/2013 |
| WO | 2011052946 A2 | 5/2011 |
| WO | 2012006587 A2 | 1/2012 |
| WO | 2013106655 A1 | 7/2013 |

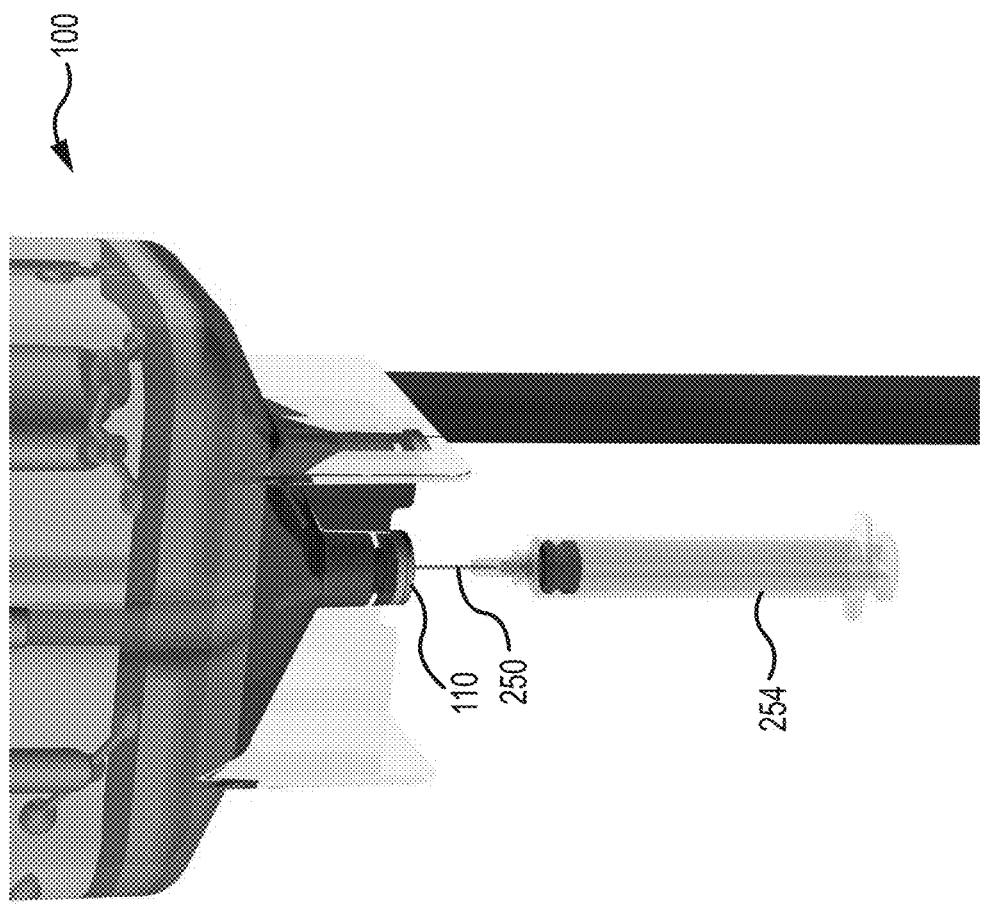
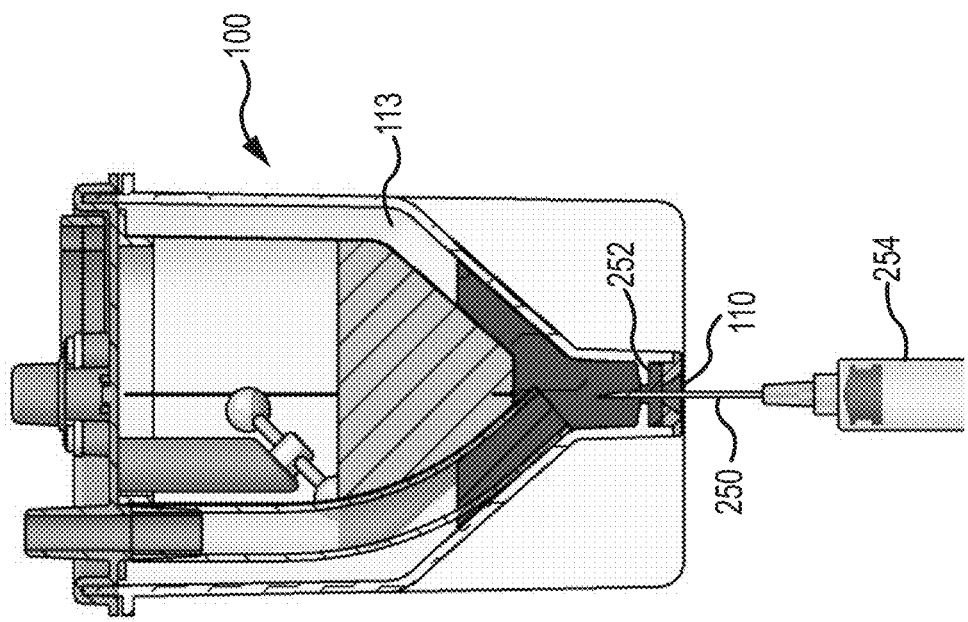
FIG. 6

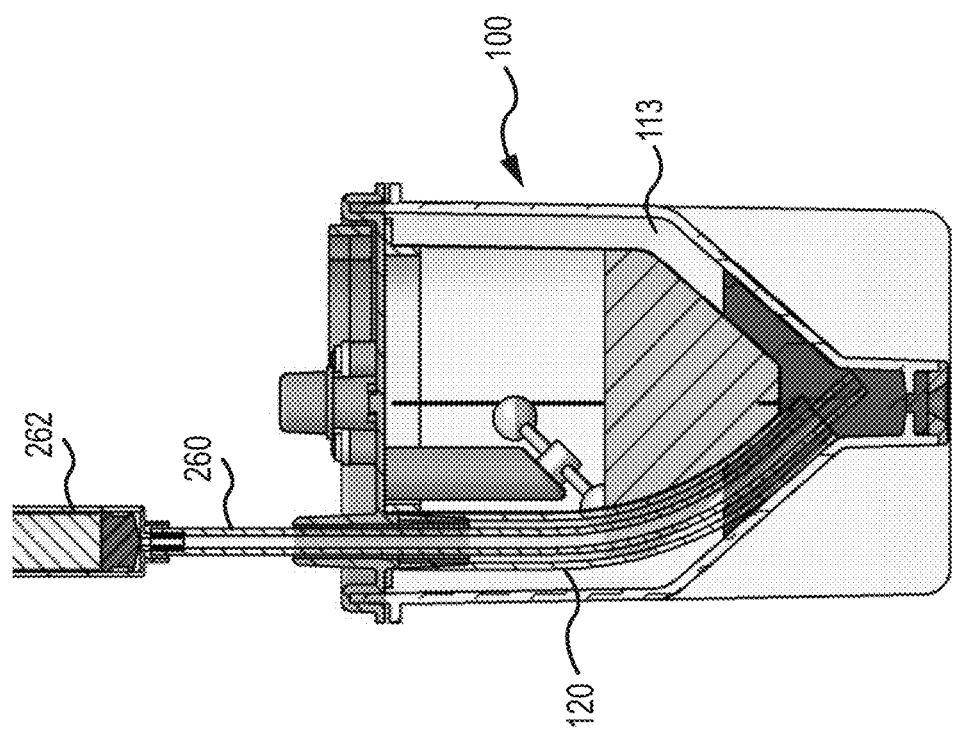
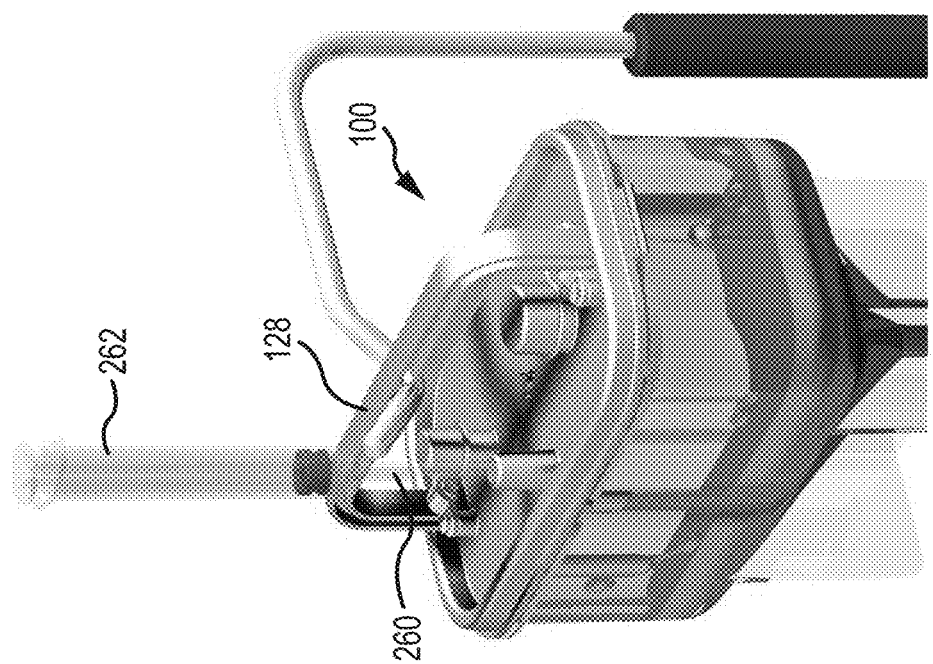
FIG. 7

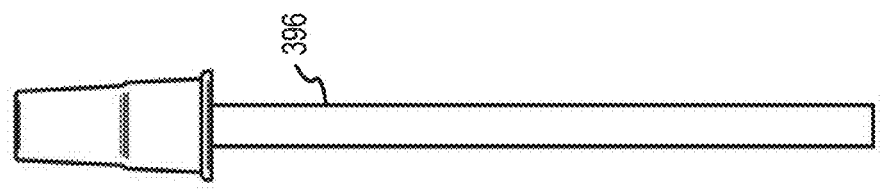
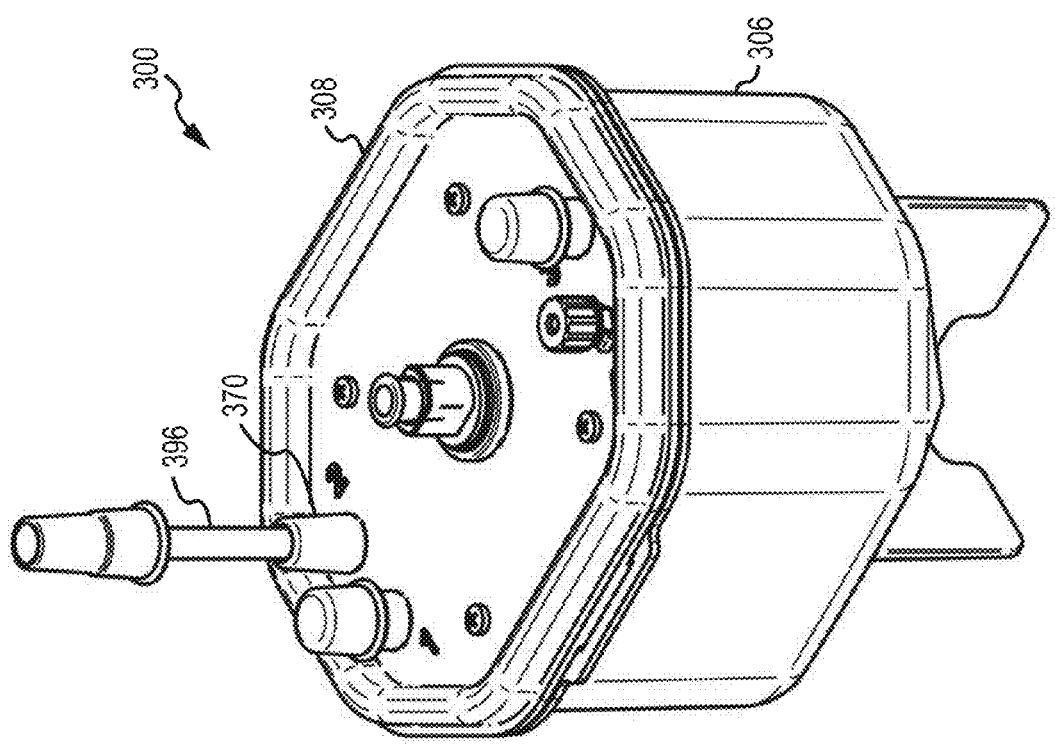

TISSUE PROCESSING APPARATUS WITH FILTER PIERCEABLE TO REMOVE PRODUCT AND METHOD FOR PROCESSING ADIPOSE TISSUE

CROSS REFERENCE TO RELATED APPLICATIONS

This patent application is a continuation of U.S. patent application Ser. No. 14/370,694 which is a national stage of International Patent Application No. PCT/US2013/021156 filed Jan. 11, 2013 and which claims a benefit of U.S. Provisional Patent Application No. 61/585,566 filed Jan. 11, 2012; and which U.S. patent application Ser. No. 14/370,694 is a continuation-in-part of U.S. patent application Ser. No. 13/808,550, which is a national stage of International Patent Application No. PCT/US2011/043451 filed Jul. 8, 2011 and which claims a benefit of U.S. Provisional Patent Application No. 61/363,150 filed Jul. 9, 2010. This application is a continuation-in-part of U.S. patent application Ser. No. 13/808,550, which is a national stage of International Patent Application No. PCT/US2011/043451 filed Jul. 8, 2011 and which claims a benefit of U.S. Provisional Patent Application No. 61/363,150 filed Jul. 9, 2010. The entire contents, and each and every portion of such contents, of each and every one of the patent applications identified herein (including U.S. patent application Ser. No. 14/370,694; International Patent Application No. PCT/US2013/021156; U.S. Provisional Patent Application No. 61/585,566; U.S. patent application Ser. No. 13/808,550; International Patent Application No. PCT/US2011/043451; and U.S. Provisional Patent Application No. 61/363,150) are hereby incorporated herein by reference for all purposes.

FIELD OF THE INVENTION

The invention relates to methods for processing human biological material comprising adipose tissue, for example to prepare a concentrate with leuko stromal vascular cells, which include stem cells, and apparatus for processing human biological material, which may or may not include adipose tissue.

BACKGROUND OF THE INVENTION

Adipose tissue is recognized as a promising source of stem cells with at least multi-potent differentiation potential. Lipoasperate obtained during a lipoplasty procedure, such as lipo surgery, may be processed to prepare a so-called stromal vascular fraction (SVF) that is rich in leuko stromal vascular cells, which include stem cells. Processing to prepare SVF may include washing lipoasperate with saline solution, followed by enzymatic digestion of washed tissue using collagenase, and centrifuging digested material to prepare SVF in the form of a centrifuged pellet. Such collection and processing of tissue involves several steps with transfer of contents between different process containers for different tissue collection and processing steps, which is cumbersome and provides significant opportunities for error or contamination.

Some attempts have been made to design portable containers in which lipoasperate may be collected and then processed within the container to digest tissue and prepare a concentrate enriched in leuko stromal vascular cells. Potential benefits of using such portable containers include a reduced need to transfer material between containers to perform different process steps and a reduction in the need for multiple, specially-designed processing containers. However, such multi-step processing in portable containers faces significant equipment and process design and operating limitations, especially when attempting to process relatively large volumes of adipose tissue at one time. Desired leuko vascular cells, including stem cells, are sensitive to processing conditions and viability of recovered cells may suffer significantly if processing is not adequately controlled. Also, recovery of cells from the container is of critical importance. Significant potential exists for loss of valuable cells to recovery from the container, such as by cells adhering to internal equipment and surfaces within the container. One problem with multi-step processing in a single portable container is that the container design and processing operations must accommodate the different requirements of each of the different process steps to be performed in the single container, and with severe volume constraints in relation to a practical size for such a portable container. In contrast, processing systems that involve transfer of contents between multiple different containers for performance of different process steps benefit from an ability to optimize equipment and process design for each process container that is dedicated to performance of a single step of an overall process. Therefore, multi-container processing has significant advantages in terms of step-by-step equipment and process optimization. Moreover, a multi-container design is better suited for automation, for example with automated transfer of processed material through conduits between different process containers or with automated control of process parameters for uniformity and process control. Multi-container processing remains the predominant processing technique at this time for processing adipose tissue to prepare stromal vascular fraction concentrates.

SUMMARY OF THE INVENTION

The invention involves a portable apparatus adapted for multi-step processing of human biological material. The human biological material may or may not comprise adipose tissue. The invention also involves a method for multi-step processing of adipose tissue in a portable container to prepare a concentrate product rich in leuko stromal vascular cells, or stromal vascular fraction cells. A first aspect of the invention is provided by an apparatus that is adapted to serve both for collection of human biological material (e.g., tissue, biological fluids) and for convenient multi-step post-collection processing of collected material. Such human biological material and separated or processed portions thereof may be referred to herein simply as "tissue", for convenience and brevity. For example, the term tissue may be used herein to refer to in-tact tissue, disrupted tissue, tissue fragments and biological fluids associated with or separate from tissue. The apparatus is orientable in a collection orientation (also referred to as an access orientation) for collection of human biological material, or tissue, for example which may comprise adipose tissue collected during a lipoplasty procedure. The collection orientation is also referred to herein as the access orientation, and the terms are used interchangeably. For convenience of description except as noted, the apparatus is described as oriented in the collection orientation. As such, relational references such as to top, bottom, up, down, above, below, elevations, vertical, horizontal and the like are in relation to the apparatus as oriented in the collection orientation. The apparatus may be configured such that the apparatus may be stably supported in the collection orientation. For example, the apparatus may have a base configured for interfacing with a flat, substantially horizontal surface (e.g., counter top or table top) to stably support the apparatus in the collection orientation, or may be held in a mounting structure that maintains the apparatus in the collection orientation. Although such an orientation is referred to as a "collection" orientation it should be appreciated that use of the apparatus is not limited to being oriented only in the collection orientation or that only human biological material collection may be performed while the apparatus is oriented in the collection orientation. The apparatus may be advantageously configured to permit performance of many different operations with the apparatus when the apparatus is oriented in the collection orientation. The apparatus is described with primary reference to processing human biological material comprising adipose, but the apparatus may be used for processing other biological material not comprising adipose.

The apparatus of the first aspect may be used in a variety of processing applications involving adipose or other human biological material. The apparatus may, for example, be used for preparation of concentrated or separated portions of the collected human biological material, for example to produce a stromal vascular fraction rich in leuko stromal vascular cells, including stem cells, derived from adipose tissue. As another example, the apparatus may be used for preparation of a fat graft comprising adipose. The apparatus has a design that accommodates retention of a target material (e.g., leuko stromal vascular cells or adipose) in a single container from collection through preparation of a concentrate product containing the target material. By target material, it is meant some component or components from or some portion or portions of collected human biological material of interest for recovery following processing in the apparatus, such as recovery in a concentrated or modified form relative to the collected human biological material (e.g., stromal vascular fraction concentrate rich in stem cells and other leuko stromal vascular cells, cleaned adipose-containing fraction for fat grafting applications).

The apparatus of the first aspect includes a container having an internal containment volume, with the internal containment volume comprising a tissue retention volume, a filtrate volume, a collection volume, and a tapered portion. The tissue retention volume and filtrate volume are separated by a filter. The collection volume is within the filtrate volume (i.e., is a part of the filtrate volume) and has a bottom elevation corresponding to a bottom elevation of the filtrate volume and a top elevation that is lower than the bottom elevation of the tissue retention volume. The tapered portion tapers in a downward direction with at least a portion of the tapered portion being located below (at a lower elevation than) the bottom elevation of the tissue retention volume. The apparatus includes an inlet port in fluid communication with the tissue retention volume and configured for introducing extracted biological material directly into the tissue retention volume, such as during a lipoplasty procedure. The apparatus includes a suction port that is in fluid communication with the filtrate volume and provides access to the filtrate volume for suctioning from the filtrate volume material that may pass through the filter from the tissue retention volume to the filtrate volume, for example biological fluids that may separate from biological material introduced into the tissue retention volume.

As noted, the tissue retention volume and the filtrate volume of the apparatus of the first aspect are separated by the filter. By being "separated" by the filter it is meant that the filter forms at least a portion of the defining physical separation between the tissue retention volume and the filtrate volume. As will be appreciated, the filter accommodates movement of fluid and undersize non-fluid material (e.g., liberated undersize cells, tissue fragments, etc.) between the tissue retention volume and the filtrate volume, while retaining oversize material within the tissue retention volume. In some applications (e.g., preparing a stromal vascular fraction concentrate), target material may comprise biological material that during processing in the apparatus passes through the filter and collects in the collection volume. As discussed below, the apparatus may be configured to be received in a centrifuge for centrifuging the apparatus, and such centrifuging may assist to concentrate such target material in the collection volume. In other applications (e.g., preparing a fat graft), target material (e.g., adipose) may be retained within the tissue retention volume following processing.

The apparatus may be used during multiple processing steps to prepare, for example, a stromal vascular fraction concentrate (e.g., concentrate rich in leuko stromal vascular cells) from human biological material comprising adipose or a fat graft containing adipose, without the need to transfer a target material being processed between different containers for different processing steps. The apparatus may be used initially to collect the human biological material (e.g. tissue and fluids) during a lipoplasty procedure or other tissue extraction procedure, or tissue that has already been extracted in another procedure may be introduced into the apparatus for processing. The apparatus may be portable and easily transportable between locations where collection or different processing operations may be conducted.

A number of feature refinements and additional features are applicable to the first aspect of the invention. These feature refinements and additional features may be used individually or in any combination. As such, each of the following features may be, but are not required to be, used with any other feature or combination of the first aspect.

The apparatus may include an extraction port in fluid communication with the internal containment volume and configured for removing processed biological material from the internal containment volume. Any or all of the inlet port, the suction port and the extraction port may be configured for access therethrough from above the container into the internal containment volume. The extraction port may be located above a portion of the filter, so that the advancing tip of a hypodermic needle pierces the filter when the tip of the hypodermic needle is advanced from the extraction port into the collection volume. The collection volume may include a nadir and the extraction port may be positioned above the nadir so that the tip of a hypodermic needle inserted through the extraction port may be advanced vertically downward to the vicinity of the nadir of the collection volume.

The apparatus may include a mixing device disposed at least in part within the tissue retention volume for mixing contents within the tissue retention volume. The mixing device may comprise a rotatable shaft extending from outside of the internal containment volume to inside of the internal containment volume. The shaft may be made of a polymeric or metallic material of construction. A preferred material of construction for the shaft is stainless steel, for example 303, 304 or 316 stainless steel. If a polymeric material of construction is used, it should preferably be high-strength, for example an Ultem™ resin composition available from Saudi Basic Industries Corp. (SABIC). The shaft may comprise at the top a tapered receptacle adapted to mate with a tapered syringe tip. The tapered receptacle may be fitted with an o-ring to seal against the tapered syringe tip when inserted into the tapered receptacle, thereby permitting a good suction to be applied by the syringe through the lumen to extract material from the tissue retention volume. The shaft may comprise a handle interface outside of the internal containment volume. The apparatus may further include a handle interfaced to the handle interface, wherein rotating the handle causes the shaft to rotate, thereby operating the mixing device. The handle may be removably interfaced to the handle interface, to permit the handle to conveniently be connected with the handle interface to operate the mixing device when appropriate and to conveniently be removed from the handle interface to permit access to a top of the apparatus without interference from the handle. The apparatus may include a lumen that extends through the shaft and has a proximal end located outside of the internal containment volume and a distal end located within the internal containment volume. Such a lumen may provide access from outside of the internal containment volume to inside of the internal containment volume. A removable plug for sealing the lumen may be disposed in the proximal end of the lumen. The shaft may be rotatable about an axis that extends through the collection volume. The lumen may be aligned with the axis. The lumen may provide access to the collection volume for aspiration of material therefrom and/or injection of material thereto.

The apparatus may be configured for advancing a hypodermic needle through a lumen and out of the distal end of the lumen to access the collection volume with an advancing tip of the hypodermic needle. The distal end of the lumen may be located in the tissue retention volume above a portion of the filter, so that the advancing tip of the hypodermic needle may pierce and pass through the filter when the tip of the hypodermic needle exits the distal end of the lumen and is advanced from the distal end of the lumen into the collection volume. The collection volume may include a nadir, and an axis of the lumen may be aligned so that the tip of a hypodermic needle exiting the distal end of the lumen may be advanced to the vicinity of the nadir of the collection volume. The hypodermic needle may thus access the collection volume to permit injection of material into and/or aspiration of material from the collection volume (e.g., aspiration of stromal vascular fraction concentrate or other processed biological material collecting in the collection volume during processing). The apparatus may be designed for single-use, and piercing the filter with a hypodermic needle may beneficially provide a safety mechanism for preventing reuse, and risks associated therewith, by damaging the filter in a way that renders the filter unsatisfactory for reuse.

The mixing device, or mixer, may comprise one or more mixing members disposed in the tissue retention volume and connected with the shaft, wherein the mixing member moves through the tissue retention volume when the shaft is rotated. For example, a mixing member may be in the form of impeller blades, paddles or arms that agitate and mix components within the tissue retention volume when the shaft is rotated. At least a portion of the tissue retention volume may be within the tapered portion of the internal containment volume (with at least a portion of the tapered portion being located above a bottom elevation of the tissue retention volume), and at least a portion of one or more such mixing member may be disposed within the tapered portion of the internal containment volume. The mixing device may include a filter contact member that moves when the shaft is rotated and movably contacts the filter. The filter contact member may be part of or separate from such a mixing member. The filter contact member contacts the filter at least periodically, and may contact the filter continuously when the shaft is rotated. The filter contact member may advantageously deform the filter when it moveably contacts the filter, promoting dislodgment of material from the filter to help prevent filter clogging.

As noted, the suction port is in fluid communication with the filtrate volume. By the suction port being in fluid communication with the filtrate volume, it is meant that the suction port is fluidly connected directly to the filtrate volume, and not indirectly through the tissue retention volume and the filter. The fluid communication may be provided by a dedicated conduit extending from the suction port to a desired location within the filtrate volume where it is desired to apply suction directly to the filtrate volume. The suction port may be in fluid communication with the tapered portion of the internal containment volume through a conduit providing fluid communication from the suction port to a location within the filtrate volume that is also within the tapered portion of the internal containment volume. The conduit may extend through the filtrate volume from adjacent the suction port to such a location within the filtrate volume. The suction port may be located above the tapered portion of the internal containment volume. The suction port may be configured for access through the suction port from above the container. The suction port may be configured for connection to a vacuum system to suction material from the filtrate volume, such as material that passes through the filter from the tissue retention volume to the filtrate volume.

The apparatus may include multiple suction ports. For example, the apparatus may include a first suction port as described in the preceding paragraph that is in fluid communication with a first location in the filtrate volume within the tapered portion of the internal containment volume through a first conduit, and the apparatus may include a second suction port through which components passing through the filter from the tissue retention volume to the filtrate volume may be suctioned from the filtrate volume through a second conduit extending from the second suction port to a second location within the filtrate volume. The second conduit may be configured to permit adjustment of the elevation of the second location within the filtrate volume. The second conduit may be translatable through the second suction port to adjust the elevation of the second location within the filtrate volume. The second conduit may be configured so that at any extent of such adjustment of the second location, the second location will always be at a higher elevation within the filtrate volume than the first location, which may be fixed. The second conduit may be configured to permit adjustment of the position of the second location within the filtrate volume at different elevations above the tapered portion of the filtrate volume. The second conduit may be configured to permit positioning the second location at an elevation corresponding with an interface between the tapered portion of the filtrate volume and a portion of the filtrate volume located above the tapered portion, which may be the lowest elevation to which adjustment is permitted. The second suction port may be configured for access through the second suction port from above the container.

Any one or more of the inlet port, the suction port of other ports providing access to the internal containment volume may be configured for access through the port from above. In this way, access through each such port may be conveniently from above the apparatus, providing a significant advantage to a user of the apparatus in that such a user may focus all access manipulations from above the apparatus while the apparatus is in a normal position in the collective orientation, for example with the apparatus freestanding on a flat work surface such as a table or counter. Complexities associated with access from the side or from below may be avoided, including the complexity of sealing and providing access into side or bottom access ports against a positive fluid head that may be present in the container and the complexity of awkward side of bottom interactions by users. Although such access from above the container may be at some angle relative to vertical, in a preferred implementation the access through such port is in a vertical direction from above the container. In one preferred implementation, all access to the internal containment volume may be through access ports wherein each such access port (e.g., inlet port, suction port, extraction port, other ports) is configured for access through the access port only from above the container. In another preferred implementation, all access ports may be configured for access through each such access port in a vertical direction from above the container.

The tapered portion may have a cross-sectional area that tapers, or reduces in size, in a direction toward the bottom of the collection volume. The tapered portion of the containment volume helps to direct and concentrate target dense material (e.g., dense cells, stromal vascular fraction) toward and into the collection volume. The tapered portion of the containment volume may have a conical shape or any other shape with a cross-sectional area that tapers to reduce in size in a direction toward the bottom of the collection volume. In various implementations, at least a part of the tapered portion may be located above the collection volume.

The container may have a self-supporting structure, with the container having rigid walls or rigid structural supports to maintain the container in a particular configuration. The container may be made of any suitable material or materials of construction. The container may be made of one or more plastic composition. The container may have transparent walls. A preferred material of construction for the container is a clear polymeric material, such as for example a clarified polypropylene composition. Clarified polypropylene compositions provide low cellular adhesion and reasonable clarity. The container may be comprised of multiple pieces, which may all be made out of the same material of construction or one or more of such pieces may be made of a different material of construction.

The container may comprise a fluid containment shell with an internal cavity portion forming at least a part of the internal containment volume. The internal cavity portion may be open to above. The container may include a lid attached to the shell and disposed to cover from above the internal cavity portion. One or more than one of the suction port the inlet port or other access port may pass through the lid. In one preferred implementation, all access into the internal containment volume may be only through one or more openings, or ports, passing through the lid. The filter may be suspended from the lid. The mixing device may be supported by the lid and extend vertically downward from the lid into the tissue retention volume. The apparatus may include a flow barrier skirt extending between 5 mm and 50 mm downward from the lid into the internal containment volume. The shell may comprise walls around the internal cavity portion except where the cavity portion is open to above, and the apparatus may be configured with no access into the internal containment volume through the walls of the shell. The shell may comprise an upper portion having a first wall surface portion defining a corresponding upper portion of the internal containment volume. Substantially all of the first wall surface portion may have a steep incline relative to horizontal, for example an incline of at least 65°, preferably an incline of at least 75° and more preferably an incline of about 90° (vertical wall surface). The shell may include a lower portion located below the upper portion and having a second wall surface portion defining a corresponding lower portion of the internal containment volume, and the second wall surface portion may include a tapered wall surface portion defining the tapered portion of the internal containment volume. The tapered wall surface portion may have a less steep incline relative to horizontal than the first wall portion of the upper portion. The incline relative to horizontal of the tapered wall portion, or of the entire second wall portion when comprised entirely of the tapered wall portion, may be in a range having an upper limit of 70°, 65°, 60° or 65° and a lower limit of 20°, 25°, 30° or 35°, with one preferred range being form 30° to 60°. The tapered portion of the internal containment volume may occupy substantially the entire lower portion of the internal containment volume, and the second surface may be made up entirely or substantially entirely by the tapered wall surface. At least a first portion of the filter may be disposed in the upper portion of the internal containment volume and a second portion of the filter may be disposed in the lower portion of the internal containment volume. The incline of each of the first wall surface portion, the second wall surface portion and the tapered wall surface portion need not be uniform, however all portions of the first wall surface portion may preferably be at a steeper incline than the incline of any portion of the tapered wall surface portion.

There are a number of advantages that may be available with configurations of the preceding paragraph including an upper portion having a steeper wall surface incline and a lower portion having a less steep wall surface incline. Such a structure advantageously accommodates a larger proportion of the internal containment volume being allocated to the tissue retention volume, with a larger portion of the tissue retention volume in the upper portion of the shell and a smaller portion of the tissue retention volume in a lower portion of the shell. The tapered wall surface portion of the lower portion of the shell helps to direct fluid and other material in the filtrate volume toward the bottom of the filtrate volume for efficient collection and removal. In applications where target material is to be collected in the collection volume, the tapered wall surface also directs material toward the collection volume, which may generally be located in a bottom portion of the filtrate volume. The apparatus may also be configured to be centrifugable, and centrifuging will tend to accelerate concentration of a most dense fraction (e.g., stromal vascular fraction) in the collection volume.

More generally, the tapered portion of the internal containment volume may have a tapered portion nadir corresponding with a bottom elevation of the internal containment volume. The bottom elevation of the collection volume may correspond with the bottom elevation of the internal containment volume. Wall surfaces of the container defining the tapered portion of the internal containment volume may coverage at a point at the tapered portion nadir. This is a particularly beneficial configuration, especially for applications when target material is to be collected in and removed from the collection volume in the vicinity of the tapered portion nadir.

The apparatus may be configured with a very convenient size from a number of perspectives, and with efficient use of the internal containment volume to facilitate efficient collection of biological material and versatility in post-collection processing. The apparatus may be sized for convenient hand transportation, such as between a location where human biological material may be collected to other, different locations, where various processing of collected material may be carried out. The apparatus may also be sized for convenient manipulation by a person.

For many applications, the apparatus may be sized and configured such that the internal containment volume has a volume in a range with a lower limit of 100 cubic centimeters, 300 cubic centimeters, 500 cubic centimeters, 600 cubic centimeters or 700 cubic centimeters and an upper limit of 1500 cubic centimeters, 1300 cubic centimeters, 1100 cubic centimeters, 1000 cubic centimeters, 900 cubic centimeters or 800 cubic centimeters. One preferred range for many applications is for the internal containment volume to be in a range of 700 cubic centimeters to 1000 cubic centimeters. By internal containment volume, it is meant the total internal volume contained within the walls defining the container, including volume that is occupied by internal hardware, such as for example may be occupied by a mixing device, barrier member, suction conduits, barrier skirt, etc. As will be appreciated, less than all of the internal containment volume will be available for processing within the internal containment volume.

The terms "available processing volume", "useful volume" and "internal processing volume" are used interchangeably herein to refer to the portion of the internal containment volume that is effectively available to receive and process human biological material and additives (e.g. wash liquid, enzyme solution, other additives) during use of the apparatus for collection of biological material or for post-collection processing. This available processing volume is equal to the internal containment volume less portions of the internal containment volume occupied by hardware (e.g., mixing device, filter, skirt, suction tubes, barrier member, etc.) and less unoccupied portions of the internal containment volume not effectively accessible for occupation by biological material during collection operations or by biological material or additives during post-collection processing. For example, the available processing volume may exclude a small volume at the top of the container that is above a bottom extension of the inlet port into the internal containment volume. This small void space may be beneficial to permit space for fluid to slosh within the container when contents of the container may be internally mixed or externally agitated (e.g., by a shaker table). For many applications, the available processing volume may be in a range having a lower limit of 75 cubic centimeters, 200 cubic centimeters, 400 cubic centimeters, 500 cubic centimeters, 600 cubic centimeters, 650 cubic centimeters or 700 cubic centimeters and an upper limit of 1300 cubic centimeters, 1100 cubic centimeters, 1000 cubic centimeters, 900 cubic centimeters, 850 cubic centimeters, 800 cubic centimeters or 750 cubic centimeters. In one preferred implementation for many applications, the available processing volume may be in a range of from 700 cubic centimeters to 850 cubic centimeters.

Advantageously, the apparatus may be configured so that a large portion of the available processing volume is within the tissue retention volume, while still permitting a high level of performance for various processing operations. The tissue retention volume may comprise at least 60 percent, at least 65 percent or at least 70 percent of the available processing volume with the container. Often, the tissue retention volume will comprise not more than 95 percent, not more than 90 percent or not more than 85 percent of the available processing volume. For many preferred implementations, the tissue retention volume may comprise a portion of the available processing volume that is at least 400 cubic centimeters, at least 500 cubic centimeters, at least 600 centimeters or at least 650 cubic centimeters. The apparatus may advantageously be configured with only a small portion of the available processing volume occupied by the collection volume, located below the filter. For example, the collection volume may comprise no more than 10 percent, no more than 7 percent or no more than 5 percent of the available processing volume.

For many preferred implementations the collection volume may be no larger than 75 cubic centimeters, no larger than 50 cubic centimeters, no larger than 30 cubic centimeters or no larger than 20 cubic centimeters. The collection volume may often be at least 1 cubic centimeter, at least 2 cubic centimeters or at least 3 cubic centimeters. In one preferred implementation, the collection volume may be in a range of from 10 cubic centimeters to 30 cubic centimeters. Typically, the entire collection volume will make up part of the available processing volume.

The apparatus may be sized and configured to be containable within a relatively small envelope volume which may be particularly advantageous given the relatively large internal containment volume, available processing volume and tissue retention volume that may be provided in the container. For some preferred implementations, the apparatus may be sized and configured to be containable within a first envelope volume defined by a rectangular cuboid having a length dimension of no more than 16 centimeters, a depth dimension of no more than 15 centimeters and a height dimension of no more than 18 centimeters. However, the apparatus may be sized and configured to have some minimum size, for example as a function of a desired size of internal containment volume, available processing volume or tissue retention volume.

For some preferred implementations, the apparatus may have a size and configuration such that the apparatus may not be containable within a second envelope volume defined by a rectangular cuboid having any one or more of a length dimension, depth dimension or height dimension that is smaller than 10 centimeters, i.e., the apparatus would not fit within any rectangular cuboid smaller than 10×10×10 centimeters.

The filter may be of any appropriate filter media design. The filter may be any porous structure with openings sized to make a desired separation. The filter may be in the form of a mesh filter bag disposed within the internal containment volume, and that separates the internal containment volume between the tissue retention volume and the filtrate volume located on opposite sides of the filter bag. The filter may be a rigid mesh screen. In some implementations, the filter may have a separation size in a range having a lower limit of 70 microns, 100 microns, 150 microns, at 175 microns, 200 microns, 300 microns or 400 microns and an upper limit of 800 microns, 700 microns, 600 microns, 500 microns, 475 microns, 450 microns, 425 microns, 400 microns, 350 microns, 300 microns or 250 microns; provided that the upper limit is larger than the lower limit. Leuko stromal vascular cells will easily pass through a 200 micron filter, however a somewhat larger filter size may be advantageous to promote recovery of most or substantially all of the leuko stromal vascular cells in the filtrate volume. Smaller size filters may plug to a degree that significantly reduces cell yield in terms of cell collection in and recovery from the filtrate volume. In one implementation, the filter may have a separation size in a range having a lower limit of 70 microns and preferably 80 microns and an upper limit of 125 microns, preferably 110 microns and more preferably 100 microns. By separation size, it is meant the size at which the filter effects separation between particles passing through and particles rejected by the filter during normal operation. The separation size may be determined by the size of openings provided in a surface filter, such as the mesh size of a mesh bag filter or of a rigid mesh screen filter.

In one preferred implementation, the filter may be a mesh filter. With a mesh filter, the separation size will be the size of the mesh openings. In one preferred implementation, whether or not the filter is a mesh filter, the separation size for the filter, and the size of mesh openings when a mesh filter is used, may be in a range as described above for separation size. In some implementations, the size of the mesh openings may be in a range having a lower limit of 70 microns, 80 microns, 90 microns, 100 microns, 125 microns or 150 microns and having an upper limit of 400 microns, 350 microns, 300 microns or 250 microns. One range for some applications is from 150 microns to 250 microns, including for preparation of a fat graft or preparation of a stromal vascular fraction concentrate. The mesh filter may be of a flexible or a rigid mesh material. In a preferred implementation, the filter may be made of mesh material, more preferably a nylon mesh material. The filter need not be continuous, and may be comprised of discrete filter areas disposed at different locations between the tissue retention volume and the filtrate volume. Alternatively, the filter may be comprised of a single continuous filter area. The filter defines at least part of the physical separation between the tissue retention volume and the filtrate volume; it need not define all of the physical separation between the issue retention volume and the filtrate volume. For example, there may be internal walls defining at least a part of the physical separation between the tissue retention volume and the filtrate volume, with an example being a skirt barrier that may be disposed at the top of the internal containment volume and that may define a separation between the tissue retention volume and the filtrate volume in an upper portion of the internal containment volume. Another example may be a barrier member that blocks access from the tissue retention volume into the collection volume portion of the filtrate volume. As another example, the filter may include filter areas supported by a frame, with structural members of the frame defining a part of the physical separation between the tissue retention volume and the filtrate volume. In a preferred implementation, the portion of the physical separation between the tissue retention volume and the filtrate volume that is provided by the filter should generally be large to provide as much filter surface area as reasonably possible.

The apparatus may be configured to be received by a centrifuge for centrifuging. For example, the apparatus may be conveniently sized and configured to be received within a centrifuge bucket, and preferably of a commercially available centrifuge. For example, the apparatus may advantageously be sized and configured to fit within a bucket of a bucket assembly for a Sorvall ST-40 centrifuge. Two or more of the apparatus may be centrifuged simultaneously in a centrifuge. In one preferred implementation, the apparatus may be sized and configured so that two of the apparatus may be simultaneously centrifuged together in a dual bucket assembly, wherein each apparatus counterbalances the other apparatus during centrifuging, for efficient processing. Alternatively one apparatus could be processed within a blank weight as a counterbalance. The apparatus may be received in a centrifuge bucket with the bottom of the apparatus adjacent to and facing the bottom of the bucket.

Configuring the apparatus for centrifuging may be particularly advantageous for applications when target material is to be collected in the collection volume, such as for collecting a stromal vascular fraction concentrate in the collection volume. The collection volume is advantageously positioned in the bottom portion of the internal containment volume where the most dense materials will collect during centrifuging.

The apparatus may include an extraction port in direct fluid communication with the filtrate volume and through which material is removable from the filtrate volume separate from the suction port. In a preferred implementation, access through the extraction port is in a vertical direction from above the container, for example with the extraction port passing through the top of the container. Although not a preferred implementation, in various applications the apparatus may include an extraction port that is adjacent a bottom elevation of the filtrate volume and configured for access to the collection volume.

The apparatus may be configured for the addition of additives to the internal containment volume, and in particular directly into the tissue retention volume. As used herein, such an additive is any material added to the internal containment volume other than the human biological tissue comprising adipose, such as from a lipoplasty procedure, to be processed in the apparatus. Such an additive may be added for example to aid processing within the apparatus or to become part of a composition including target material to be recovered from the apparatus for following processing. Examples of some additives to aid processing may include wash liquid, enzymes or surfactants. Examples of some additives that may become part of a fat graft composition include hormones (e.g., human growth hormone, insulin), buffers (e.g., sodium bicarbonate) and cells (e.g., bone marrow-sourced stem cells, cultured adipose-sourced stem cells, stromal vascular cells from adipose tissue). Such additives may be added to the tissue retention volume through the inlet port.

The apparatus may further include a second port in fluid communication with the tissue retention volume for introducing an additive directly into the tissue retention volume or for removing material (e.g., adipose tissue) from the tissue retention volume. The second port may be smaller than the inlet port through which the human biological material to be processed (e.g., from a lipoplasty procedure) is introduced into the tissue retention volume. The second port, which may be referred to as an auxiliary port or as an additive port, may be conveniently sized and configured for insertion therethrough of a hypodermic needle from which an additive material may be ejected from the needle into the tissue retention volume or through which material may be removed from the tissue retention volume. This auxiliary port may be configured to make a luer connection with a syringe, in which case a syringe may be attached to the auxiliary port and the container tipped (inclined) in the direction of the auxiliary port to facilitate suctioning material from the tissue retention volume directly into the syringe without the need for a needle or cannula, and may be drawn into a syringe in fluid communication with the hollow member.

The apparatus may include human biological material, which may include target material from human biological material originally collected in the apparatus disposed within the internal containment volume (e.g., the apparatus during some stage of use). The apparatus may include adipose-containing material (e.g., collected material including adipose tissue) in the tissue retention volume. The apparatus may include in the tissue retention volume an adipose-containing fat graft composition, including any desired additives, ready to be withdrawn from the tissue retention volume and used in a fat graft procedure. The apparatus may include a stromal vascular fraction concentrate disposed in the collection volume.

The apparatus may be packaged within a hermetic enclosure, for example as packaged for transportation and storage prior to use. The apparatus may be sterilized prior to packaging and maintained in a sterile environment within the hermetic enclosure at least until the apparatus is removed from the hermetic enclosure for use. The apparatus may be designed for a single use following removal from the hermetic enclosure. After such single use, the apparatus may be disposed of in an appropriate manner.

The apparatus may be fluidly connected through the inlet port to a pre-filter. The fluid connection may be through a conduit that fluidly connects the inlet port to a downstream side of a pre-filter unit comprising the pre-filter. The pre-filter unit may comprise a housing with the pre-filter disposed within the housing, and with an inlet on an upstream side of the pre-filter and an outlet on downstream side of the pre-filter. The upstream side of the pre-filter may be in fluid communication with a lipoplasty cannula to receive extracted biological material during a lipoplasty procedure and to pre-filter the biological material prior to delivery to the inlet port of the apparatus, for example to remove some collagen from the biological material upstream of the apparatus. The pre-filter may be provided with my convenient separation size, for example in a range having a lower limit of 0.5 millimeter or 1 millimeter to an upper limit of 5 millimeters, 3 millimeters or 2 millimeters. The pre-filter may comprise a mesh screen with mesh openings sized, for example, in such a range.

A second aspect of the invention is provided by a method for processing tissue from a lipoplasty procedure within a containment volume of a portable tissue collection and processing apparatus to prepare within the apparatus a concentrate product comprising at least one target component of the tissue. The apparatus comprises a filter and a container having an internal containment volume, wherein the internal containment volume comprises a tissue retention volume and a filtrate volume separated by the filter. The method comprises washing the tissue with a wash liquid, with the washing comprising adding the wash liquid to the internal containment volume to contact tissue within the tissue retention volume and passing through the filter and removing from the filtrate volume at least a portion of the wash liquid along with one or more component, typically a non-target component, washed from the tissue while retaining washed tissue within the tissue retention volume. After the washing, the method comprises digesting tissue within the containment volume. The digesting comprises adding enzyme to the containment volume to contact at least a portion of washed tissue within the tissue retention volume. The enzyme is of a type capable of breaking down a portion of the washed tissue to release the target component in a form capable of passing through the filter, and which may then be recovered through the filtrate volume. The digesting comprises, after adding the enzyme, agitating the contents of the containment volume for a time and at a temperature sufficient to release the target component in such a form capable of passing through the filter. After the digesting, the method comprises centrifuging the apparatus to prepare in the filtrate volume a concentrate product comprising the target component.

A number of feature refinements and additional features are applicable to the second aspect of the invention. These feature refinements and additional features may be used individually or in any combination. As such, each of the following features may be, but are not required to be, used with any other feature or combination of the first aspect.

The portable tissue collection and processing apparatus may be an apparatus according to the first aspect of the invention. The method may include one or more steps in addition to the washing, digesting and centrifuging steps. Any such additional step may be performed either prior to the washing, between the washing and digesting, between the digesting and centrifuging, or after the centrifuging. The agitating performed during the digesting may be performed, for example, using an assembly of an apparatus and agitation device according to the second aspect of the invention. The agitating may be performed by or may involve use of a mixing device disposed within the internal containment volume. The centrifuging may be performed, for example, using an assembly of an apparatus received in a centrifuge according to the second aspect of the invention.

In one implementation, the washing may comprise a multi-stage operation with multiple occurrences of adding wash liquid followed by removing used wash liquid from the filtrate volume. The washing may comprise, after adding the wash liquid to the containment volume, centrifuging the apparatus prior to the digesting to help separate wash liquid from tissue that is retained in the tissue retention volume. Following the centrifuging, wash liquid collecting in the filtrate volume may be removed from the filtrate volume prior to the digesting, such as for example through the suction port and/or through the extraction port. When the washing comprises multiple washing stages, each such stage may comprise adding wash liquid to the containment volume followed by centrifuging the apparatus. The washing may be in the absence of such centrifuging. The washing may comprise, after adding the wash liquid, mixing contents (including the wash liquid) in the tissue retention volume (e.g., by operating a mixer in the tissue retention volume), discontinuing the mixing after some period of time and suctioning the fluids from the filtrate volume. The washing may comprise multiple stages with multiple occurrences of adding wash liquid, mixing, discontinuing mixing and suctioning. Following discontinuing the mixing, some quiescent time may be allowed for decantation of liquid prior to commencing the suctioning. The wash liquid may comprise any suitable liquid for washing the tissue within the tissue retention volume. The wash liquid may be or comprise a saline solution, for example a phosphate buffer solution. The saline may be warmed, for example to approximately normal human body temperature, prior to introduction into the tissue retention volume.

The enzyme added to the containment volume during the digesting preferably includes collagenase, which may be accompanied by a neutral protease. The agitating may be accomplished by shaking the apparatus mounted on a shaker, preferably with control of temperature, such as on a warming shaker. The agitating may comprise mixing contents within all or part of the internal containment volume through operation of a mixing device disposed in the internal containment volume, for example a rotating mixing member (e.g., blade, impeller), preferably with control of temperature. During the agitating, the apparatus may be maintained at a relatively constant temperature, for example, between about 35° C. and 39° C., and preferably around 37° C.

The method may comprise prior to the washing, collecting the tissue in the tissue retention volume of the container. Collecting the tissue may be accomplished during a lipoplasty procedure (e.g., lipo surgery) on a patient, such as by conducting adipose tissue that is being removed from the patient into the tissue retention volume through a conduit fluidly connected with the apparatus. The collecting may comprise, during such a lipoplasty procedure, suctioning at least a portion of fluid collecting in the filtrate volume to remove such fluid from the filtrate volume and from the apparatus. Such fluid may comprise liquid and/or small particles that pass through the filter from the tissue retention volume into the filtrate volume during the lipoplasty procedure. Such fluid may be removed from the filtrate volume by suction through the suction port. Applying suction to the internal containment volume has the benefit of pulling filterable components through the filter into the filtrate volume for removal. Removing such fluid from the filtrate volume permits the filtrate volume to be kept small because it is not necessary to contain all fluid that may separate from the adipose tissue and pass through the filter during a lipoplasty procedure. This provides the advantage of allowing the tissue retention volume to be made proportionally larger to collect a larger quantity of desired tissue during a tissue collection operation. Applying suction to the filtrate volume aids separation of fluid components from the adipose tissue, further providing an advantage of reducing the portion of tissue retained and allowing a larger quantity of desired tissue to be collected during the collection operation.

The method may comprise after the collecting and prior to the washing, disconnecting the apparatus from the conduit through which it received adipose tissue, sealing the containment volume and transporting the apparatus from a first location where the collecting is performed to a second, different location where the washing is performed. The method may comprise after the centrifuging, selectively removing the concentrate product from the filtrate volume. For example, when using an apparatus of the first aspect of the invention, the concentrate product may collect in a collection volume, which may be in a collection chamber at the bottom of the collection volume. The concentrate product may be selectively removed from the collection volume through an extraction port. By "selectively removing", it is meant that the concentrate product is removed separate from one or more other materials present in the filtrate volume following the centrifuging. For example, the filtrate volume may contain multiple different material phases of different densities within the filtrate volume, whether or not multiple phases are present in the collection volume. The targeted concentrate product may be one or more of these phases. During the selectively removing, the desired phase or phases representing the concentrate product are removed separate from some or all of the other phases that may be present in the filtrate volume. In one preferred implementation of the method, a target component comprises stem cells from adipose tissue. The concentrate product may comprise a stromal vascular fraction, which may be in a cell fraction collecting at the bottom of the collection volume. In the case in particular of a stromal vascular fraction in the concentrate product, there may be a phase rich in red blood cells that collect in the collection volume below, and possibly grades into, the bottom of the stromal vascular fraction. There may also be one or more less dense fractions above the stromal vascular fraction within the filtrate volume, some of which may also occupy a portion of the collection volume above the stromal vascular fraction. In one implementation, such a red blood cell phase may be removed from the filtrate volume, for example through the extraction port, prior to removal of the stromal vascular fraction, when the extraction port is adjacent the bottom of a collection chamber. The red blood cell phase may be removed from the filtrate volume together with the stromal vascular fraction in a combined cell fraction. Through thorough washing during the washing operation, the red blood content in such a concentrated cell fraction may be kept relatively small, such that the stromal vascular fraction may be utilized directly in the recovered concentrated cell fraction containing the relatively small red blood cell content. If desired, after removal from the apparatus such a red blood cell phase may be separated from the stromal vascular fraction by known techniques. In one implementation, the concentrate product, such as containing a stromal vascular fraction, is in the form of a pellet, and to facilitate removal of the concentrate product, the concentrate product is diluted in the filtrate volume with a diluent fluid and a diluted concentrate product is then removed from the filtrate volume. The diluent fluid may comprise or be a saline solution, such as for example a phosphate buffer solution. Prior to removing the stromal vascular fraction, one or more less dense layers may first be removed from above the stromal vascular fraction, such as via a suction port.

A third aspect of the invention is provided by a method for processing human biological material comprising adipose within an internal containment volume of an apparatus. The method includes washing the human biological material with a wash liquid. The washing includes adding the wash liquid to the internal containment volume to contact the human biological material within a tissue retention volume within the internal containment volume. Within the internal containment volume, a filter separates the tissue retention volume form a filtrate volume. The washing further includes passing through the filter and removing from the filtrate volume at least a portion of the wash liquid along with one or more components washed from the human biological material while retaining washed human biological material in the tissue retention volume.

A number of feature refinements and additional features are applicable to the third aspect of the invention. These feature refinements and additional features may be used individually or in any combination. As such, each of the following features may be, but are not required to be, used with any other feature or combination either of the first or second aspect.

The apparatus may be an apparatus according to the first aspect of the invention.

The washing may be according to the washing described with respect to the second aspect. For example, the washing may or may not involve centrifuging after adding wash liquid, and may involve a single washing stage or may involve a multi-stage washing operation.

The method may further include adding an additive to the washed human biological material in the tissue retention volume. The method may further include mixing the washed human biological material to disperse the additive in the washed human biological material. The mixing may include moving a member within the tissue retention volume. The additive may comprise an ingredient for delivery to a patient in a fat graft. The additive may, for example, be any of the additives listed for possible inclusion in a fat graft composition as discussed in relation to the first aspect.

The method may include removing from the tissue retention volume at least a portion of the washed human biological material for use in a fat graft.

The method may comprise, prior to the washing, collecting the human biological material. The collecting the human biological material may include, during a lipoplasty procedure on a patient, conducting a human biological material feed comprising at least a portion of extracted human biological material removed from the patient into the tissue retention volume. The collecting may include, during the lipoplasty procedure, passing fluid separating from the human biological material feed through the filter into the filtrate volume and suctioning at least a portion of the fluid from the filtrate volume and out of the apparatus. After the collecting and prior to the washing, the method may include sealing the containment volume and transporting the apparatus from a first location where the collecting is performed to a second, different location where the washing is performed.

A fourth aspect of the invention is provided by a method of processing adipose tissue to concentrate leuko stromal vascular cells associated with the adipose tissue. The method combines particular processing in combination with a portable container to address significant design constraints associated with the use of portable containers for multi-step processing of adipose tissue. The method of the fourth aspect includes multi-step processing within a portable container having a filter inside the container. The multi-step processing includes washing the adipose tissue within the container to remove contaminants from the adipose tissue. The washing includes multiple wash cycles, with each wash cycle comprising: adding a volume of aqueous wash liquid to the container to contact the adipose tissue within the container; mixing the wash liquid and the adipose tissue in the container; and removing at least a majority of the wash liquid with contaminants from the container on a first side of the filter and retaining at least most of the adipose tissue in the container disposed on a second side of the filter. The method includes digesting adipose tissue within the container. The digesting is performed after the washing. The digesting comprises adding to the container of volume of digestion medium comprising a collagenase enzyme solution to contact washed adipose tissue in the container following the washing, wherein the volume ratio of the volume of digest medium to volume of adipose tissue within the container is in a range of from 0.6:1 to 2:1 and wherein the digestion medium provides from 150 to 300 collagen digestion units (CDU) per milliliter of catalytic volume, and wherein the catalytic volume is the total of the volume of digestion medium and the volume of adipose tissue within the container. The digesting also comprises, after adding the volume of digestion medium, permitting enzymatic digestion within the container for a retention time in a range of from 20 minutes to 50 minutes while the container is disposed in a temperature controlled environment with the temperature controlled environment maintained within a temperature range of from 32° C. to 38° C. and with at least occasional agitation of contents within the container. The method also includes, not later than 50 minutes following adding of the volume of digestion medium, adding a stopping reagent to the container to stop enzymatic activity within the container. The method also comprises disposing the container in a centrifuge and centrifuging the container in the centrifuge deform density-separated phases within the container. The density-separated phases include lower-density material phases and a higher-density pellet phase comprising leuko stromal vascular cells. After the centrifuging, the method includes removing the container from the centrifuge and removing the lower-density material phases from the container while retaining the pellet phase within the container.

The method particularly addresses processing within the constrained context of multiple-step processing within a single portable container. The method may permit effective processing within such a portable container in a manner to address inherent equipment and processing design problems associated with multi-step processing in portable containers and without excessive losses of cell viability or physical losses of cells to adherence to equipment and container surfaces inside the container.

A number of feature refinements and additional features are applicable to the fourth aspect of the invention. These feature refinements and additional features may be used individually or in any combination. As such, each of the following features may be, but are not required to be, used with any other feature or combination of the fourth aspect or the first aspect of the invention.

In preferred implementations, the portable container may be a container of an apparatus of the first aspect of the invention. The first side of the filter within the container may be the filtrate volume and the second side of the filter in the container may be the tissue retention volume of a container of an apparatus of the first aspect of the invention. Alternatively, the portable container may be other than a container of the apparatus according to the first aspect of the invention.

The step of removing the lower-density material phases may include removing such lower-density material phases from the container in sequence of increasing density, which may include suctioning the lower-density material phases from the container through an open end of a suction conduit disposed in the container. Preferably, such an open end of a suction conduit may be disposed in the container not directly above the pellet phase, to reduce the possibility that suction created in the container would structurally disrupt the pellet phase. In some preferred implementations, the pellet phase remains in place and stationary, relative to the container, while the lower-density material phases are removed. During the centrifuging, the pellet phase may form at a location within the container adjacent a bottom of the internal containment volume, and the pellet phase may remain at the location during the removing the lower-density material phases. In some implementations, removing the lower-density material phases may include tipping the container during suctioning of lower-density material phases to promote flow of at least a final suction portion of the lower-density material phases within the container laterally away from the pellet and toward the open end of the suction conduit. The container may include a corner located lateral to the pellet phase, and which may be located at an elevation of the container that is higher than the bottom elevation of the pellet phase, or even higher than a top elevation of the pellet phase. The tipping may promote flow of fluid of the lower-density material phases laterally toward the corner for suctioning from the vicinity of the corner into the open end of the suction conduit. In some preferred implementations, the lower-density material phases are removed through a top of the container.

The method may include one or more steps in addition to the steps noted above. Any such additional step may be performed between any of the steps noted above or may be performed prior to the washing or after the removing of the lower-density material phases from the container.

The method may include introducing aqueous suspension liquid into the container and dispersing cells of the pellet phase in the suspension liquid, such as to form a dispersion of the cells in the suspension liquid. The suspension liquid may be introduced into the portable container apparatus after the lower-density material phases have been removed. The suspension liquid may be introduced at a volume in a range having a lower limit of 1, 2, 3 or 5 milliliters and an upper limit of 25, 20, 15 or 12 milliliters. A volume of suspension liquid of about 10 milliliters may be used for many implementations. A volume ratio of the suspension liquid to the volume of the pellet phase may be in a range having a lower limit of 1:1, 2:1, 3:1 or 5:1 and an upper limit of 25:1, 20:1, 15:1 or 12:1. A volume ratio of about 10:1 may be used in many implementations. After being dispersed in a suspension liquid, the suspension liquid with dispersed cells may be removed from the container. Preferably at least most of the suspension liquid is removed from the container and more preferably substantially all of the suspension liquid and substantially all of the cells from the pellet phase are removed from the container with the suspension liquid. During the centrifuging, the pellet phase may form within the portable container apparatus adjacent a bottom of the internal containment volume where the suspension liquid may mix with the pellet phase to form the suspension. The suspension liquid and dispersed cells may be removed through a top of the container, even though suspension liquid and dispersed cells may be removed from a location adjacent a bottom of the container. This suspension liquid and dispersed cell may be removed upward through a hollow member disposed downward into the container, for example through a hollow needle or cannula, and may be drawn into a syringe in fluid communication with the hollow member. In some implementations, such a hollow member may pierce and extend across the filter.

The method may include removing leuko stromal vascular cells of the pellet phase from the container, which may include the use of a suspension liquid as noted above. At least a majority of the leuko stromal vascular cells of the pellet phase may be removed from the portable container apparatus, and preferably all or almost all of the leuko stromal vascular cells of the pellet phase are removed from the container.

The digestion medium may provide collagen digestion units (CDU) per milliliter of catalytic volume within a range that is narrower than the range listed above. Such a range may have a bottom limit of 150, 175 or 200 CDU and an upper limit of 300, 275 or 250 CDU. In some implementations, the digestion medium may provide about 225 CDU per millimeter of catalytic volume. In this regard, the catalytic volume is the total volume of the digestion medium added to the container and the volume of adipose tissue already disposed within the container when the digestion medium was added. For example, if the volume of digestion medium added to the container equals the volume of adipose tissue already disposed within the container, then the digestion medium will need to contain a concentration of collagenase enzyme that is twice as large as the desired concentration relative to the catalytic volume. As will be appreciated, the adipose tissue as collected will have associated contaminants, but in preferred applications with thorough washing, the adipose tissue should be cleaned of most contaminants so that substantially all of the volume of material on the second side of the filter in the container will be adipose tissue.

The volume ratio of digestion medium to adipose tissue may be in a narrower range than that described above. Such a volume ratio may have a lower limit of 0.6:1, 0.75:1 or 0.9:1 and may have an upper limit of 2:1, 1.75:1, 1.5:1 or 1.25:1. For various implementations, the volume ratio of digestion medium to washed adipose tissue may be about 1:1.

The retention time during the digesting may be within a narrower range than that described above. The retention time may be in a range having a lower limit of 20 minutes, 25 minutes or 30 minutes and an upper limit of 50 minutes, 45 minutes or 40 minutes. For various implementations, the retention time may be about 35 minutes.

The digesting may include continuous agitation of the contents during some portion or substantially all of the retention time. The agitation may include mixing, periodically or continuously, with a rotatable mixer disposed within the container. The agitation may include periodic or continuous movement of the container to cause agitation of contents within the container. The agitation may include shaking the container, such as on a warmer-shaker. The temperature controlled environment may be provided by a warmer-shaker.

Temperature control may be implemented at various points in the processing of the method. The digestion medium when added to the container may be within a temperature range having a lower limit 32° C., 33° C., 34° C. or 35° C. and an upper limit of 38° C. or 37° C. The temperature within the temperature controlled environment may be maintained in a narrower range than that stated above. The temperature controlled environment may be maintained within a temperature range having a lower limit of 32° C., 33° C., 34° C. or 35° C. and an upper limit of 38° C. or 37° C. The wash liquid, when added to the container, may be within a temperature range having a lower limit of 32° C., 33° C., 34° C. or 35° C. and an upper limit of 38° C. or 37° C.

For each wash cycle, a volume ratio of wash liquid addition may be controlled. The volume ratio of wash liquid addition refers to a volume ratio of the volume of wash liquid to a volume of adipose tissue within the container to which the wash liquid is being added during the wash cycle. The volume ratio of wash liquid addition may be in a range having a lower limit of 0.5:1, 0.7:1 or 0.8:1 and an upper limit of 4:1, 3:1, 2:1 or 1.5:1. For many implementations, the volume ratio of wash liquid addition may be about 1:1. A cumulative volume ratio of wash solution addition may be at least 2:1, or at least 3:1. The cumulative volume ratio of wash solution addition refers to a sum of the volume ratios for all of the wash cycles.

The washing may include more than two wash cycles. In some implementations, the washing may comprise at least three wash cycles. For many implementations, three wash cycles may be sufficient, while for other implementations, two wash cycles may be sufficient.

Each wash cycle may comprise removing wash liquid (preferably at least a majority of the wash liquid and more preferably substantially all of the wash liquid) by suctioning from the container on the first side of the filter (from the filtrate volume). During such suctioning, the wash liquid may be removed through a top of the container.

Mixing the wash liquid may include operating a rotatable mixer disposed in the container. The rotatable mixer may be manually operable, such as by a handle attached to a rotating shaft disposed through a top of the container. The mixing may include manually (hand) manipulating such a handle to manually rotate the mixer within the container. In various preferred implementations, such mixing may be performed following addition of the wash liquid, and preferably shortly following such addition, to thoroughly mix the wash liquid and the adipose tissue being washed. Such a rotatable mixer may also be used to mix the digestion medium and the adipose tissue following addition of the digestion medium to the container, and preferably shortly after such addition, to thoroughly mix the digestion medium and washed adipose tissue to be digested.

The wash liquid used during the washing may but need not be of the same composition for each wash cycle. The wash liquid may include one or more additives. For example the wash liquid for one of more of the wash cycles may include one or more than one of an anti-clotting agent, an antibiotic and an antifungal. In some preferred implementations, for at least one wash cycle, the wash liquid includes at least one of an anti-clotting agent, an antibiotic or an antifungal. In other implementations, for at least one wash cycle, the wash liquid includes an anti-clotting agent, an antibiotic and an antifungal. One preferred example for an anti-clotting agent is heparin.

The adding of a stopping reagent to the container may be performed within a narrower time period than that described above. The stopping reagent may be added within a time period not later than 45 minutes following adding the volume of digestion medium, not more than 40 minutes following adding the volume of digestion medium or not more than 35 minutes following adding of the volume of digestion medium. The stopping reagent may comprise human albumin. The stopping medium may be added in an amount sufficient to substantially stop enzymatic activity within the container. The stopping reagent may preferably be added before the centrifuging of the container following the digesting.

The container may be conveniently transported between different locations for performance of different processing at the different locations, and preferably may be manually transported by being carried by a person. For example, the temperature controlled environment may be located at one location and the centrifuge may be located at a different location, and the method may comprise after the retention time in the temperature controlled environment, transporting the container from that location to the location of the centrifuge for performance of the centrifuging. As another example, one or more wash cycles may occur at yet a different location, and the method may comprise transporting the container from the location of a wash cycle to the location of the temperature controlled environment. By transporting the container from one location to another it is meant that the container, along with contents of the container, are physically moved from one location to the other location, whether or not there are intermediate stops along the way.

The container may have an access orientation, also referred to herein as a collection orientation, which may be a free-standing orientation. When the container is in the access orientation, all access into the container may in various implementations be through one or more ports extending through the top (e.g., through a lid) of the container and accessible from above the top of the container. Having all access into the container from above the container facilitates convenient addition and removal of materials from the container, without requiring special suspension or retention of the container and without access from the side that may be more susceptible to moving or tipping the container. When in the access orientation, the container may be supported by a base that maintains the container in a stable, free-standing condition.

The container may include volume gradation markings on an exterior side of the container, with the gradation markings indicating the quantity of volume occupied by a tissue retention volume (e.g., on a second side of the filter) within the container up to different elevations within the container, such as when the container is positioned an access orientation. The gradation markings permit direct visual measurement of the quantity of the volume of material (e.g., adipose tissue) disposed within the tissue retention volume. This makes it convenient for someone using the container to quickly identify the volume of tissue disposed within the tissue retention volume, and to quickly determine quantities of wash liquid or digestion medium to be added for washing or digesting operations. When the container includes such gradation markings, the wall of the container with the gradation markings preferably has sufficient transparency to permit visual observation of the level of tissue or other material disposed within the container.

The method permits convenient and controlled processing of significant quantities of adipose tissue in a convenient manner. The volume of adipose tissue (including contaminants), disposed in the container on the second side of the filter (e.g., within a filtrate volume) at commencement of the washing may be in a range having a lower limit of 50, 100, 150, 200 or 250 cubic centimeters and an upper limit of 700, 600, 500 or 400 cubic centimeters.

It should be appreciated that when reference is made to "adipose tissue" or a volume thereof in relation to a method of the invention the reference may be to in-tact adipose tissue and any associated contaminants that are present with the in-tact tissue. These contaminants come from the biological materials extracted from subjects to obtain the adipose tissue. Contaminants that may be associated with the adipose tissue include for example blood, free lipids, small particles and debris and other materials that may have been collected with the adipose tissue or result from degradation during tissue collection or processing operations. The amounts of these contaminants will generally be higher in unwashed adipose tissue at the commencement of washing operations and will generally be lower at the commencement of digesting operations, following the washing.

BRIEF DESCRIPTION OF THE DRAWINGS

FIG. 6 shows the same tissue collection and processing apparatus as shown in FIG. 5 during removal of material from the filtrate volume through an extraction port.

FIG. 7 shows a tissue collection and processing apparatus suspended by a handle and from which material is being removed from the filtrate volume through a suction tube inserted into a suction port.

FIGS. 17A and 17B illustrate a translatable conduit in a tissue collection and processing apparatus.

DETAILED DESCRIPTION OF PREFERRED EMBODIMENTS

Figure 1:
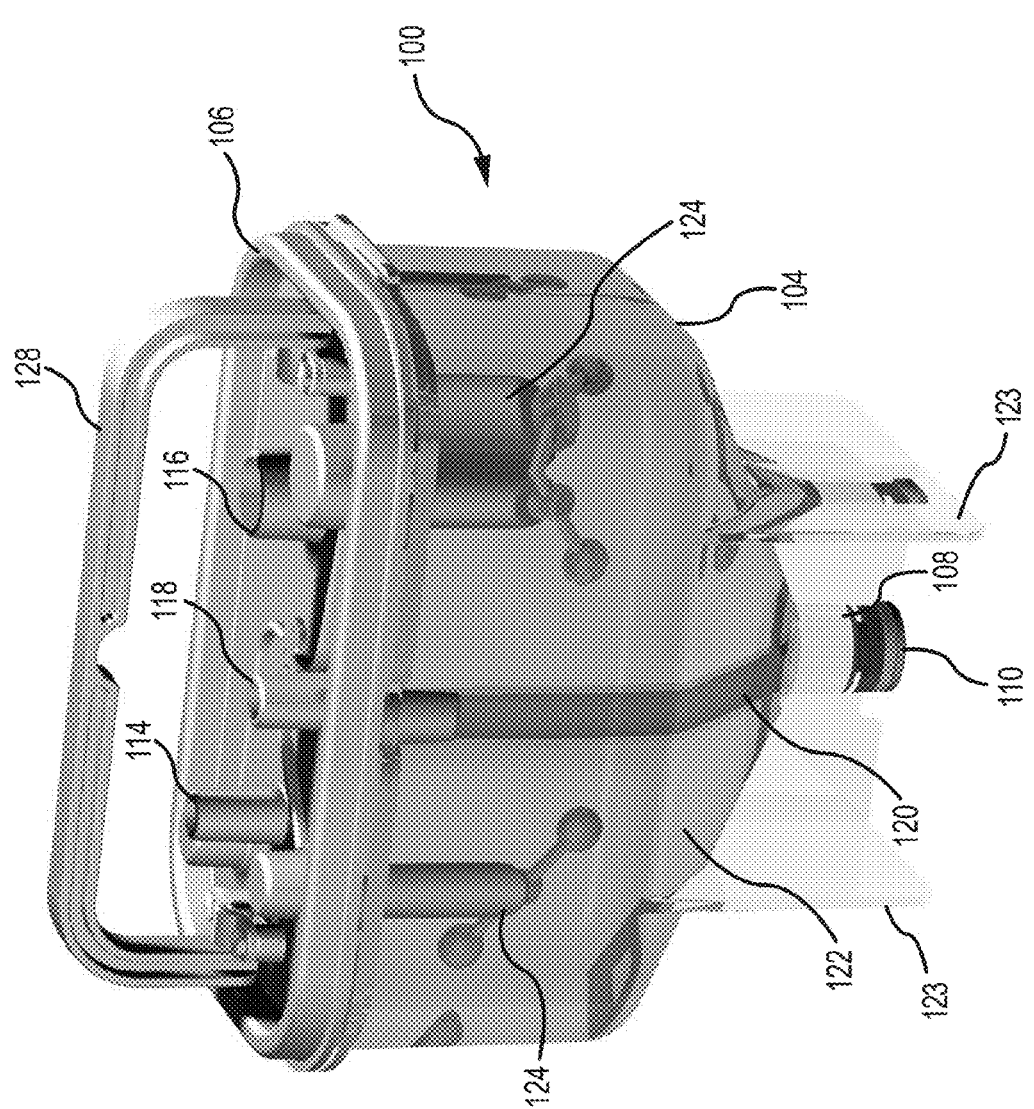
FIG. 1 shows in perspective a tissue collection and processing apparatus.
Figure 2:
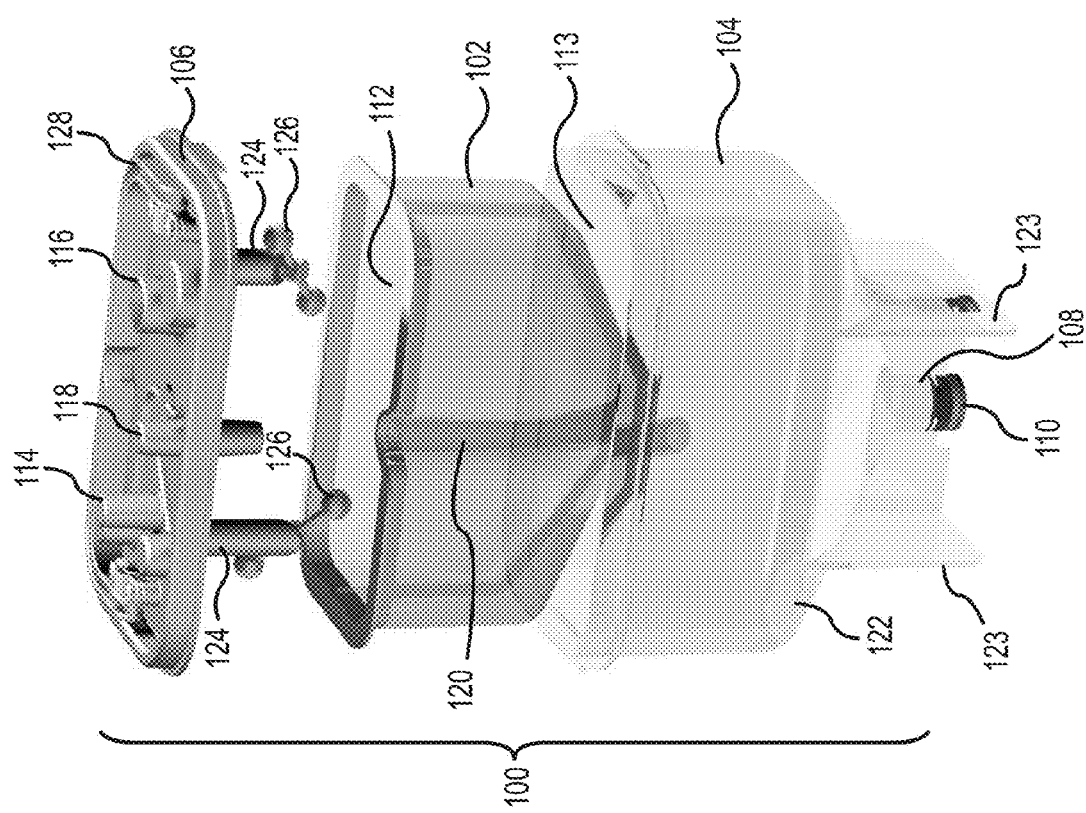
FIG. 2 shows the same tissue collection and processing apparatus as FIG. 1 with some component parts shown in exploded view.

FIG. 1 shows one embodiment of a tissue collection and processing apparatus, designated as apparatus 100. FIG. 2 shows the same apparatus 100 as in FIG. 1, but illustrated in an exploded view of some of the components. As shown in FIGS. 1 and 2, the apparatus 100 has a mesh bag filter 102 disposed within an internal containment volume of a container. The container is comprised of a rigid shell 104 and a rigid top 106. The top 106 is sealed to the top of the shell 104. The shell 104 may be made, for example, from a transparent plastic composition. The lid 106 may be made, for example, from a plastic composition. Disposed at the bottom of the shell 104 is a collection chamber 108 and an extraction port 110. The extraction port 110 comprises a sealing mechanism that is manipulable to extract material from inside the collection chamber 108. The sealing mechanism may, for example, comprise a silicon rubber septum or diaphragm that may be penetrable by a hypodermic needle to extract material, or may comprise a valve.

The mesh filter bag 102 divides and separates the internal containment volume of the container into a tissue retention volume 112 disposed inside the mesh filter bag 102, and a filtrate volume 113 disposed within the shell 104 on the outside of the mesh filter bag 102. The filtrate volume 113 is that portion of the internal containment volume into which filtrate enters after passing through the mesh filter bag 102 from the tissue retention volume 112.

An inlet port 114 in fluid communication with the tissue retention volume 112 through the top 106 is configured for introducing adipose tissue directly into the tissue retention volume during a lipoplasty procedure, such as for example through a tissue transport conduit that may be attached to the inlet port 114 to conduit tissue from a patient during such a procedure. An additional access port 116 in fluid communication through the top 106 with the tissue retention volume 112 provides an additional route for introducing material into or removing material from the tissue retention volume 112. A suction port 118 is in fluid communication through the top 106 with the filtrate volume 113 via a conduit 120 extending from the suction port 118 to the vicinity of the top of the collection chamber 108. The suction port 118 is configured for connection to a vacuum system, for example through connection of a suction conduit through which suction may be applied by a vacuum system to suction from the filtrate volume material passing through the mesh filter bag 102 from the tissue retention volume 112 into the filtrate volume 113. The shell 104 has a tapered wall portion 122 that defines a tapered portion of the internal containment volume, such that the cross-sectional area of the tapered portion of the internal containment volume tapers with a reducing cross-sectional area in a direction toward the collection chamber 108. By tapering, it means that the cross-sectional area in a horizontal plane (assuming the apparatus 100 is in an upright position as shown in FIG. 1) becomes smaller in a continuous manner in the direction of the taper (e.g., a direction orthogonal to the horizontal plane). The collection chamber 108 comprises a cylindrical volume located immediately below the tapered portion of the internal containment volume. The cross-sectional area of the internal containment volume at the bottom of the tapered portion 122 approaches that of the cross-sectional area of the collection chamber 108. "Collection chamber 108" is used to refer both to the downwardly extending cylindrically-walled portion of the shell body 104 and the cylindrical portion of the filtrate volume disposed therein.

The shell 104 includes a base portion 123 configured to support the apparatus 100 in the upright position as shown in FIG. 1, for example when the apparatus is resting on top of a hard flat surface, such as a table or shelf. For convenience, the side of the container adjacent the top 106 is referred to as the top side of the container and the side of the container adjacent the extraction port 110 is referred to as the bottom side of the container.

The apparatus 100 comprises mixers 124 that have agitator arms 126 that are rotatable to help mix contents within the internal containment volume, and in particular within the tissue retention volume 112. The mixers 124 may be driven by electrical power to rotate the agitator arms 126, which power may be supplied, for example, by an external electrical power source or by batteries disposed within the body of the mixers 124 or elsewhere in the apparatus 100.

The apparatus 100 includes a retractable handle 128 to facilitate suspending the apparatus 100 or for grasping and holding the apparatus 100 by hand. As shown in FIG. 1, the handle 128 is in an extended position for use to grasp or suspend the apparatus 100. FIG. 2 shows the handle 128 in a retracted position that is conveniently out of the way so that the handle 128 does not interfere with access to the inlet port 114, the access port 116 or the suction port 118 during use of the apparatus 100.

The apparatus 100 is designed to be portable, and is preferably portable by someone grasping the handle 128 and picking up the apparatus 100 by the handle 128 by hand, preferably by using a single hand, to facilitate ready transport of the apparatus 100, either while the internal containment volume is empty or with human tissue or components thereof disposed within the internal containment volume.

Figure 3:
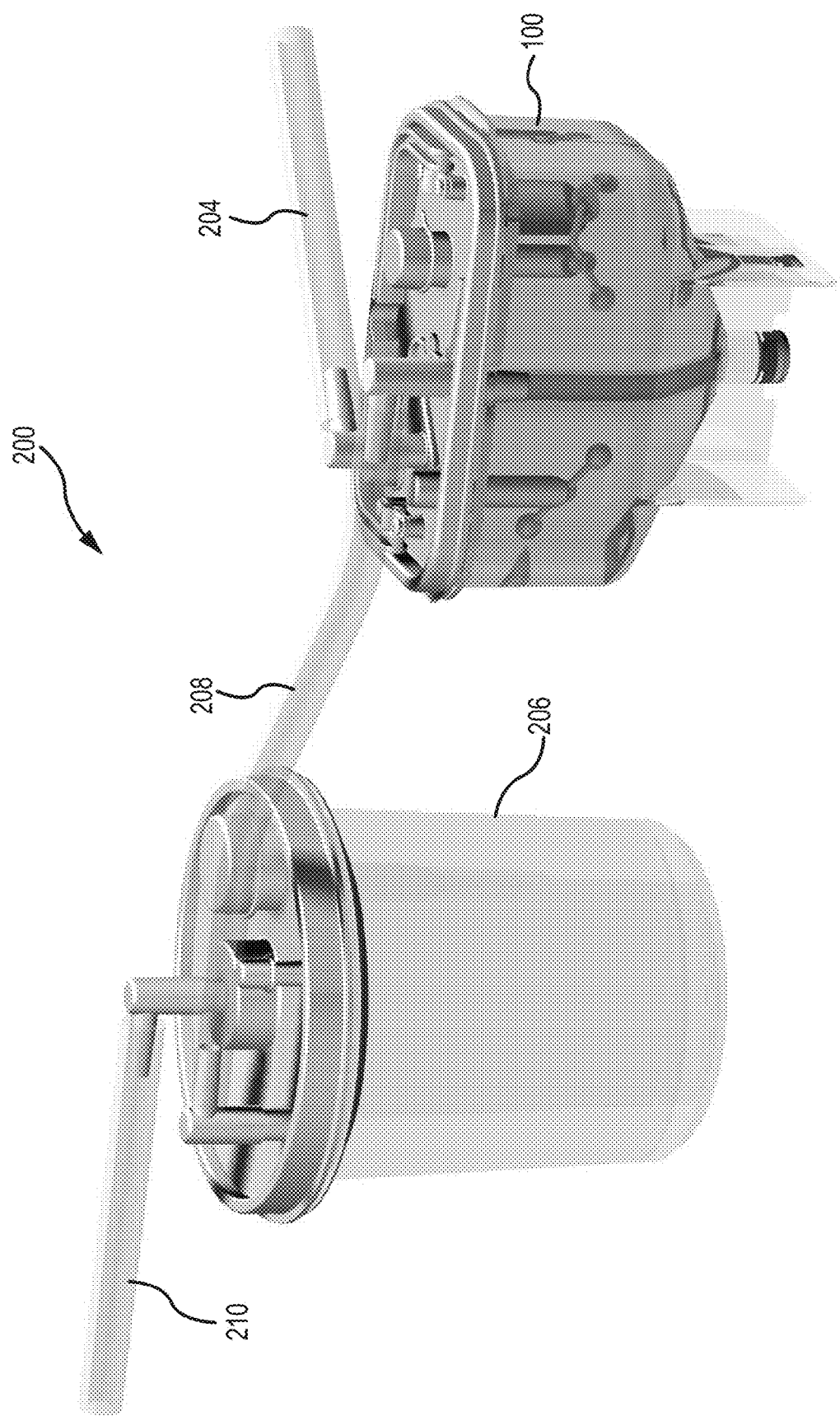
FIG. 3 shows in perspective a tissue collection and processing system.

Reference is now made to FIG. 3 showing a tissue collection and processing system 200 including the tissue collection and processing apparatus 100 of FIGS. 1 and 2 with an inlet port fluidly connected to a tissue conduit 204. A suction port of the apparatus 100 is fluidly connected with a canister 206 via a suction conduit 208. The canister 206 is fluidly connected with a vacuum system (not shown) through a conduit 210. For illustration purposes, the tissue collection and processing apparatus shown in FIG. 3 is the apparatus 100 of FIGS. 1 and 2. However any other design could be used in such a tissue collection and processing system, including any of the apparatus designs described below. During operation of the tissue collection and processing system 200, the tissue conduit 204 is conducting adipose tissue to the inlet port of the apparatus 100 for introduction of the adipose tissue into the tissue retention volume of the apparatus 100. Suction is applied to the filtrate volume within the apparatus 100 by the vacuum system through the conduit 210, the canister 206 and the suction conduit 208 to remove by suction from the filtrate volume material separating from the adipose tissue in the tissue retention volume of the apparatus 100 and passing through the filter and into the filtrate volume of the apparatus 100. Such material suctioned from the filtrate volume through the suction conduit 208 may then be collected in the canister 206. The canister 206 may be a waste canister and the collected material may be waste for appropriate disposal. For example, red blood cells may separate from adipose tissue during collection of the adipose tissue in the apparatus 100 and such red blood cells passing through the filter will be removed from the filtrate volume of the apparatus 100 by suction via the suction conduit 208.

In a method for processing tissue from a lipoplasty procedure, the tissue may be processed within a containment volume of a portable tissue collection and processing apparatus to prepare within the apparatus a concentrated product comprising at least one target component, or at least one target material, from the tissue. The apparatus has a filter and a container having an internal containment volume, wherein the internal containment volume comprises a tissue retention volume and a filtrate volume separated by the filter. The method may comprise: washing tissue in the containment volume with a wash liquid; after the washing, digesting tissue within the containment volume; and after the digestion, centrifuging the apparatus to prepare in the filtrate volume a concentrate product comprising at least one target component. For example the concentrate product may comprise, or may consist essentially of, stromal vascular fraction from adipose tissue, and a target component may be or comprise stem cells from adipose tissue. The method may also comprise one or more steps in addition to the washing, digesting and centrifuging. For example such an additional step may occur prior to the washing, between the washing and digesting, between the digesting and centrifuging or after the centrifuging.

During the washing, the wash liquid may be added to the containment volume to contact tissue within the tissue retention volume and with at least a portion, preferably a majority, and more preferably most, of the wash liquid passing through the filter into the filtrate volume. The wash liquid may wash one or more component from the tissue while retaining washed tissue in the tissue retention volume. The washed tissue may be retained in the tissue retention volume by the filter. Wash liquid passing into the filtrate volume may be removed from the filtrate volume, along with any component or components washed from the tissue. After adding the wash liquid, an optional step of centrifuging the apparatus may be performed. Such centrifuging may facilitate a high degree of separation of the wash liquid from the tissue retained in the tissue retention volume. Next, the wash liquid may be removed from the filtrate volume, for example by being suctioned through a suction port of the apparatus or by removal through an extraction port of the apparatus. The wash liquid may be an aqueous liquid, and may be or comprise a saline solution, for example a phosphate buffer solution. To ensure thorough washing of the tissue, the washing may include multiple wash stages, with each stage comprising adding wash liquid to the containment volume to contact tissue within the tissue retention volume and removing wash liquid from the filtrate volume.

During the digestion, an enzyme, such as for example collagenase, is added to the containment volume to contact at least a portion, preferably a majority of, and more preferably all or substantially all of the washed tissue, within the tissue retention volume. The enzyme should be of a type capable of breaking down at least a portion of the washed tissue to an extent to release a target component, or material, in a form capable of passing through the filter and into the filtrate volume. After adding the enzyme, the digesting may comprise agitating contents of the containment volume of the apparatus for a time and at a temperature sufficient for the digestion to proceed to an extent to significantly release the target component, or material, in the desired form capable of passing through the filter. The agitating may involve any method to agitate contents of the containment volume, including for example one or both of: (a) shaking the apparatus to agitate the contents within the apparatus and (b) mixing the contents within the apparatus, such as with one or more mixing device disposed within the containment volume and preferably disposed within the tissue retention volume. Shaking the apparatus may be accomplished by mounting the apparatus on a shaker, and preferably a warmer-shaker with a temperature control feature so that the apparatus and its contents may be maintained at a controlled temperature, such as at or approximately at human body temperature.

Post-digestion centrifuging promotes separation of the target component from the digested tissue and passage of the target component through the filter for collection in the filtrate volume, such as for example to collect within a collection chamber at the bottom of the apparatus, for example a collection chamber such as shown in FIG. 1 or FIG. 2. The centrifuging causes a concentrate product to collect in the filtrate volume, and preferably in such a collection chamber. Multiple material phases may collect within the filtrate volume, one or more of which or one or more portions of which, may comprise the desired concentrate product containing a target component. For example, a desired concentrate product may be higher-density pellet phase that is enriched in leuko stromal vascular cells, and which may be disposed near the bottom of the internal containment volume with multiple lower-density material phases disposed above the pellet in the internal containment volume. Such a higher-density pellet is also referred to herein as a stromal vascular fraction pellet.

Before the washing, the method may comprise collecting the tissue in the internal containment volume of the apparatus. The collecting may comprise conducting adipose tissue removed from a patient during a lipoplasty procedure into the tissue retention volume through a tissue conduit fluidly connected with the apparatus during the lipoplasty procedure. Such collection may be performed, for example, using a tissue collection and processing system such as shown in FIG. 3. During the collecting, fluid separating from the adipose tissue and passing through the filter into the filtrate volume may be immediately removed from the filtrate volume by suctioning the fluid from the filtrate volume and out of the apparatus, for example to a collection canister such as that shown in FIG. 3.

The method may comprise, after the centrifuging, removing the concentrate product from the filtrate volume of the apparatus. The concentrate product may, for example, be removed from an apparatus such as those illustrated in FIGS. 1 and 2 from the collection chamber at the bottom of the filtrate volume through the extraction port with manipulation of the sealing mechanism. During the removing, the concentrate product may be removed to and collected in the barrel of a syringe, or in the barrels of multiple syringes. The removing may include selectively removing the concentrate product from the filtrate volume, to isolate the concentrate product from other material that may have collected in the filtrate volume during the centrifuging. To assist removing the concentrate product, the concentrate product may be diluted with a dilution liquid to put the concentrated product in a dilute form that is easier to remove from the filtrate volume. The dilution liquid is used to suspend material of the stromal vascular fraction pellet, and may alternatively be referred to a suspension liquid or re-suspension liquid. The dilution liquid may be an aqueous liquid. The dilution liquid may be a saline solution, for example a phosphate buffer solution. Such dilution of the concentrate product may be particularly useful in the situation where the concentrate product collects in the form of a relatively hard pellet in the filtrate volume, which may be the case for collection of stromal vascular fraction from adipose tissue. Selective removal of the concentrate product may include separating a material phase comprising the concentrate product from one or more other material phase that collects in the filtrate volume. For example, a stromal vascular fraction may be a middle density phase, with a more dense phase and a less dense phase disposed on either side of the stromal vascular fraction. The more dense phase, which may collect at the bottom of a collection chamber in the apparatus, may be rich in red blood cells. Selective removal of the stromal vascular fraction may include first removing this red blood cell phase from the collection chamber (e.g., into a syringe) and then removing the stromal vascular fraction from the collection chamber (e.g., into a different syringe). However, with thorough initial washing of tissue, such a layer rich in red blood cells may be kept sufficiently small in size that it need not be removed separately from the stromal vascular fraction pallet, and may be removed with the dilution liquid together with the stromal vascular fraction.

The apparatus used with the method for processing tissue is portable. The method may include transporting the apparatus, and tissue contained therein, between locations where different processing procedures are performed. For example, the apparatus may be located at one location where collecting tissue is performed, while the washing and/or digesting may be performed at a different location. In one implementation, the containment volume comprising tissue may be sealed following one procedure and the apparatus with the sealed containment volume may be transported to a different location for performance of a subsequent procedure. For example, with the apparatus 100 shown in FIGS. 1 and 2, the apparatus may be sealed by capping the inlet port 114, access port 116 and suction port 118 with sealing caps.

To further illustrate various features of the method for processing tissue, and apparatus, assemblies and systems that may be used during the method, reference is now made to FIGS. 4-10.

Figure 4:
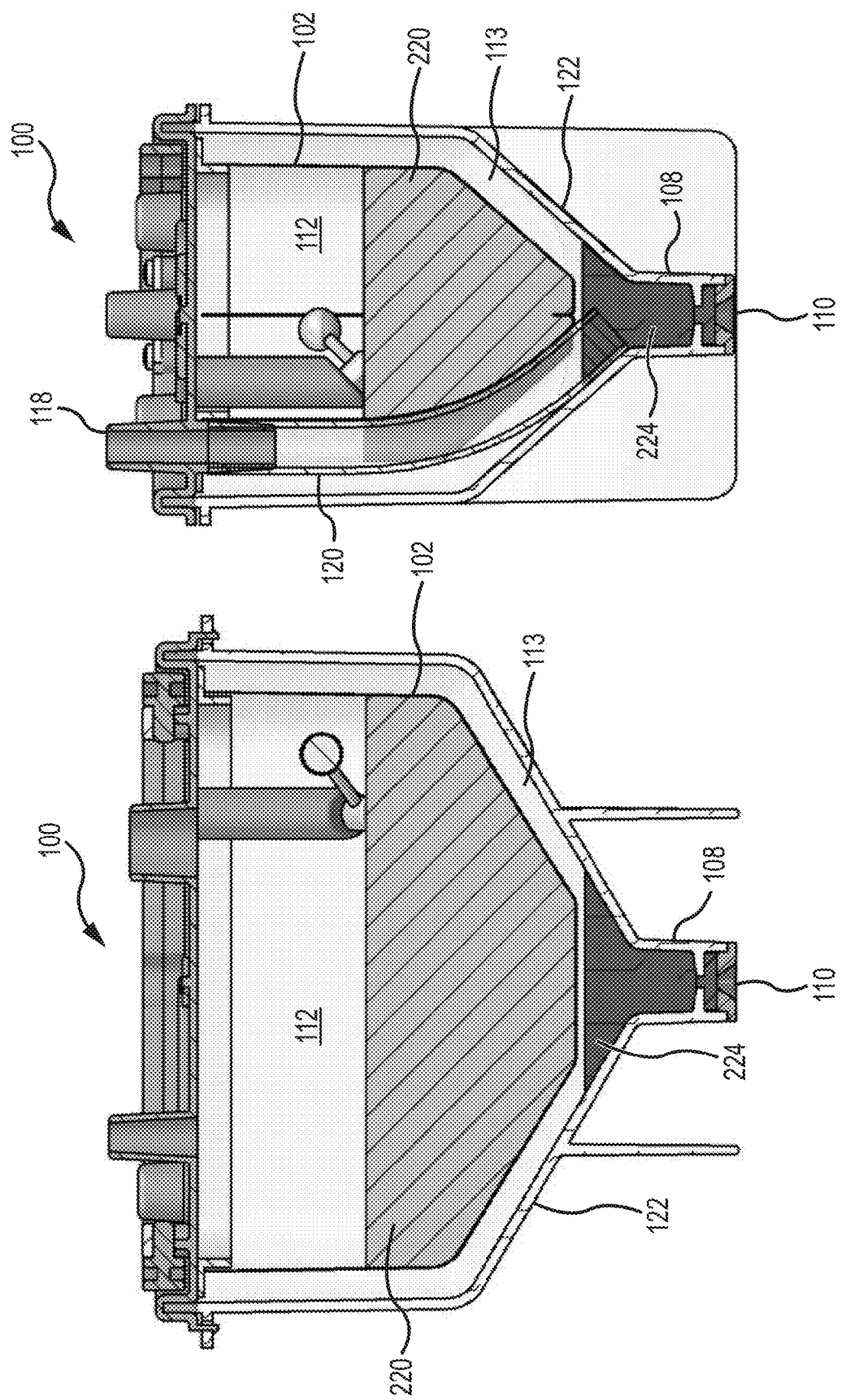
FIG. 4 shows side and end sectional views of a tissue collection and processing apparatus having collected tissue disposed therein.

FIG. 4 shows the apparatus 100 (of FIGS. 1 and 2) during a tissue collecting operation. During tissue collection, adipose tissue from a lipoplasty procedure, which may be referred to as lipoasperate, is received in the tissue retention volume 112 or 148. FIG. 4 shows material 224 that separate from lipoasperate, pass through the filter 102 and collect in the filtrate volume 113, while tissue 220 (mostly adipose tissue with some containments) is retained in the respective tissue retention volume 112. The material 224 collecting in the filtrate volume 113 may be continuously or intermittently removed from the filtrate volume 113 by suction through the suction port 118 and the conduit 120.

Figure 5:
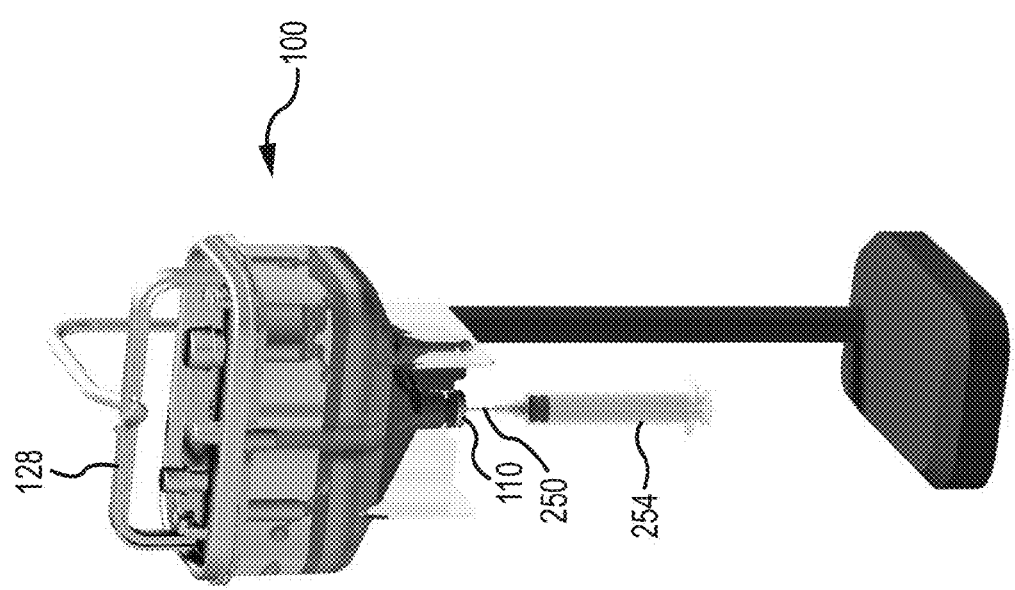
FIG. 5 shows a tissue collection and processing apparatus suspended by a handle and from which material is being removed from the filtrate volume through an extraction port.

FIGS. 5 and 6 show the apparatus 100 of FIGS. 1 and 2 suspended by the handle 128 following optional centrifuging of a washing operation and prior to digesting with a hypodermic needle 250 inserted through a sealing mechanism 252 in the extraction port 110 for removal of infranatant (e.g., dirty wash liquid) from the filtrate volume 113 and into the barrel of a syringe 254.

FIG. 7 shows the apparatus 100 of Design A following optional centrifuging of a washing operation and prior to digestion, in which infranatant (e.g., dirty wash liquid) is being removed from the filtrate volume 113 via a suction tube 260 inserted through the suction port 118 and the conduit 120 into the filtrate volume 113, with the material removed from the filtrate volume 113 being collected within the barrel of a syringe 262.

Figure 8:
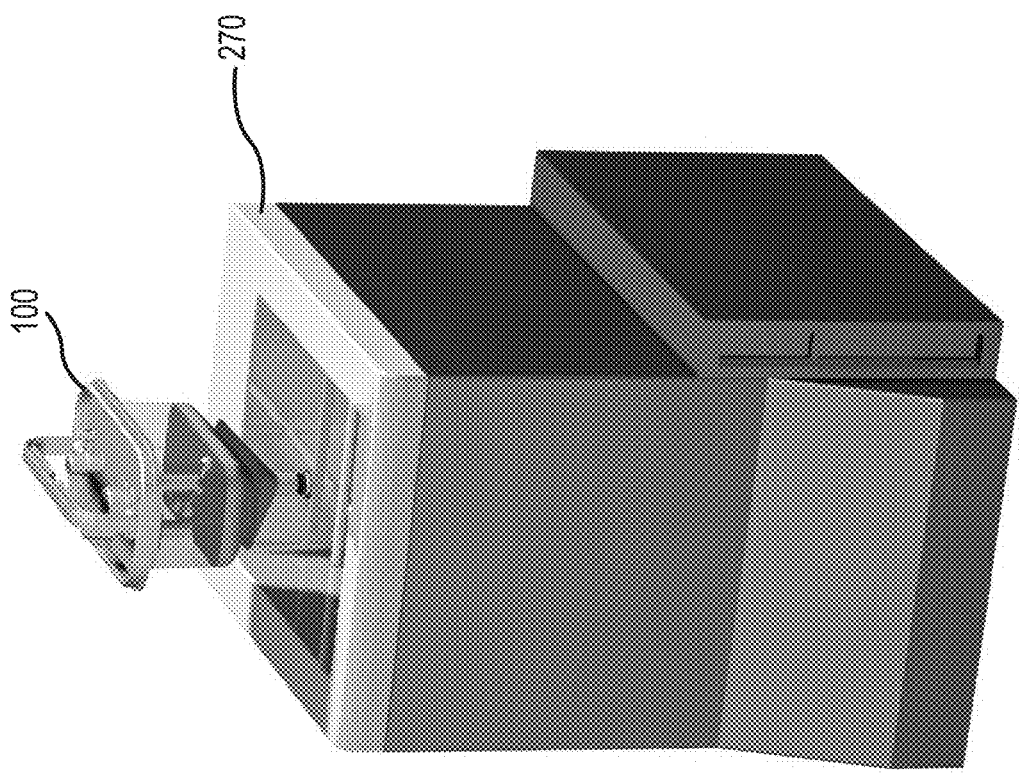
FIG. 8 shows a tissue collection and processing apparatus being mounted on a warmer-shaker.
Figure 9:
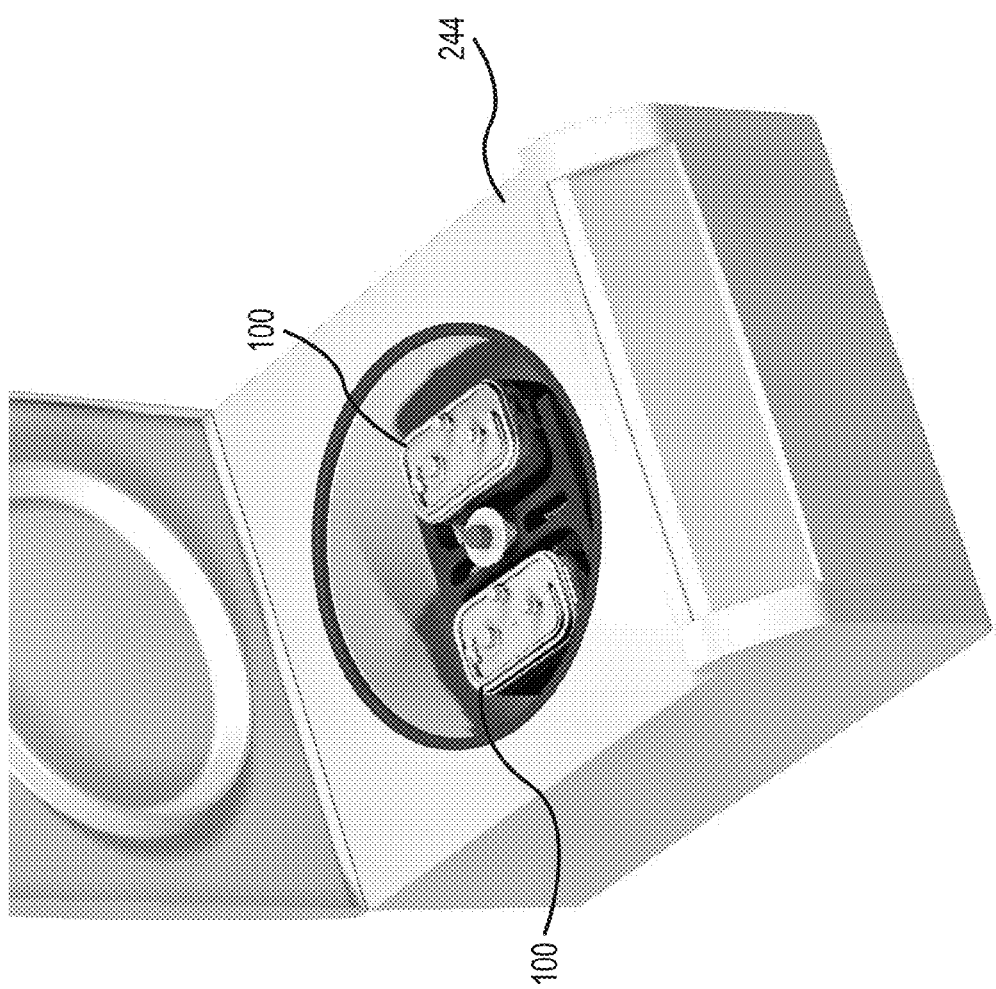
FIG. 9 shows a centrifuge with two tissue collection and processing apparatus received therein for centrifuge processing.

FIG. 8 shows the apparatus 100 (FIGS. 1 and 2) being mounted on a warmer-shaker 270 for controlled temperature agitation of the contents of the apparatus 100, such as may be performed during a digestion operation after adding an enzyme to the internal containment volume. The mixers 124 (FIGS. 1 and 2) within the internal containment volume may optionally be operated during the shaking operation to assist agitation in addition to the shaking provided by the warmer-shaker 270. In any event, contents of the apparatus 100 may be agitated by the shaking motion of the warmer-shaker FIG. 9 shows two of the apparatus 100 (of FIGS. 1 and 2) received in a centrifuge 244 for centrifuging, as may be optionally performed during a washing operation or as may be performed during the centrifuging following digestion.

Figure 10:
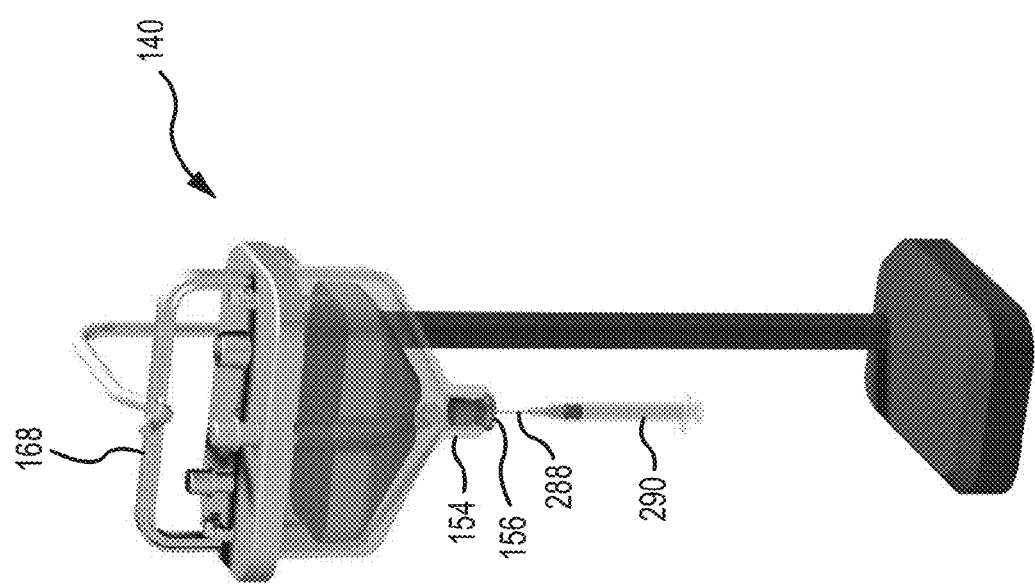
FIG. 10 shows a tissue collection and processing apparatus suspended by a handle and from which material is being removed from a collection chamber through an extraction port.

FIG. 10 shows a tissue collection and processing apparatus 140 suspended from the handle 168 and with a concentrate product being selectively removed from collection chamber 154 through a sealing mechanism in an extraction port 156 through a hypodermic needle 288 into the barrel of a syringe 290. For example, the concentrate product being selectively removed as shown in FIG. 10 may be a stromal vascular fraction from adipose tissue.

Figure 11:
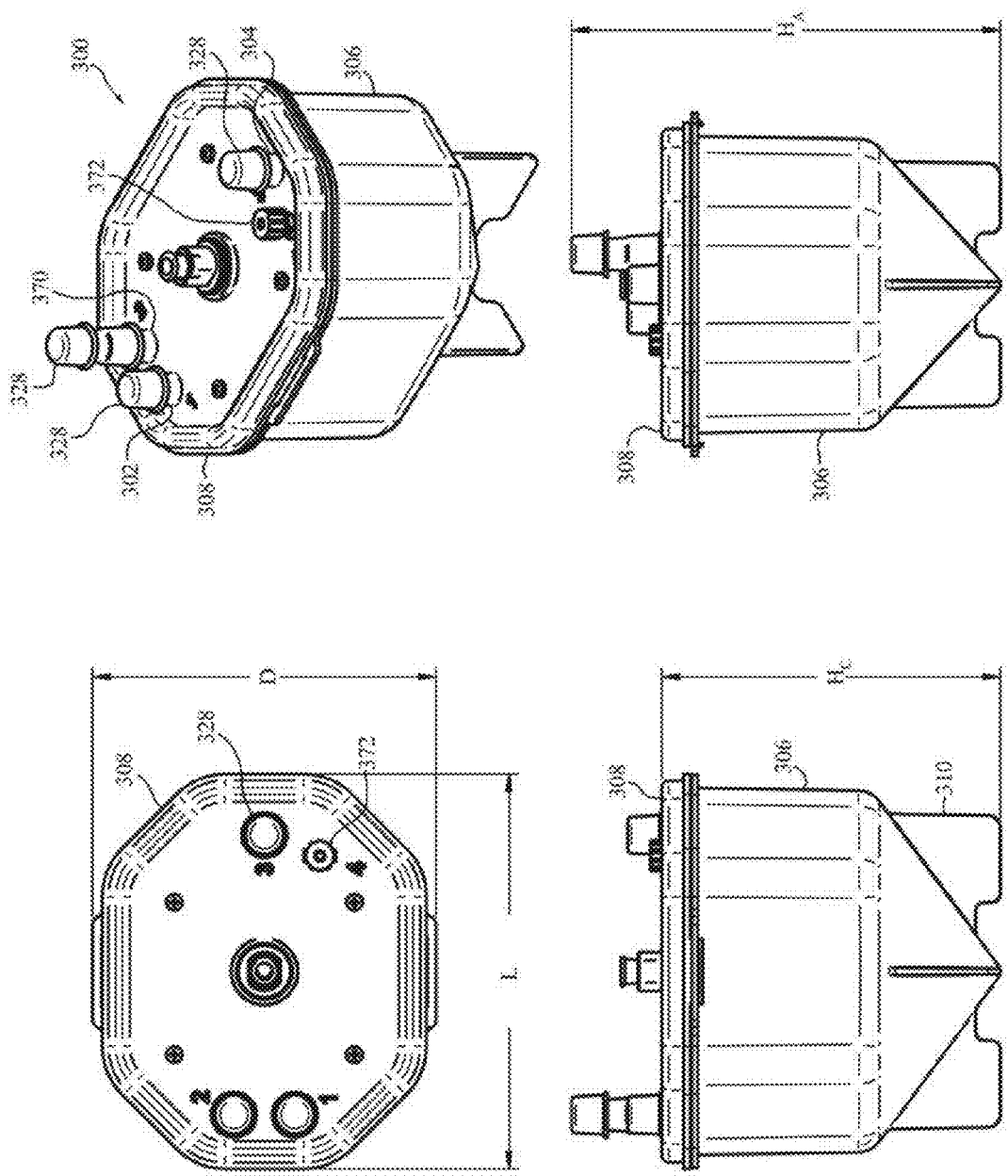
FIG. 11 shows top, perspective, side and end views of another embodiment of a tissue collection and processing apparatus.

FIG. 11 shows an apparatus 300 for collection of tissue comprising adipose removed from a patient during a lipoplasty procedure and for post-collection processing of collected tissue. The apparatus 300 is illustrated in a collection orientation. The collection orientation is the orientation in which the apparatus 300 may be placed during the collection of adipose removed from a patient during a lipoplasty procedure. The apparatus 300 may also be placed in the collection orientation during stages of the post-collection processing of collected tissue as described below. Accordingly, subsequent references herein to the orientation of the apparatus 300, such as top, bottom, lower and upper, will refer to the collection orientation of FIG. 11. As illustrated, the apparatus 300 has an apparatus height $H_A$, an apparatus length L, and an apparatus depth (or width) D. The apparatus 300 also includes a suction port 302 and an inlet port 304. The suction port 302 and inlet port 304 are disposed on the top of the apparatus 300 when the apparatus 300 is in the collection orientation as illustrated in FIG. 11. In FIG. 11, and in certain other subsequent figures, the ports are illustrated as having caps 328 thereon. Such caps 328 are used to cover the various ports and may be removed and replaced as necessary during use of the apparatus 300.

The apparatus 300 includes a shell 306 and a lid 308. The shell 306 is a unitary bowl-like member where the only access into the interior, or cavity of the shell 306 is through the opening at the top of the shell 306. As illustrated in FIG. 11, this opening at the top of the shell 306 may be covered by the lid 308. The lid 308 and shell 306 may be rigid. The lid 308 and shell 306 are each preferably made of a clear polymeric material, such as a clarified polypropylene polymer composition, which provides low cellular adhesion and reasonable clarity. The lid 308 and shell 306 may be fabricated by injection molding. The lid 308 may be attached to the shell 306 in any appropriate manner, including snapping, clamping and/or gluing onto the shell 306. Together, the shell 306 and lid 308 form a container 322 with an internal containment volume 330 (see FIG. 15 and accompanying discussion below) within the apparatus 300. The internal containment volume 330 is the volume within the cavity of the shell 306 covered by the lid 308, and is the volume available for disposing both hardware and material to be processed in the container 322. This container 322 may have a container height Hc. The shell 306 may include a set of integral base supports 310 that may support the apparatus 300 in the collection orientation when the apparatus 300 is placed on a horizontal surface. The apparatus height $H_A$ is larger than the container height Hc by the distance of projections above the top of the container 322 for the inlet port 304, suction port 302, caps 328 and other upward projecting features described below. The shell 306 may be conveniently designed to efficiently fit within a centrifuge bucket. The projections above the container height Hc may be configured so as not to interfere with operation of such a centrifuge. As seen in FIG. 11, the apparatus length L is equal to the container length and the apparatus depth is equal to the container depth (or width). As will be appreciated, the corresponding height, length and depth dimensions of the internal containment volume 330 will equal the height, length and depth dimensions of the container 322 less the corresponding thicknesses of walls of the shell 306 and lid 308. As shown in FIG. 11, some features may be integrally formed with the lid 308. For example as shown in FIG. 11 the suction port 302 and the inlet port 304 are integrally formed as a unitary fabricated piece with the lid 308. It should be appreciated that such features may be provided as separate pieces and then assembled, such as by gluing or other means. For structural integrity, fabrication as a unitary piece is generally preferred.

Figure 12:
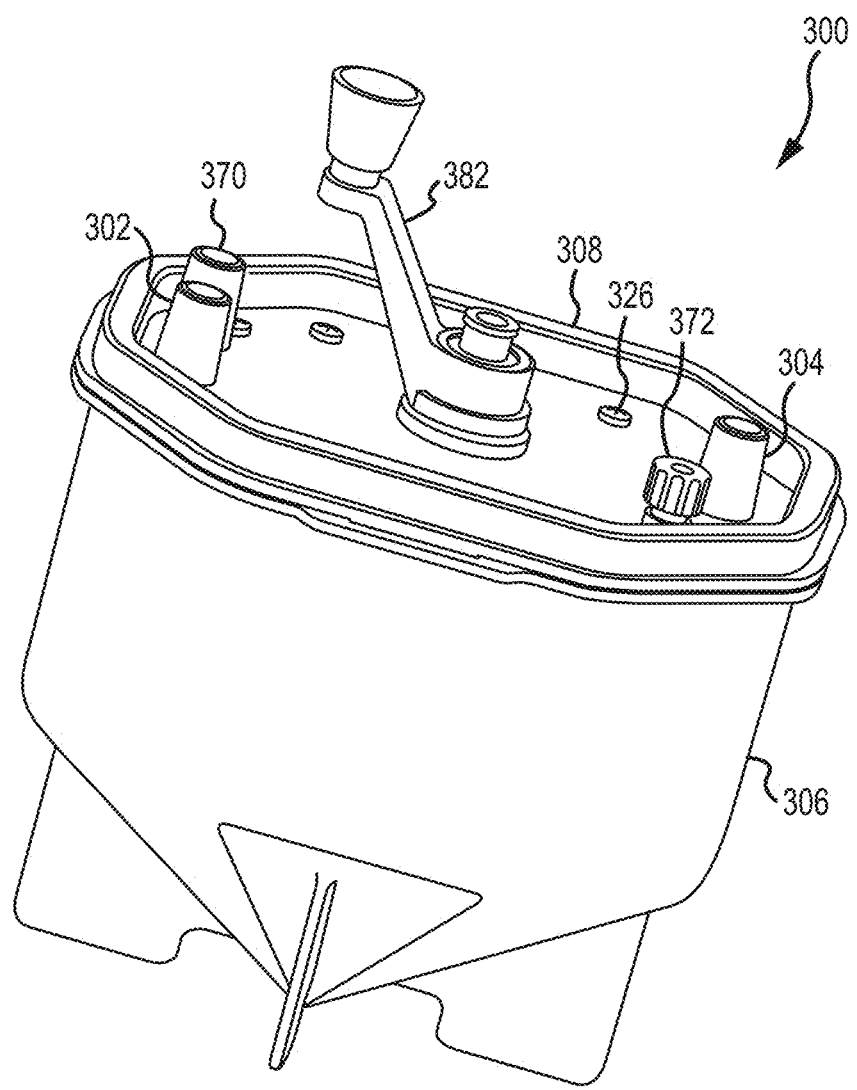
FIG. 12 shows another perspective view of the same tissue collection and processing apparatus as FIG. 11.
Figure 13:
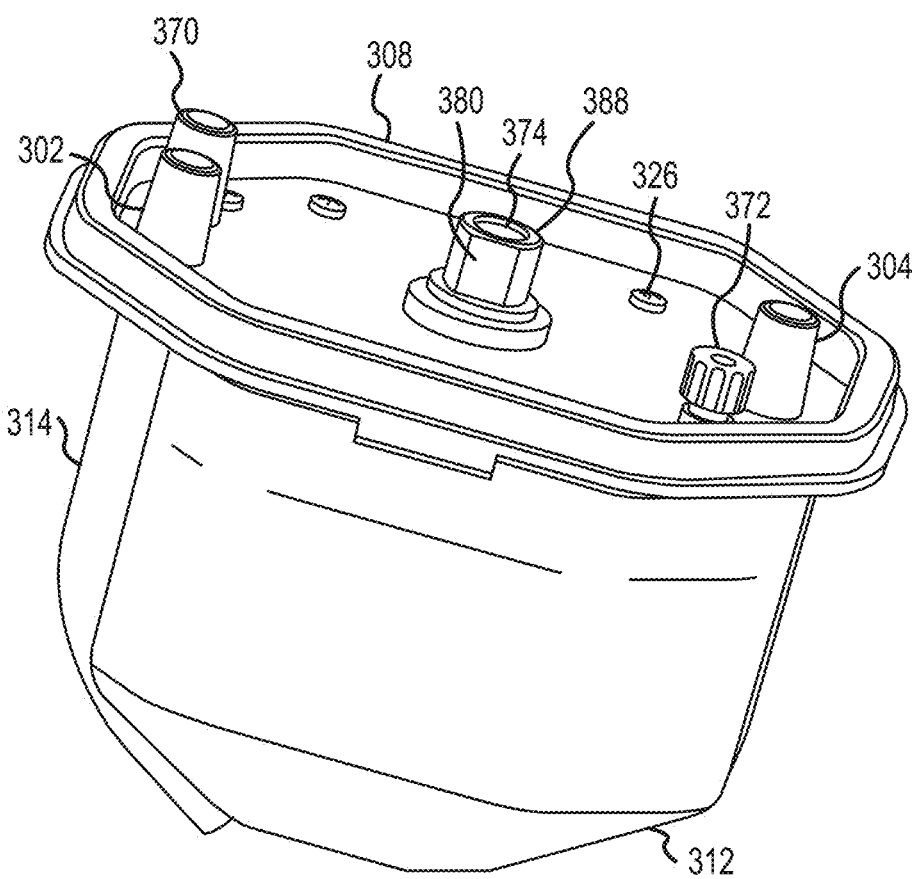
FIG. 13 shows the same tissue collection and processing apparatus as FIG. 12 with a shell removed.

FIG. 12 shows another perspective view of the apparatus 300 with the caps 328 to ports removed and with an installed handle 382. FIG. 13 shows the apparatus 300 in the same orientation as in FIG. 12 with the shell 306 and handle 382 removed. With the shell 306 removed, a filter 312 can be seen that is disposed within the internal containment volume 330. The filter 312 may have a separation size in a range, for example, from 70 microns to 800 microns. The filter is preferably made of a mesh material. The preferred mesh material is a nylon mesh. Also visible within the internal containment volume 330 is a suction port conduit 314 extending downward from the suction port 302. Additionally, as illustrated in FIG. 13, all components of the apparatus 300, except for the shell 306, are interconnected to the lid 308. In this regard, the subassembly shown in FIG. 13 may be assembled as shown and inserted into the shell 306.

Figure 14:
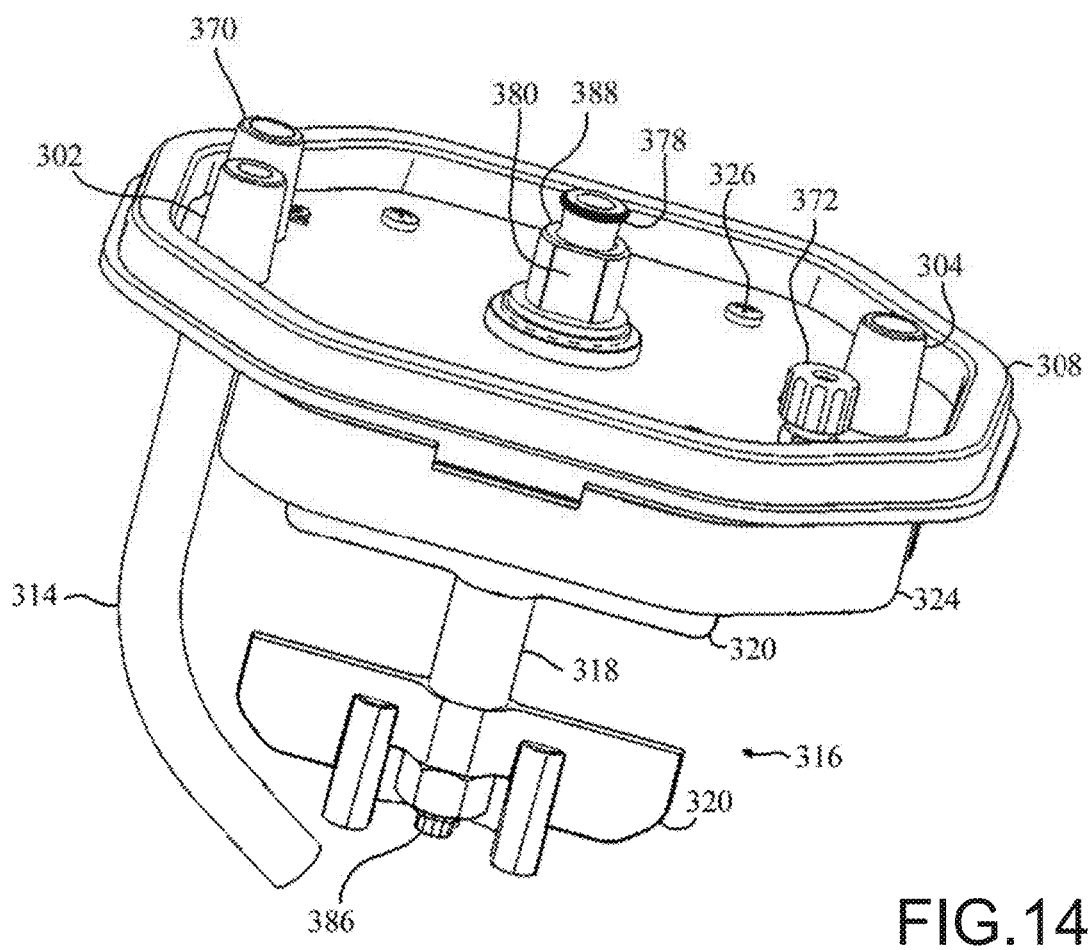
FIG. 14 shows the same tissue collection and processing apparatus as FIG. 13 with a filter removed.

FIG. 14 shows another perspective view of a portion of the apparatus 300 in the same orientation as in FIG. 13 with both the shell 306 and the filter 312 removed. With the filter 312 removed, a flow barrier skirt 324 extending downward from the lid 308 into the internal containment volume 330 is visible. In an example, the flow barrier skirt 324 may extend between 5 mm and 50 mm downward from the lid 308. The flow barrier skirt 324 may serve as an attachment point for the filter 308 such that the filter 312 may be fixed relative to the lid 308. The flow barrier skirt 324 may also serve to prevent material from entering a tissue retention volume 332 (described below) and immediately moving through the filter 312 into the filtrate volume 334. The tissue retention volume 332 is that portion of the internal containment volume 330 contained within the filter 312 and barrier skirt 324 below the lid 308. The filtrate volume 334 is that portion of the internal containment volume 330 disposed outside of the filter 312 and barrier skirt 324. With the flow barrier skirt 324 in place, and material entering the inlet port 304 must at least move to below the lowest level of the flow barrier skirt 324 before it is able to pass through the filter 312 into the filtrate volume 334. The flow barrier skirt 324 may be part of a filter subassembly that includes the flow barrier skirt 324 and the filter 312. This subassembly is mounted to the lid 308 with four screws 326.

The filter 312 is asymmetric with respect to the lid 308 and shell 306 in that it is configured to provide clearance between its left side (as viewed in FIG. 13) and the shell 306 for the suction port 302 and suction port conduit 314. A portion of the filter 312 may be disposed about (e.g., rest on or around) a portion of the suction port conduit 314.

With the filter 312 removed (FIG. 14), a mixing device 316 can be seen. The mixing device 316 includes a rotatable shaft 318 and a set of mixing members 320. The axis of rotation of the rotatable shaft 318 may be through a central axis of the rotatable shaft 318. The mixing members 320 are in the form of paddles extending outward from the rotatable shaft 318. Accordingly, when the rotatable shaft 318 is rotated, the mixing members 320 will be rotated through the materials within the tissue retention volume 332 to aid in mixing the materials within the internal containment volume 330, and in particular within the tissue retention volume 332. The rotatable shaft 318 extends from outside of the internal containment volume 330 through the lid 308 to the inside of the internal containment volume 330. As the rotatable shaft 318 is rotatable relative to the lid 308, the mixing members 320 fixed to the rotatable shaft 318 are also rotatable relative to the lid 308. The rotatable shaft 318 may be made from a metal composition, such as stainless steel (e.g., grade 303, 304, or 316). Alternatively, the rotatable shaft 318 may be made from a high-strength polymer composition such as an Ultem™ resin product.

The rotatable shaft 318 may include a handle interface 380 (FIG. 13) that may provide an interface for the handle 382 (FIG. 12) to be interconnected to the portion of the rotatable shaft 318 outside of the internal containment volume 330. The handle interface 380 of FIG. 13 is in the form of a pair of parallel surfaces disposed about the portion of the rotatable shaft 318 outside of the internal containment volume 330. The handle 382 has a mating pair of interior parallel surfaces configured such that when the handle 382 is placed over the handle interface 380, turning the handle 382 will result in turning the rotatable shaft 318 and the mixing device 316. Such an interface 380 also allows for the handle 382 to be removed and replaced on the handle interface 380 as needed during use of the apparatus 300.

Figure 15:
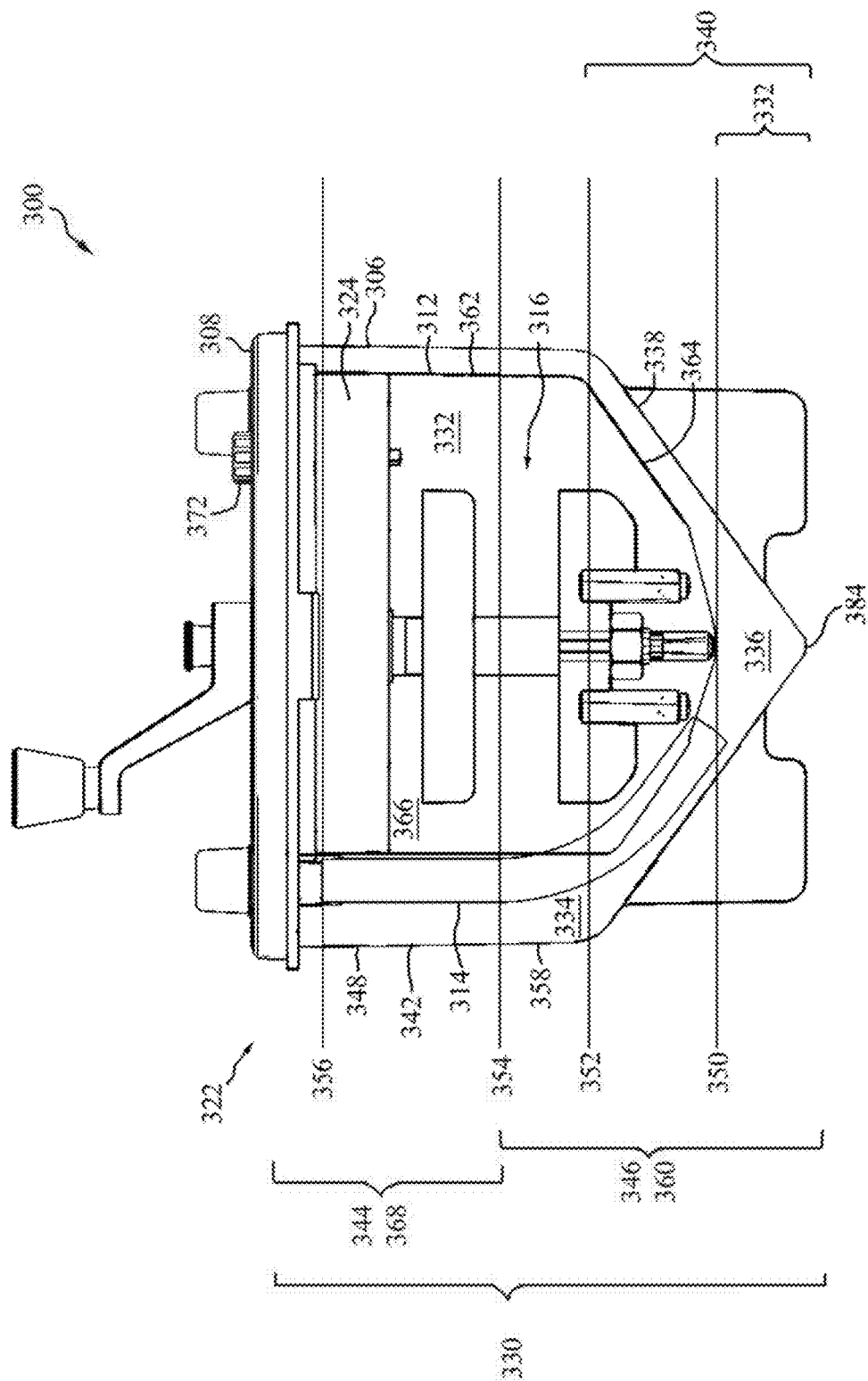
FIG. 15 illustrates various regions within the tissue collection and processing apparatus of FIG. 12.

FIG. 15 is a side schematic view of the apparatus 300 showing the mixing device 316 and filter 312 within the shell 306. The internal containment volume 330 is the entire volume within the shell 306 and under the lid 308. Together, the portions of the shell 306 and lid 308 that contain the internal containment volume 330 are a container 322 of the apparatus 300. The filter 312 divides and separates the internal containment volume 330 of the container 322 into the tissue retention volume 332 disposed inside the filter 312, and a filtrate volume 334 disposed within the shell 306 on the outside of the filter 312. The filtrate volume 334 is that portion of the internal containment volume 330 into which filtrate enters after passing through the filter 312 from the tissue retention volume 332.

Disposed within the internal containment volume 330 at the bottom of the shell 306, below a level 350 that is at or below the lowest extent of the filter 312 (and therefore also below the lowest extent of the tissue retention volume 332), is a collection volume 336, such that the collection volume 336 is part of the filtrate volume 334 and occupies the lowermost portion of the filtrate volume 334 located below the lowest elevation of the tissue retention volume 332.

The shell 306 has a tapered wall portion 338 that defines a tapered portion 340 of the internal containment volume 330, such that the cross-sectional area of the tapered portion 340 of the internal containment volume 330 tapers with a reducing cross-sectional area in a direction toward bottom of the container 322. By tapering, it means that the cross-sectional area in a horizontal plane (assuming the apparatus 300 is in the collection orientation) becomes smaller in the direction of the taper (e.g., a direction orthogonal to the horizontal plane). The tapered portion 340 of the internal containment volume 330 occupies the portion of the internal containment volume 330 below a level 352 where the tapered wall portion 338 meets a straight wall portion 342 of the shell 306. The tapered wall portion 338 is shown as having a flat, uniform inclined wall surface. The incline angle of surfaces of the tapered wall portion need not be uniform from the top to the bottom of the tapered portion 340 of the internal containment volume 330, and may vary from top to bottom with portions having different incline angles, and may have a curved surface, provided that the cross-section area is reducing in the direction of the taper. Also, the tapered wall portion 338 need not be uniform around the perimeter of the tapered portion 340 of the internal containment volume 330. For example, in the embodiment in FIGS. 13-15, the tapered wall portion 338 has a steeper incline on the ends than on the front or back of the apparatus 300.

The shell 306 may comprise an upper portion 344 generally above a level 354 and having a first wall surface portion 348 defining a corresponding upper portion 368 of the internal containment volume 330. Substantially all of the first wall surface portion 348 may have an incline relative to horizontal of at least 75°. For example, substantially all of the first wall surface portion 348 may be substantially vertical (90° incline relative to horizontal). The shell 306 may include a lower portion 346 located below the upper portion 344 and having a second wall surface portion 358 defining a corresponding lower portion 360 of the internal containment volume 330. The lower portion 360 may include the tapered wall portion 338 defining the tapered portion 340 of the internal containment volume 330. Substantially all of the tapered wall portion 338 may preferably have an incline relative to horizontal in a range of from 30° to 60°, although other angles or curved surfaces may be used. The tapered portion 340 of the internal containment volume 330 may occupy substantially the entire lower portion 360 of the internal containment volume 330. At least a first portion 362 of the filter 312 may be disposed in the upper portion 368 of the internal containment volume 330 and a second portion 364 of the filter 312 may be disposed in the lower portion 360 of the internal containment volume 330. The tapered wall portion 338 may form a nadir 384 at its lowest elevation. The nadir 384 may also be a nadir of the collection volume 336, the filtrate volume 334, the container 322, and the internal containment volume 330.

The internal containment volume 330 may include an available processing volume or "useable" volume 366 which may be the portion of the internal containment volume 330 that is usable and/or may normally be occupied by materials within the container 322 during normal use. For example, the available processing volume 366 may be the portion of the internal containment volume 330 below a level 356 that coincides with the bottom extension of a port through the lid 308 (such as a second suction port 370 discussed below, see FIG. 11) and that is not occupied by portions (e.g., internal hardware) of the apparatus 300 within the internal containment volume 330, such as the mixing device 316, barrier skirt 324, filter 312 and suction port conduit 314. The top of the available processing volume may be at the elevation of the bottom extension of the inlet port 304, which may define a maximum fill level within the internal containment volume 330.

The inlet port 304 in fluid communication with the tissue retention volume 332 through the lid 308 is configured for introducing tissue comprising adipose directly into the tissue retention volume 332 during a lipoplasty procedure. However, use of the apparatus 300 is not so limited, and the tissue may be introduced into the apparatus using tissue previously collected in another container and transferred to the apparatus 300. An additional access port 372 in fluid communication through the lid 308 with the tissue retention volume 332 provides an additional route into the tissue retention volume 332, for example for introduction of additives.

The suction port 302 is in fluid communication through the lid 308 with the filtrate volume 334 via suction port conduit 314 extending from the suction port 302 to within the tapered portion 340 of the internal containment volume 330 in the vicinity of the top of the collection volume 336. The suction port 302 is configured for connection to a vacuum system, for example through connection of a suction conduit through which suction may be applied by a vacuum system to suction from the filtrate volume 334 material passing through the filter 312 from the tissue retention volume 332 into the filtrate volume 334.

Figure 28:
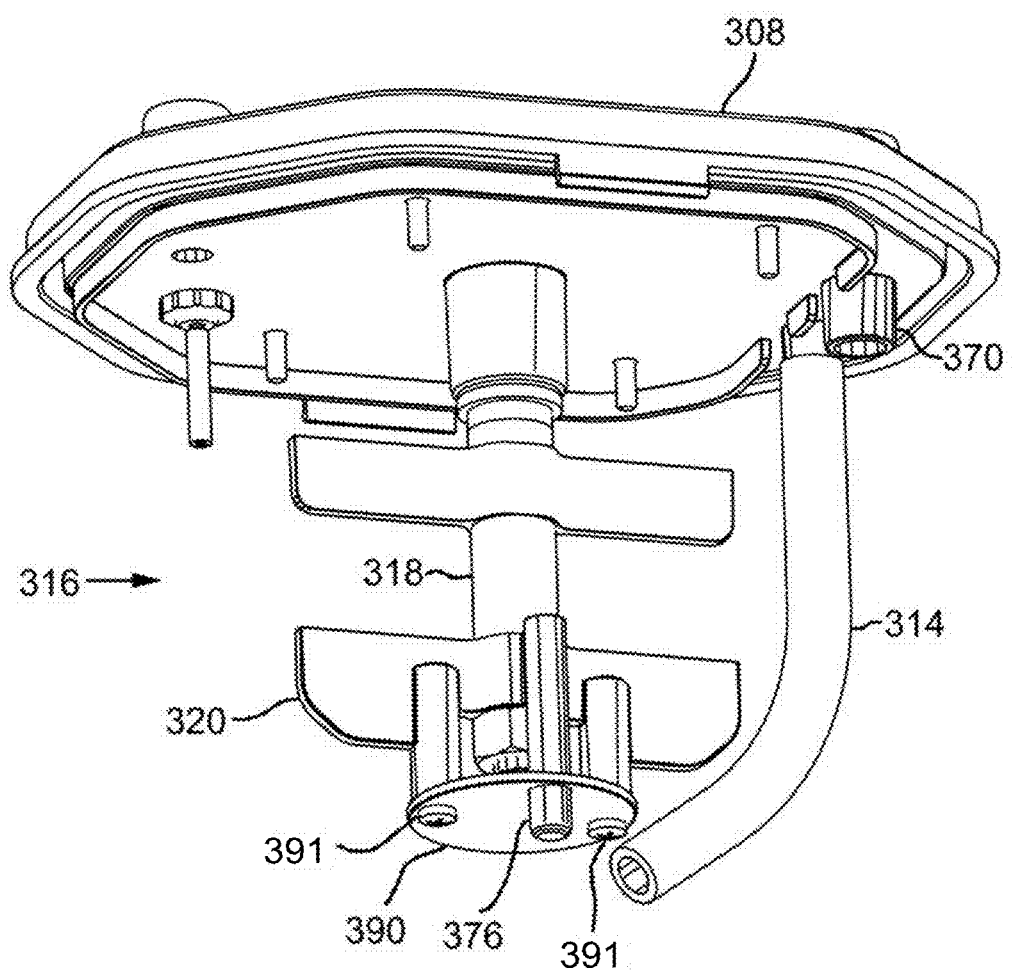
FIG. 28 shows a configuration of the tissue collection and processing apparatus of FIG. 12.
Figure 29:
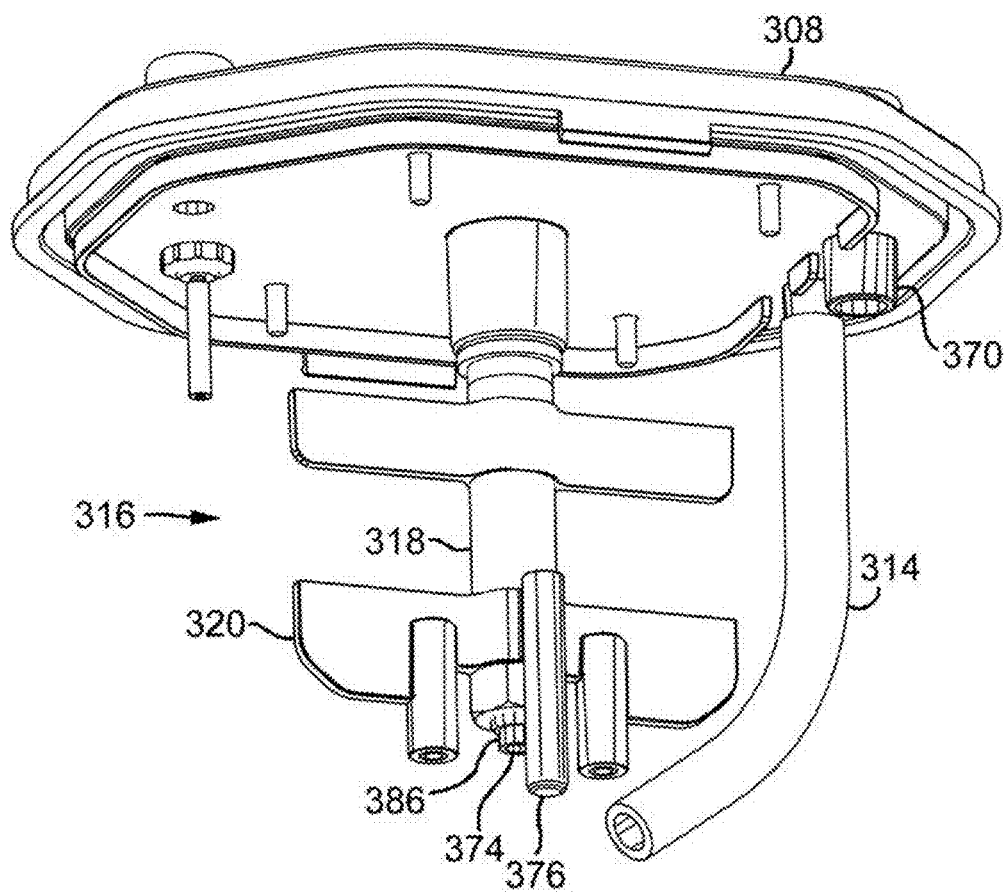
FIG. 29 shows another configuration of the tissue collection and processing apparatus of FIG. 12.

Referring now to FIGS. 15, 28 and 29, the rotatable shaft 318 may include a filter contact member 376 that is offset from an axis of rotation of the rotatable shaft 318. A lower end of the filter contact member 376 may contact a portion of the filter 312 as illustrated in FIG. 15. As the rotatable shaft 318 is rotated, the filter contact member 376 may rotate in a circular path about the axis of rotation of the rotatable shaft 318 remaining in contact with and moving along a portion of the filter 312. This contact may cause the filter 312 to deform and such deformation and/or the contact between the filter contact member 376 and filter 312 may cause materials that may have adhered to the filter 312 in this region to become dislodged from the filter 312. Thus, the filter contact member 376 may assist in keeping the filter from clogging and increasing the effectiveness of the filter 312.

The rotatable shaft 318 may include a lumen 374 therethrough. The top of the lumen 374 is visible in FIG. 13 and the bottom of the lumen 374 is at the opposite end of the rotatable shaft (FIG. 14). The bottom of the lumen 374 is visible in FIG. 29. The lumen 374 may have a distal end 386 (FIG. 14, FIG. 29) within the tissue retention volume 332 and a proximal end 388 (FIGS. 13 and 14) outside of the internal containment volume 330 and thus may allow access to the tissue retention volume 332 therethrough. The lumen 374 may be disposed along the central axis of the rotatable shaft 318. The lumen 374 thus provides a conduit for accessing the internal containment volume 330. As further described below, the lumen 374 may provide access for removing processed material from the internal containment volume 330. In that respect, the opening through the lid 308 through which the rotatable shaft 308 extends acts as an extraction port through which access is provided via the lumen 374 that passes through such opening. The apparatus 300 may include a plug 378, shown in FIG. 14 and not shown in FIG. 13, that may be placed in the proximal end 388 of lumen 374 to seal the lumen 374.

Figure 27:
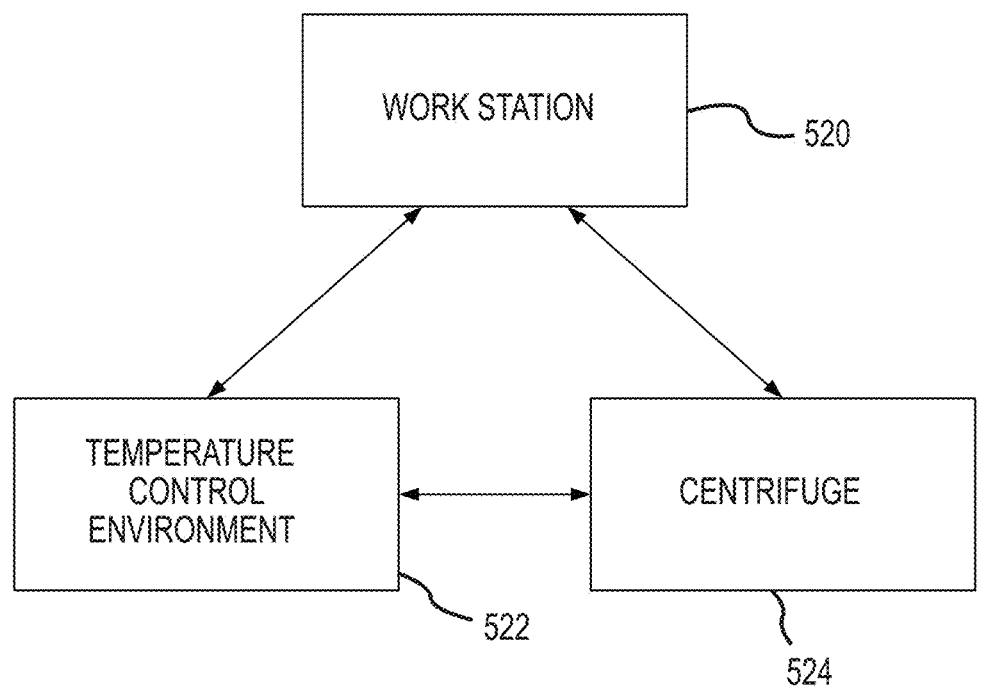
FIG. 27 illustrates transportability of a container to accommodate performing different processing operations at different locations.

As illustrated in FIGS. 28 and 29, the apparatus 300 may include an optional barrier member 390 (shown in FIG. 27, absent from FIG. 28). The barrier member 390 may be secured to the mixing device 316 via two screws 391 or by any other appropriate means such as snaps or by being molded integrally with the mixing members 320.

Figure 16:
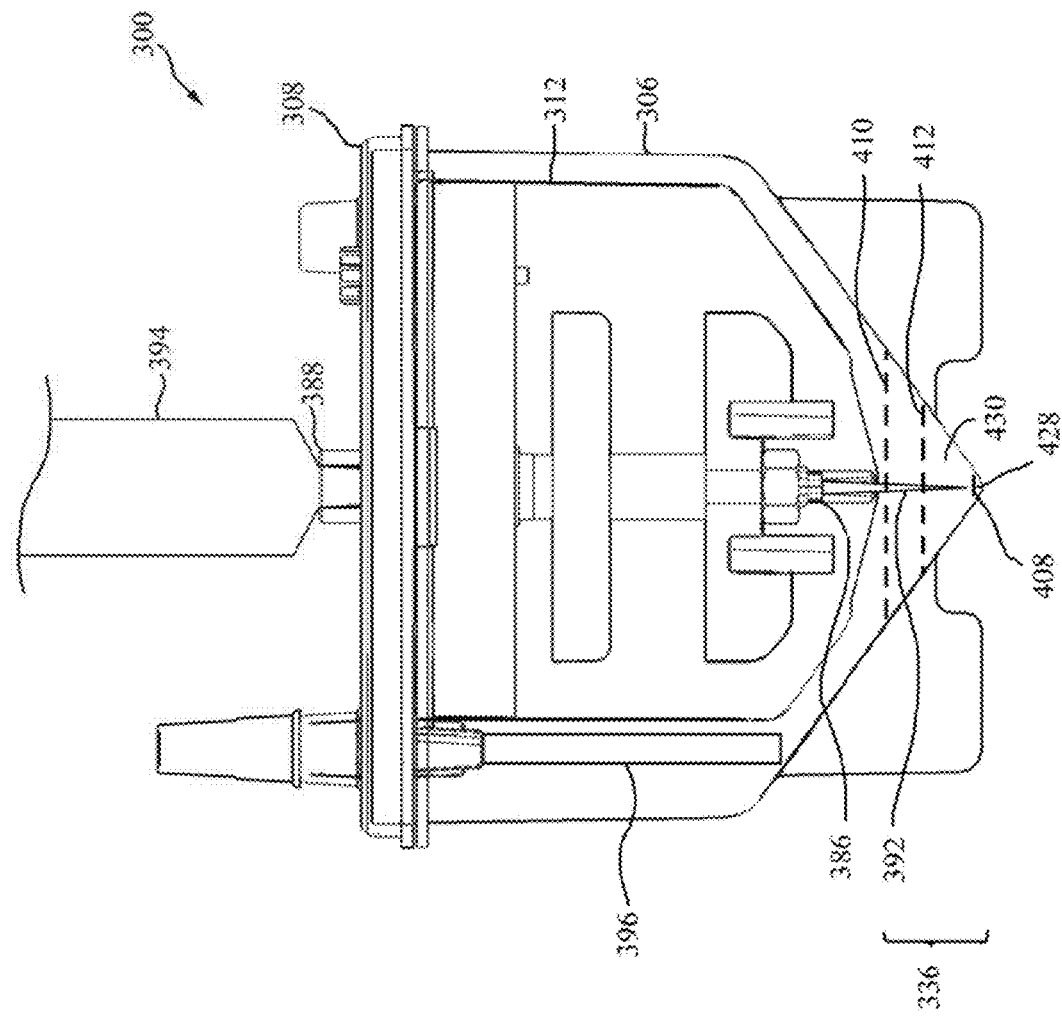
FIG. 16 illustrates a needle inserted into a tissue collection and processing apparatus.

As shown in FIG. 16, in configurations where the barrier member 390 is not present, a hypodermic needle 392 may be inserted through the lumen 374 and may be advanced out of the distal end 386 of the lumen 374 and to pierce through the filter 312 to directly access the collection volume 336 (the volume under the line 410 in FIG. 16). Thus, without the barrier member 390 present, the hypodermic needle 392 may be used to inject material into, or remove material from the collection volume 336. Additionally, as the axis of the lumen 374 is vertically oriented, access to the collection volume 336 using the hypodermic needle 392 is by downward vertical insertion into the lumen 374 from above the container. Such vertical insertion coupled with the ability of the apparatus 300 to be placed on a flat surface in the collection orientation, allows for user-friendly access to the collection volume 336, and helps avoid complications that could compromise operations to collect valuable processed material from the collection volume 336.

The hypodermic needle 392 may be interconnected to a syringe 394. The proximal end 388 of the lumen 374 may include a tapered receptacle adapted to mate with a tapered tip of the syringe 394. In this regard, as shown in FIG. 16, the depth of penetration by the hypodermic needle 392 into the collection volume 336 when the tapered tip of the syringe 394 is in contact with the tapered receptacle of the lumen 374 may be controlled by controlling the length of the hypodermic needle 392 extending from the syringe 394. Additionally, the proximal end 388 of the lumen 374 may include a feature, such as a notch, to retain an o-ring (not shown) such that when the syringe 394 is positioned against the proximal end 388 of the lumen 374, the o-ring forms a seal between the proximal end 388 of the lumen 374 and the syringe 394 (i.e., a seal through the o-ring between a wall surface in the tapered receptacle and an exterior wall surface of the tip of the syringe inserted into the tapered receptacle).

In configurations where the barrier member 390 is present, as shown in FIG. 28, direct access from the lumen 374 to the collection volume 336 is prevented. Furthermore, the distance between the barrier member 390 and the distal end 386 of the lumen 374 may be selected to achieve a desired flow restriction through a gap between the distal end 386 of the lumen 374 and the barrier member 390. For example, the distance between the barrier member 390 and the distal end 386 of the lumen 374 may be between one and five millimeters. Such a distance may be beneficial when the apparatus 300 is employed to perform a fat graft and the lumen 374 is used to remove tissue from the tissue retention volume 332. By maintaining an appropriate standoff between the barrier member 390 and the distal end 386 of the lumen 374, and by configuring the barrier member with an appropriate areal extension beyond the perimeter of the opening of the distal end 386 of the lumen 374 (e.g., the barrier member 390 is a large enough plate), potential for flow short-circuiting to draw in air or other fluid through the filter 312 from the filtrate volume 334 may be significantly reduced or avoided when processed material (e.g., for a fat graft) is extracted by suction through the lumen 374.

Referring to FIGS. 17A and 17B, the second suction port 370 includes a translatable member 396 that may be translated up and down relative to the lid 308 to vary the depth (elevation within the filtrate volume 334) at which material from the filtrate volume 334 is drawn through the second suction port 370. Examples of the various depths (elevations) at which the translatable member 396 may be positioned are illustrated in FIGS. 17A, 19, 20 and 22 and are discussed below in relation to methods of using the apparatus 300. The fit between the translatable member 396 and the opening through the lid 308 of the second suction port 370 is such that the translatable member 396 may be readily translated up and down to a desired level, while maintaining a tight enough fit to allow a vacuum applied to the translatable member 396 to adequately draw material out of the filtrate volume 334.

Figure 18:
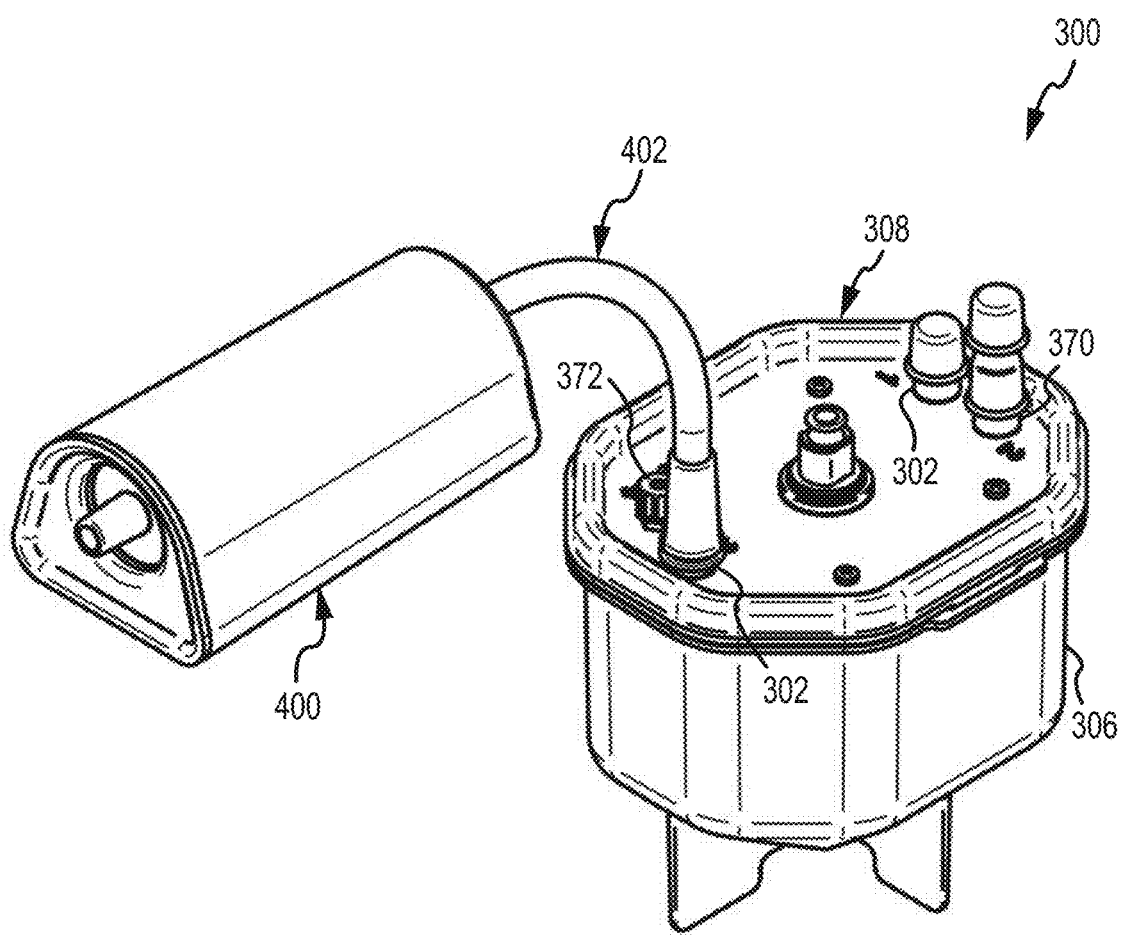
FIG. 18 illustrates a pre-filter and a tissue collection and processing apparatus.

As illustrated in FIG. 18, the apparatus 300 may include a pre-filter unit 400 fluidly connected to the inlet port 304 via a length of tubing 402. The pre-filter unit 400 may comprise within a housing a pre-filter, which may be in the form of a mesh screen with openings, for example, preferably in a range of from 0.5 millimeter to 2 millimeters. The pre-filter unit 400 may be used to pre-filter tissue prior to introduction into the tissue retention volume 332 of the apparatus 300. The tissue being pre-filtered may be supplied from a lipoplasty cannula used during a lipoplasty procedure. Moreover, the suction port 302 of the apparatus 300 may be fluidly connected with a canister 206 via a suction conduit 208 similar to as illustrated in FIG. 3.

In general, the parts discussed with reference to the apparatus 300 may be made from any appropriate biocompatible material. In particular, the shell 306 may be made from a biocompatible transparent polymer material to allow inspection of the contents therein. Screws 326, 391 and the rotatable shaft 318 may be made from metal, such as stainless steel. Other parts of the assembly 300 pictured in FIG. 11 may be made from appropriate biocompatible polymers.

Various exemplary dimensions of one specific nonlimiting example of an apparatus 300 will now be described with reference to FIGS. 11 and 15. In this example, the apparatus 300 has apparatus height $H_A$ of about 157 mm, an apparatus length L of about 145 millimeters, and an apparatus depth D of about 126 millimeters. The containment volume height Hc is about 124 millimeters. The example has an available processing volume 366 of about 760 milliliters and a collection volume 336 of about 23 milliliters. The portion of the tissue retention volume 332 that coincides with the available processing volume 366 is about 580 milliliters. As will be appreciated, a milliliter is equal in volume to a cubic centimeter, and the volumes listed here in milliliters may be equivalently stated as cubic centimeters.

In a method for processing tissue from a lipoplasty procedure using the apparatus 300, the tissue is processed within the internal containment volume 330 to prepare within the apparatus 300 a concentrated product comprising at least one target component, or at least one target material, from the tissue. Many features of the previously discussed methods may also be employed in the current method where appropriate. Such features include, inter alia, multiple washings, shaking, heating, and centrifuging as previously described. Returning to the present method, the tissue is introduced into the tissue retention volume 332 through the inlet port 304. The tissue may be pre-filtered using pre-filter unit 400 prior to being introduced into the tissue retention volume 332. The method may comprise washing tissue in the internal containment volume 330 with a wash liquid. Optionally, the washing may include centrifuging the apparatus 300. After washing, the method may comprise digesting tissue within the internal containment volume 330. After the digestion, the method may include centrifuging the apparatus 300 to prepare in the collection volume 336 a concentrate product comprising at least one target component. For example the concentrate product may comprise, or may consist essentially of, stromal vascular fraction from adipose tissue, and a target component may be stem cells from adipose tissue.

During the washing, the wash liquid may be added to the internal containment volume 330 to contact tissue within the tissue retention volume 332 and with at least a portion, preferably a majority, and more preferably most, of the wash liquid passing through the filter 312 into the filtrate volume 334. The addition of the tissue to the internal containment volume 330 may occur simultaneously with the wash liquid being removed from the filtrate volume 334 via vacuum applied to the suction port 302. In this regard, a volume of tissue larger than the internal containment volume 330 may be introduced into the internal containment volume 330 during the performance of the method. Moreover, the removal of wash liquid may continue after the introduction of tissue into the internal containment volume 330 has stopped.

The wash liquid may wash one or more components from the tissue while retaining washed tissue in the tissue retention volume 332. The washed tissue may be retained in the tissue retention volume 332 by the filter 312. Wash liquid passing into the filtrate volume 334 may be removed from the filtrate volume 334, along with any component or components washed from the tissue. Optionally, after adding the wash liquid, the apparatus 300 may be centrifuged to facilitate a high degree of separation of the wash liquid from the tissue retained in the tissue retention volume 332. Next, the wash liquid may be removed from the filtrate volume 334 by suctioning through the suction port 302 of the apparatus 300. The washing may include multiple wash stages. During the washing, the mixing device 316 may be rotated by rotating the handle 382 to mix contents of the internal containment volume and assist the washing process.

During the digestion, an enzyme, such as for example collagenase, may be added to the internal containment volume 330 through the additional access port 372 or through the inlet port 304. During the digesting, the mixing device 316 may be rotated to assist in the digesting process.

After adding the enzyme, the digesting may comprise agitating contents of the containment volume of the apparatus 300 for a time and at a temperature sufficient for the digestion to proceed to an extent to significantly release the target component, or material, in the desired form capable of passing through the filter 312. The agitating may involve any method to agitate contents of the internal containment volume 330, including for example one or both of: (a) shaking the apparatus 300 to agitate the contents within the apparatus 300 and (b) mixing the contents within the apparatus 300 by rotating the mixing device 316 using the handle 382.

Figure 19:
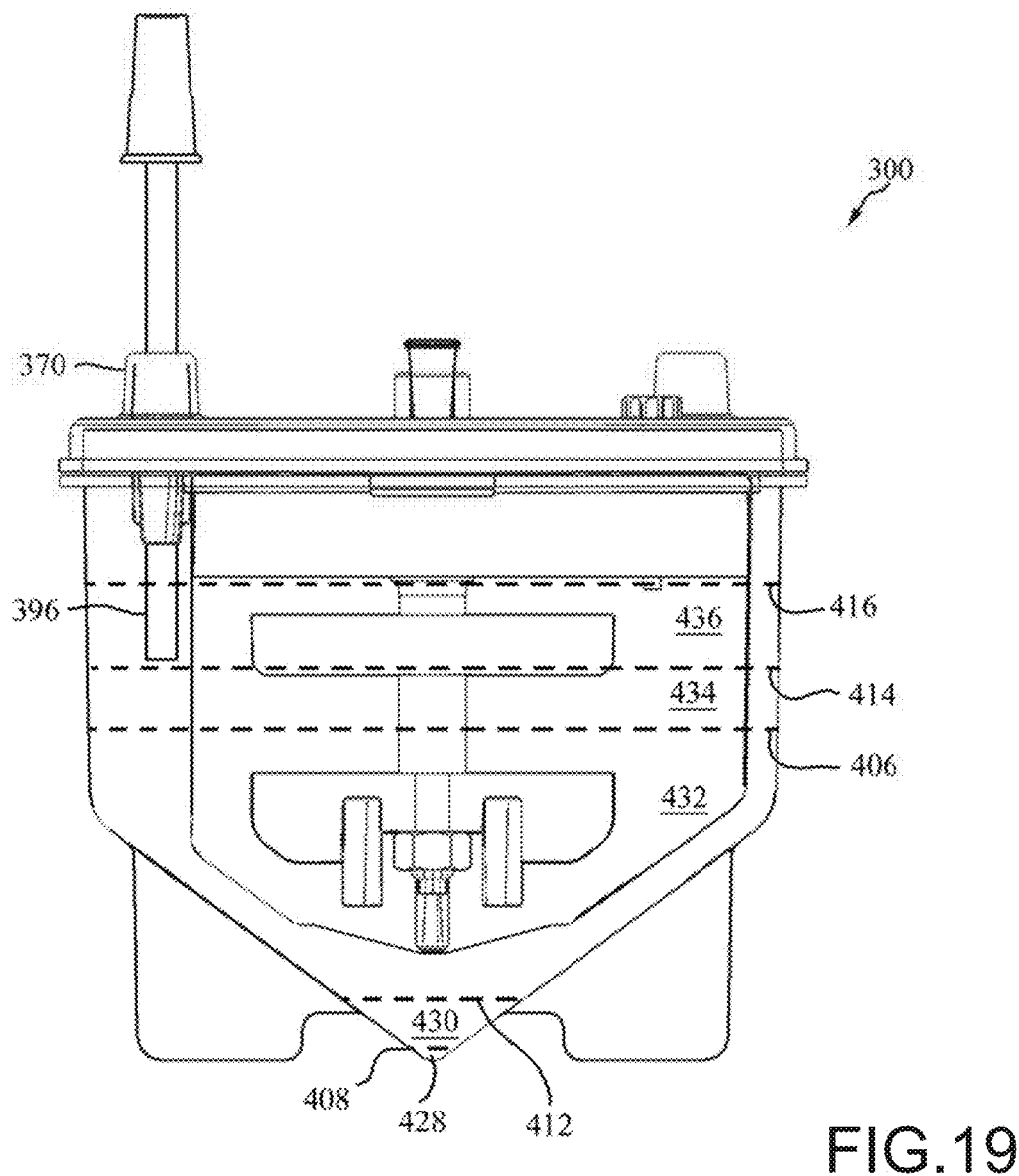
FIGS. 19-22 illustrate various operations in a method of processing tissue within a tissue collection and processing apparatus.

Post-digestion centrifuging promotes separation of the target component from the digested tissue and passage of the target component through the filter 312 for collection in the collection volume 336. The target component may include leuko stromal vascular cells (e.g., stem cells) from adipose tissue. As illustrated in FIG. 19, multiple material phases may collect within the filtrate volume 334 as a result of the centrifuging. The first (bottom) material phase may be a small layer of red blood cells 428 located in the region of the filtrate volume 334 below the line 408. This volume below the line 408 occupies a bottom portion of the collection volume 336, and in many situations may even not be present or may be so small as to be indistinguishable. The second material phase may be a stromal vascular fraction layer 430 from adipose tissue and may be located in the region of the filtrate volume 334 below the line 412 and above the line 408. As will be appreciated, the red blood cell layer 428 and the stromal vascular fraction layer 430 may not be divided by a sharp line, and the blood cell layer 428 may grade into the lower portion of the stromal vascular fraction layer 430. This volume below the line 412 and above the line 408 also occupies a portion of the collection volume 336. The stromal vascular fraction layer 430, or the stromal vascular fraction layer 430 together with the red blood cell layer 428, may be in the form of a pellet. A third material phase may be an aqueous layer 432 that occupies the region of the filtrate volume 334 below the line 406 and above the line 412. A fourth material phase may be a disaggregated adipose layer 434 that occupies the region of the filtrate volume 334 below the line 414 and above the line 406. A fifth material phase may be an oil layer 436 that occupies the region of the filtrate volume 334 below the line 416 and above the line 414. The separated phase layers as shown are provided to illustrate relative positioning and are not intended to represent an actual scale of the relative sizes of the phases, except that the red blood cell layer 428 and stromal vascular fraction layer 430 are contained within the collection volume 336 and the other layers extend above the collection volume. As will be appreciated, the material phases 428, 430, 432, 434 and 436 are in order of decreasing density, with red blood cell layer 428 being the most dense phase and with the aqueous layer 432, the disaggregated a dispose layer 434 and the oil layer 436 all being less dense than the stromal vascular fraction layer 430.

Figure 20:
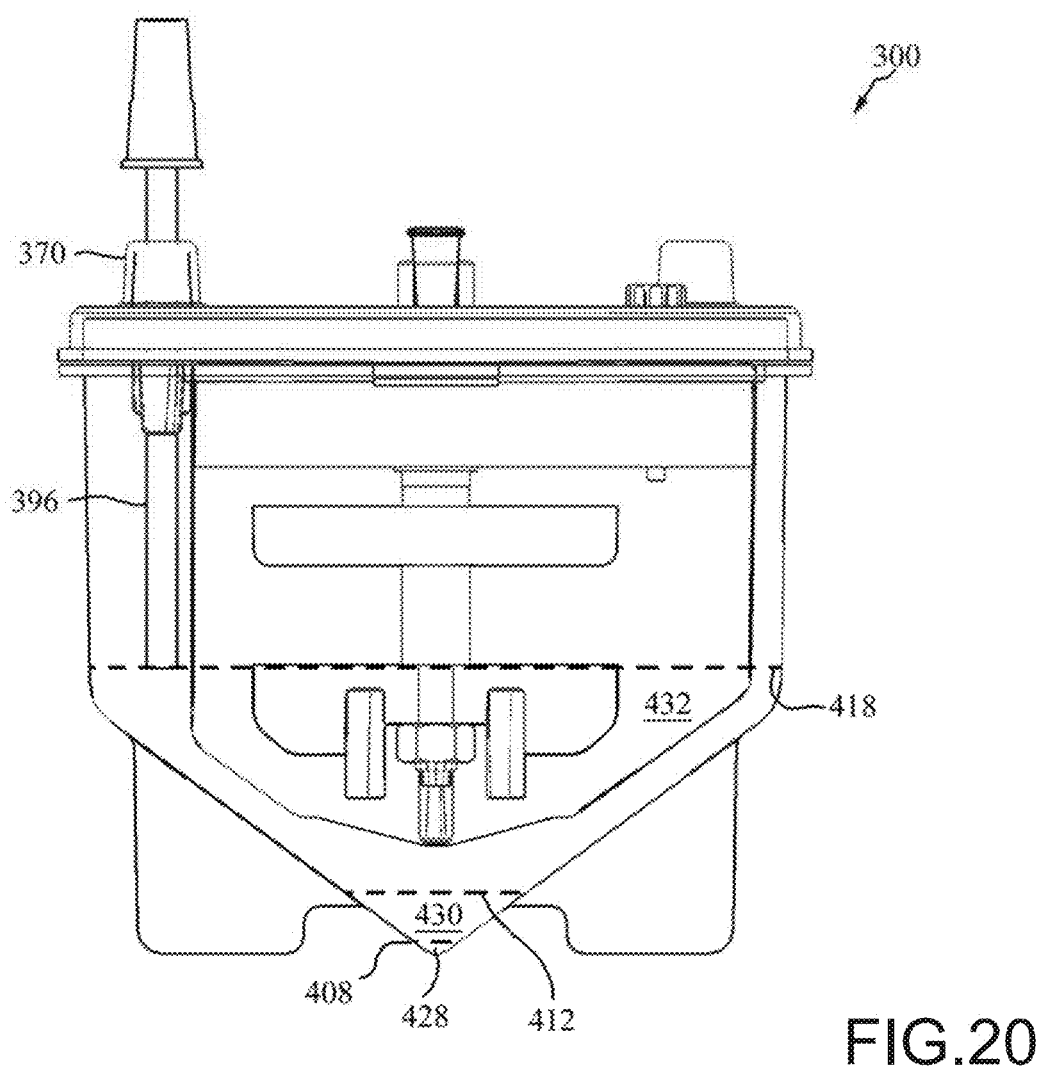

The translatable member 396 of the second suction port 370 may be employed to first remove the oil layer 436, then to remove the disaggregated adipose layer 434, and then to remove the aqueous layer 432. As illustrated in FIG. 19, the translatable member 396 may be positioned such that the end of the translatable member 396 is disposed within the oil layer 436. Suction applied to the translatable member 396 will remove the As fluid is removed, the translatable member may be lowered to remove additional fluid down to a desired level, which may be removal of all or most of layers 436,434 and 432. For example, once the oil layer 436 has been removed, the translatable member 396 may be lowered into the disaggregated adipose layer 434 and then the aqueous layer 432 for sequential removal of these layers. FIG. 20 illustrates the aqueous layer 432 partially removed (after already removing the top layers 436 and 434 such that the top of the aqueous layer 432 is at line 418). As another example, the translatable member 396 may be initially inserted to the position shown in FIG. 20 and suction applied until a portion of the aqueous layer 432 is removed and also the disaggregated adipose layer 434 and oil layer 436 are removed above line 418, resulting in the arrangement of FIG. 20.

Figure 21:
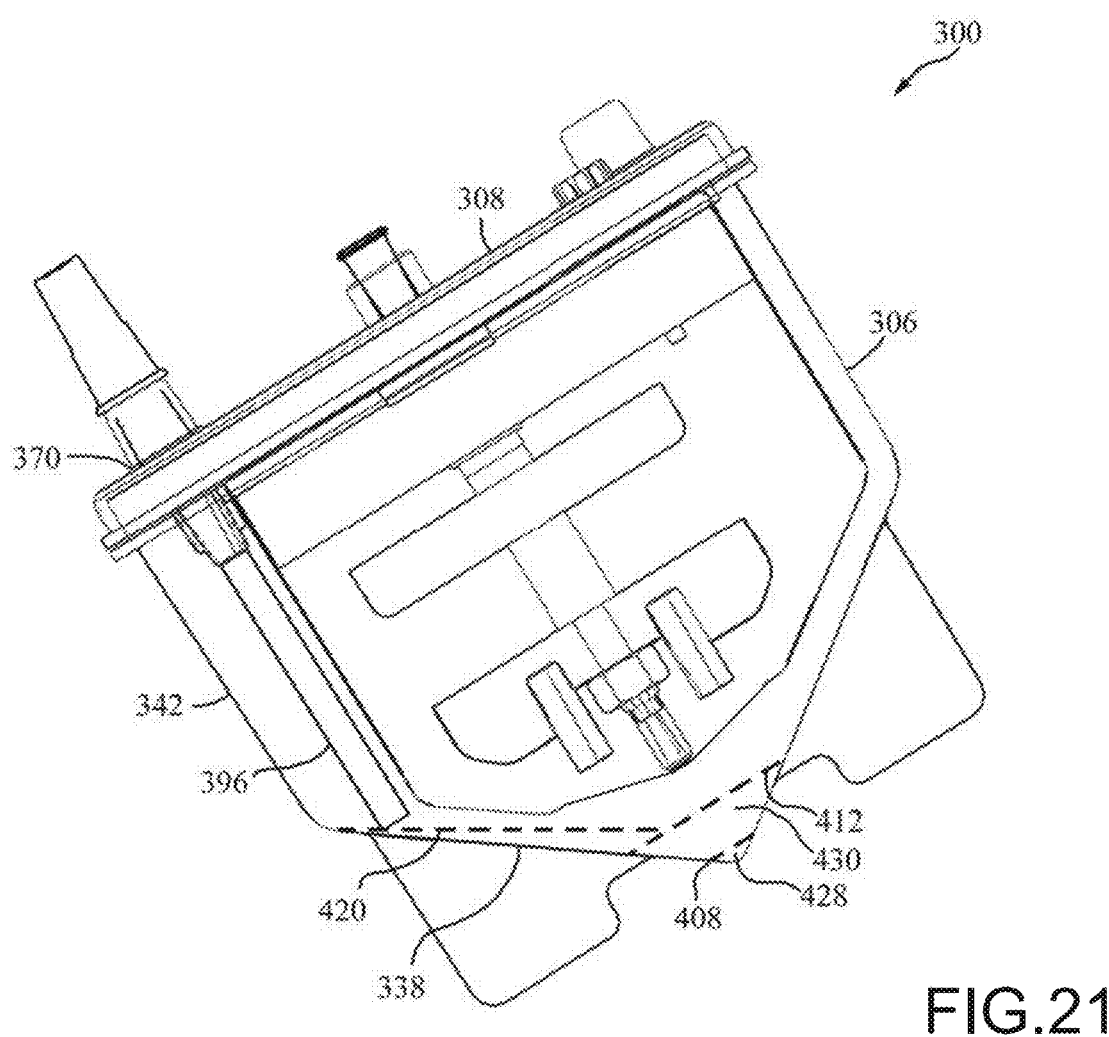
Figure 22:
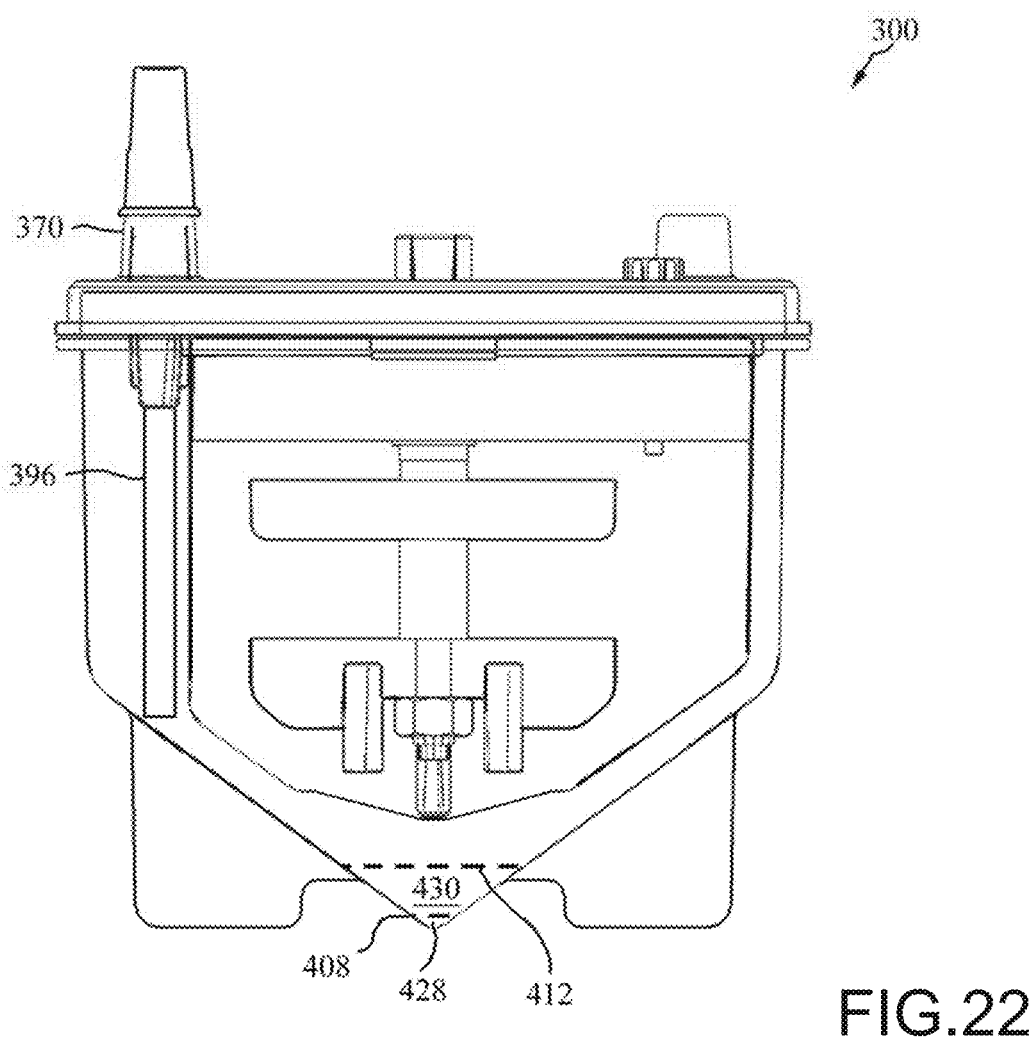

Once fully inserted into the filtrate volume 334, the translatable member 396 may not be operable to remove a portion of the aqueous layer 432 while the apparatus 300 is in the collection orientation. Accordingly, a user may gently tilt the apparatus 300 as illustrated in FIG. 21 to further remove the aqueous layer 432. As illustrated, the stromal vascular fraction layer 430 below the line 412 may form a pellet which may retain its position as the apparatus 300 is tilted. This attribute of the pellet allows the apparatus 300 to be tilted such that the aqueous layer 432 flows laterally toward the translatable member 396 disposed proximate to the interface between the tapered wall portion 338 of the shell 306 and the straight wall portion 342 of the shell 306 as illustrated by line 420 in FIG. 21. Such tilting can allow suction to be applied to the aqueous layer 432 without the suction substantially affecting the stromal vascular fraction layer 430, which remains in place and stationary relation to the container. Once the aqueous layer 432 has been satisfactorily removed, the apparatus 300 may be returned to its collection orientation, as shown in FIG. 22, for removal of the stromal vascular fraction layer 430 from the collection volume 336.

Next, the hypodermic needle 392 may be inserted into the collection volume 336 as illustrated in FIG. 16 and a diluent fluid (e.g., suspension liquid) may be injected into the collection volume 336 such that the diluent fluid, stromal vascular fraction layer 430 and the layer of red blood cells 428 together occupy at least a portion of the collection volume 336 under line 410, and are preferably limited to being present only in the collection volume 336 and do not occupy space above line 410. After injection of the diluent fluid, a user may gently tap the apparatus 300 against a hard surface to cause the diluent fluid to mix with the stromal vascular fraction and the layer of red blood cells. A second hypodermic needle may then be inserted through the lumen 374 and the diluent/stromal vascular fraction/red blood cell mixture may be removed from the apparatus 300, for example by drawing the mixture through the hypodermic needle and into a syringe.

Figure 23:
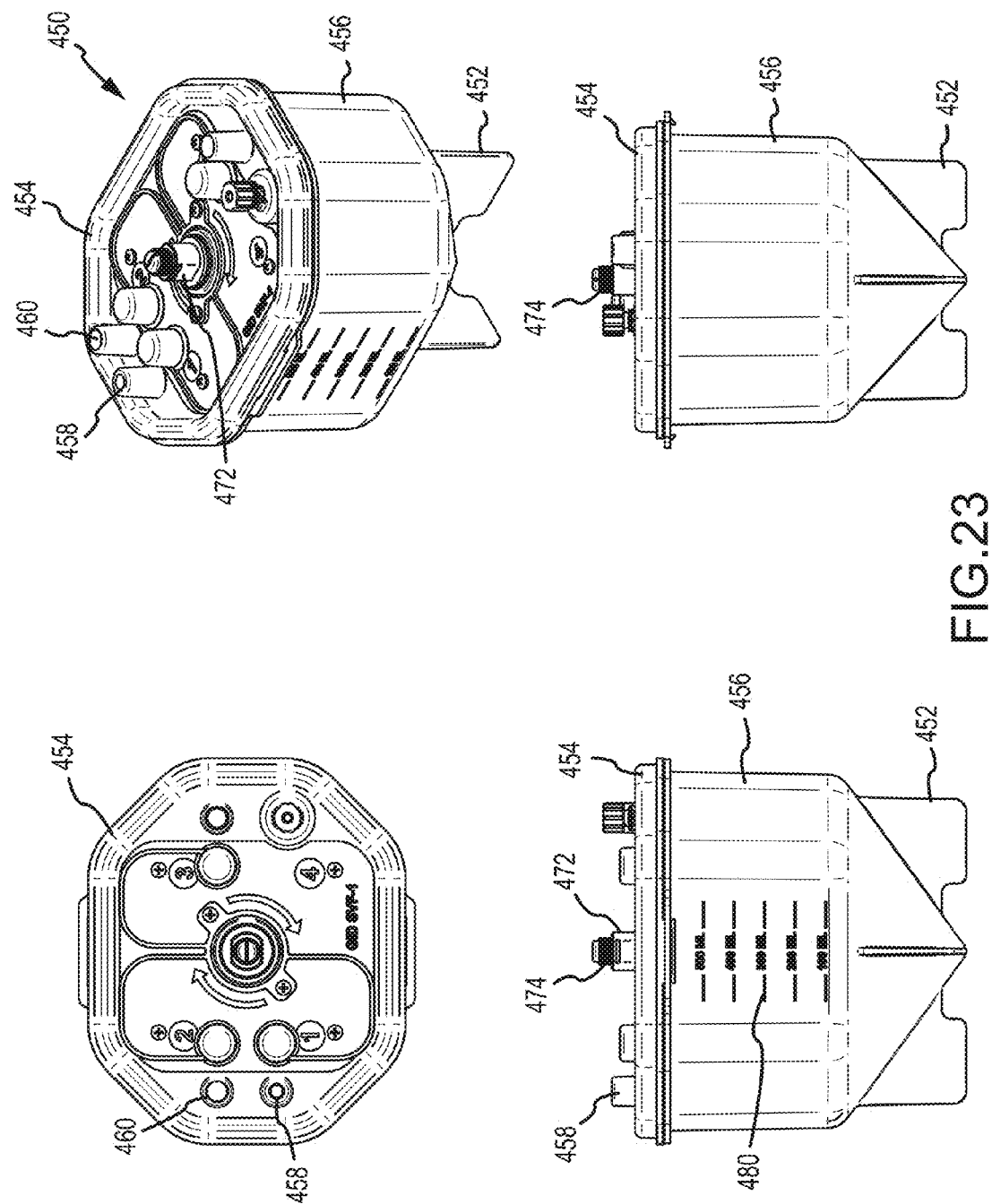
FIG. 23 shows top, perspective, side and end views of another embodiment of a tissue collection and processing apparatus.
Figure 24:
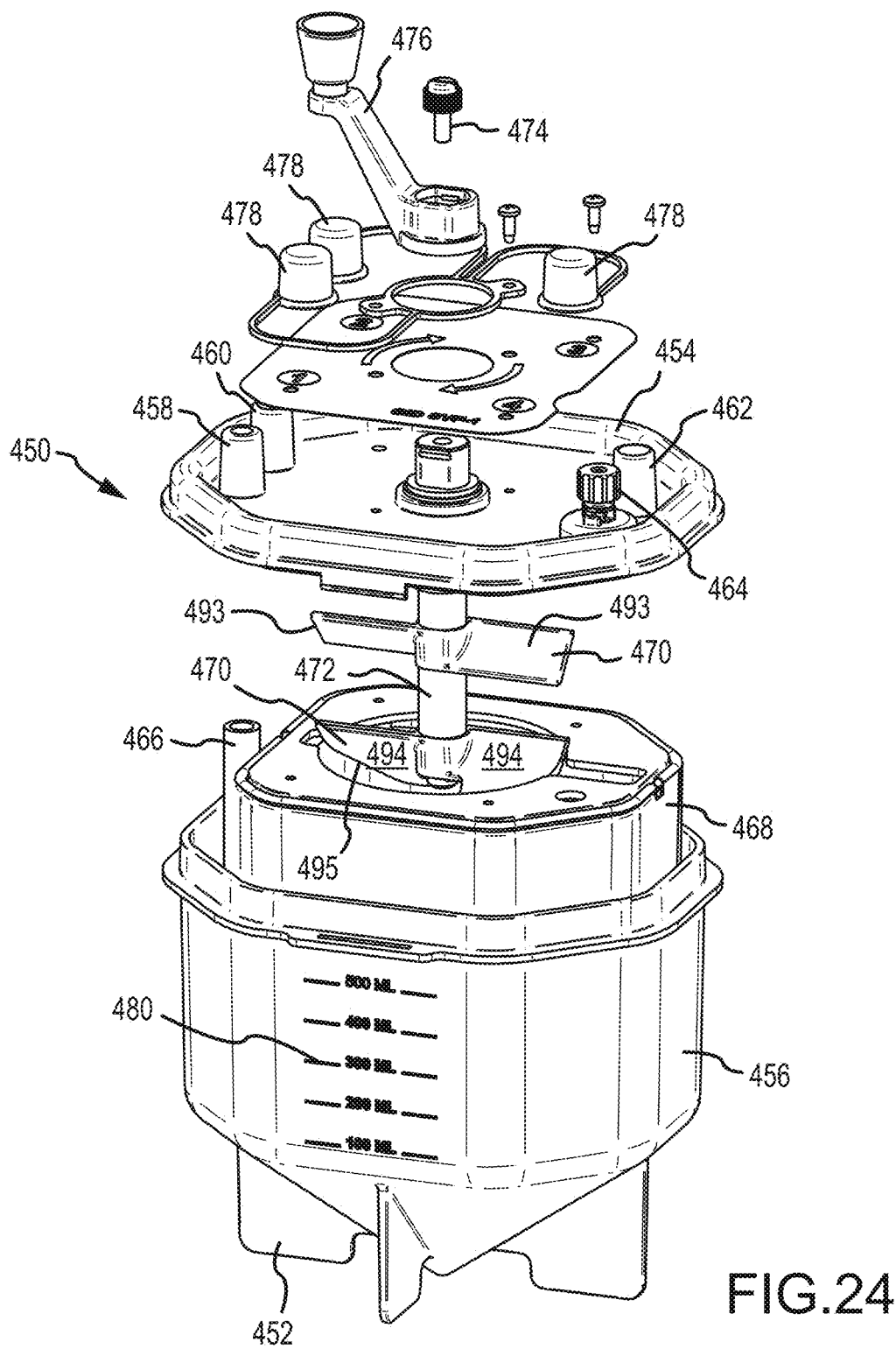
FIG. 24 shows an exploded view of the same tissue collection and processing apparatus as FIG. 23.

Referring now to FIGS. 23 and 24, a further embodiment is shown for a tissue collection and processing apparatus. As shown in FIGS. 23 and 24, a tissue collection and processing apparatus 450 has a collection orientation in a freestanding, upright position as supported by base supports 452. The apparatus 450 includes a lid 454 covering a bowl-like shell 456, which make up a container having an internal containment volume under the lid 454 within the shell 456. The apparatus 450 includes a first suction port 458, a second suction port 460, an inlet port 462 and an auxiliary access port 464, which may be generally as describes for similar features of the apparatus 300 described with respect to FIGS. 11-17.

The first suction port 458 is connected with a suction conduit 466 extending from the first suction port 458 to within a tapered portion of an internal containment volume of the apparatus 450. The second suction port 460 is adapted to receive a translatable suction conduit, similar to the translatable member 396 described with respect to FIG. 17. The apparatus 450 includes a filter 468 suspended from the lid 454 and which divides the internal containment volume in the apparatus between a tissue retention volume disposed inside the filter 468 and a filtrate volume disposed on the other side of the filter 468. The apparatus 450 includes a rotatable mixer disposed within the filtrate volume that includes propellers 470 connected to a rotatable shaft 472, which may be rotated to operate the rotatable mixer and cause the impellers 470 to mix and circulate fluid within the internal containment volume of the apparatus 450. The propellers 470 may alternatively be referred to as impellers or mixing impellers. The rotatable shaft 472 includes an internal lumen that extends from a proximal end outside of the container of the apparatus to a distal end in the tissue retention volume, to permit access into the internal containment volume in a manner similar to that discussed previously for the apparatus 300 shown in FIGS. 11-17. A removable plug 474 may be disposed in a proximal end of the lumen for sealing the lumen when the lumen is not in use. The rotatable shaft includes a handle interface which may be interfaced with a hand-manipulable handle 476 (FIG. 24) to operate the rotatable mixer. The rotatable mixer is designed for primary operation by rotating the handle in a clockwise direction, as indicated by the directional arrows on a plate as shown in FIG. 14. The apparatus 450 includes attached caps 478 which may be used to cap the first suction portion 458, second suction port 460 and inlet port 462 as needed, such as to seal the container for transportation between processing locations or during agitation on a warmer-shaker during digestion operations. The apparatus 450 is operable substantially in the same way as described previously for the apparatus 300 shown in FIGS. 11-17. The apparatus 450 includes volume gradation markings 480 that indicate the volume contained within the tissue retention volume (within the filter 468) up to different elevations of the container 450 when in the access orientation.

With continued reference to FIGS. 23 and 24 features of one or both of the propellers 470 may be configured to assist mixing of contents within the portable container apparatus and to reduce potential for plugging of the filter 468. One or both of the propellers 470 may have pitched blades that direct flow of fluid from the respective propeller 470 in an axial direction relative to the axis of rotation of the rotatable shaft 472. As shown in FIG. 24, the configuration of the bottom propeller 470 may include impeller blades 494 that are pitched at an angle that will propel fluid flow in an upper axial direction along the rotatable shaft 472 when the rotatable shaft 472 is rotated in the clockwise rotational direction. This type of upward pumping action by the bottom propeller 470 may assist in moving material from the filter 468 to help keep the filter 468 from plugging. In similar manner, the top propeller 470 may have pitched blades 493 that propel fluid flow in an axial direction upward toward the underside of the lid 454 and away from the tissue collector 482 when the rotatable shaft 472 is rotated in the clockwise rotational direction. This upward pumping action by the top propeller 470 may assist in further pulling material up and away from the filter 468 to help prevent plugging of the filter 468.

In one enhancement, one or more of the blades 494 may be configured to scrape at least a portion of the filter 468 when the rotatable shaft 472, and thus also the bottom propeller 470, is rotated in the clockwise rotational direction. Such scraping of the filter 468 may be accomplished by configuring an edge portion 495 of a blade 494 to contact and scrape surfaces of the filter 468. In that regard, a blade may be configured with a slanted lower edge shaped to correspond with and contact a corresponding tapered portion of the filter 468. A leading edge of the blade 494 may have a tapering width to assist in scraping tissue or other material away from the surface of the filter 468. For example, the configuration of the blade 494 may include a beveled surface toward a leading edge of a slanted edge portion that contacts the filter 468 and that may help to lift tissue or other material away from the filter 468 when the lower propeller 470 is rotated in the clockwise rotational direction.

Figure 25:
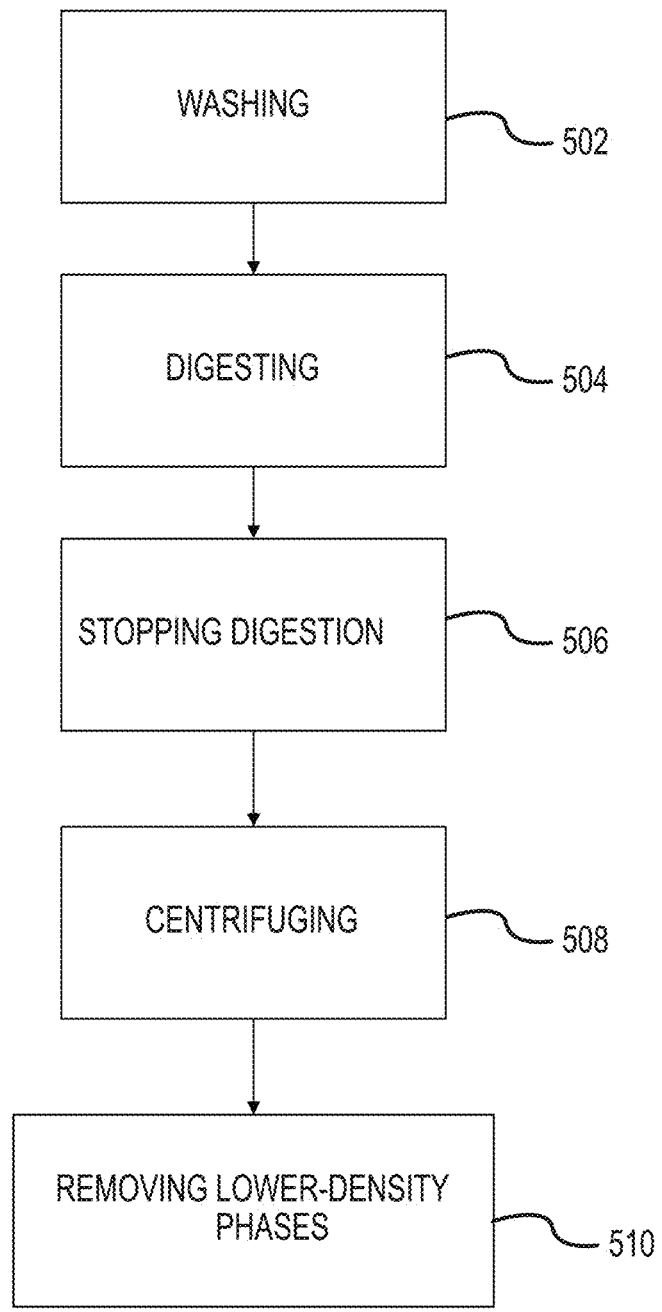
FIG. 25 is a generalized process block diagram of an embodiment of a method of processing adipose tissue.

FIG. 25 as a generalized process block diagram illustrating one embodiment of a method of the invention. As shown in FIG. 25, the method includes a washing step 502, during which adipose tissue disposed within a portable container is washed to remove contaminants from the adipose tissue. Contaminants that may be associated with the adipose tissue include for example blood, free lipids, small particles and debris and other materials that may have been collected with the adipose tissue or result from degradation during a tissue collection operations.

The washing 502 may include one or, preferably, multiple wash cycles during which adipose tissue is washed with wash liquid within the container. The wash liquid, for example, may be a buffer solution, such as Lactated Ringer's solution or Hank's Balanced Solution, and may have additional additives, such as one or more of an anti-clotting agent, an antibiotic and an antifungal. An anti-clotting agent may beneficially prevent coagulation of blood that may be present, and may assist effective washing of blood from the adipose tissue. Antibiotics and antifungals may help protect against problems associated with inadvertent outside contamination of the adipose tissue within the container. Such a wash liquid may also include one or more additional buffering agents, such as glycine. One preferred material for use as an anti-clotting agent is heparin.

During a wash cycle, the wash liquid is mixed with the adipose tissue in the container and then preferably substantially all of the wash liquid with washed contaminants from the adipose tissue is removed from the container from a first side (filtrate volume side) of a filter within the container while retaining the washed adipose tissue in the container on a second side (tissue retention volume side) of the filter.

The washing may include any of the feature refinements and additional features discussed above.

After the washing 502, the washed adipose tissue in the container is subjected to a digesting step 504. Digestion medium comprising a collagenase enzyme solution is added to the container to contact the washed adipose tissue. The digestion medium is added in a volume ratio of from 0.6:1 to 2:1 of digestion medium: adipose tissue. The digestion medium contains collagenase enzyme in an amount to provide from 150 to 300 collagen digestion units (CDU) per milliliter of catalytic volume. Catalytic volume refers to the total volume of the digestion medium and adipose tissue within the container to which the digestion medium is added. After the digestion medium is added to the container, enzymatic digestion within the container is permitted to proceed for a retention time of from 20 minutes to 50 minutes while the container is disposed in a temperature controlled environment maintained within a temperature range of from 32° C. to 38° C., and with at least occasional, and preferably substantially continuous, agitation of contents to the container. The digesting step 504 may include any of the feature refinements and additional features discussed above.

The method as shown in FIG. 25 also includes a stopping digestion step 506 occurring after the digesting step 504. The stopping digestion step should occur no earlier than the end of the retention time for the enzymatic digestion in the temperature controlled environment, but in any event should be performed within 50 minutes following adding the digestion medium to the container during the digesting step 504. The stopping digestion step 506 includes adding a stopping reagent to the container to positively stop enzymatic activity within the container. This is important, because if enzymatic activity is not discontinued, digestion within the container may proceed to an undesirable degree in which the enzyme may destroy the viability of a significant number of the leuko stromal vascular cells.

As shown in FIG. 25, the method includes, after the stopping digestion step 506, a centrifuging step 508. The centrifuging step 508 is performed with the container disposed in a centrifuge and the centrifuge is operated to centrifuge the container to form density-separated phases within the container. These density-separated phases include a higher-density pellet phase rich in leuko stromal vascular cells, which pellet phase may form adjacent a bottom of the container. The density-separated phases also include lower-density material phases. By lower-density, it is meant that the lower-density material phases have a lower-density than the pellet phase. When the container is oriented with the pellet phase adjacent a bottom of the container (e.g., in an access orientation for the container), the lower-density material phases will be disposed in the container above the pellet phase. The lower-density material phases may include, in order of decreasing density, an aqueous layer, a disaggregated adipose layer (containing remnants of disaggregated adipose tissue) and an oil layer. The pellet phase is enriched in, and may be mostly or even substantially entirely comprised of, leuko stromal vascular cells (e.g., stromal vascular fraction). On a side of the pellet phase opposite the lower-density material phases may be disposed a small red blood cell phase. Provided that washing of the adipose tissue is thorough during the washing step 502, this red blood cell phase may be extremely small, and in some case may be difficult to distinguish from a bottom portion of the pellet phase. The centrifuging step 508 may include any of the feature refinements and additional features discussed above.

After the centrifuging step 508 has been completed, the container is removed from the centrifuge and subjected to a step 510 of removing lower-density phases. During the step 510, the lower-density material phases are removed from the container while the pellet phase is retained within the container, preferably while maintaining pellet phase in an undisturbed state, in place at the location of the container where the pellet collected during the centrifuging step 508. The step 510 may include any of the feature refinements and additional features as discussed above.

As shown in FIG. 25, the stopping digestion step 506 is performed after the digesting step 504 and prior to the centrifuging step 508. Such sequencing is preferred, but not required. In one variation, the stopping digestion step 506 may be performed after the centrifuging 508. However, because enzymatic digestion would continue during the centrifuging, such a variation in the sequence is not preferred, to provide better control over the timing and extent of the enzymatic digestion.

The leuko stromal vascular cells, which include stem cells, contained in the pellet phase represent valuable product. For effective use of these valuable leuko stromal vascular cells, it is generally necessary to remove the cells from the container. This has been a significant problem in the context of using multi-step portable containers for processing that is addressable with various implementations of the invention.

Figure 26:
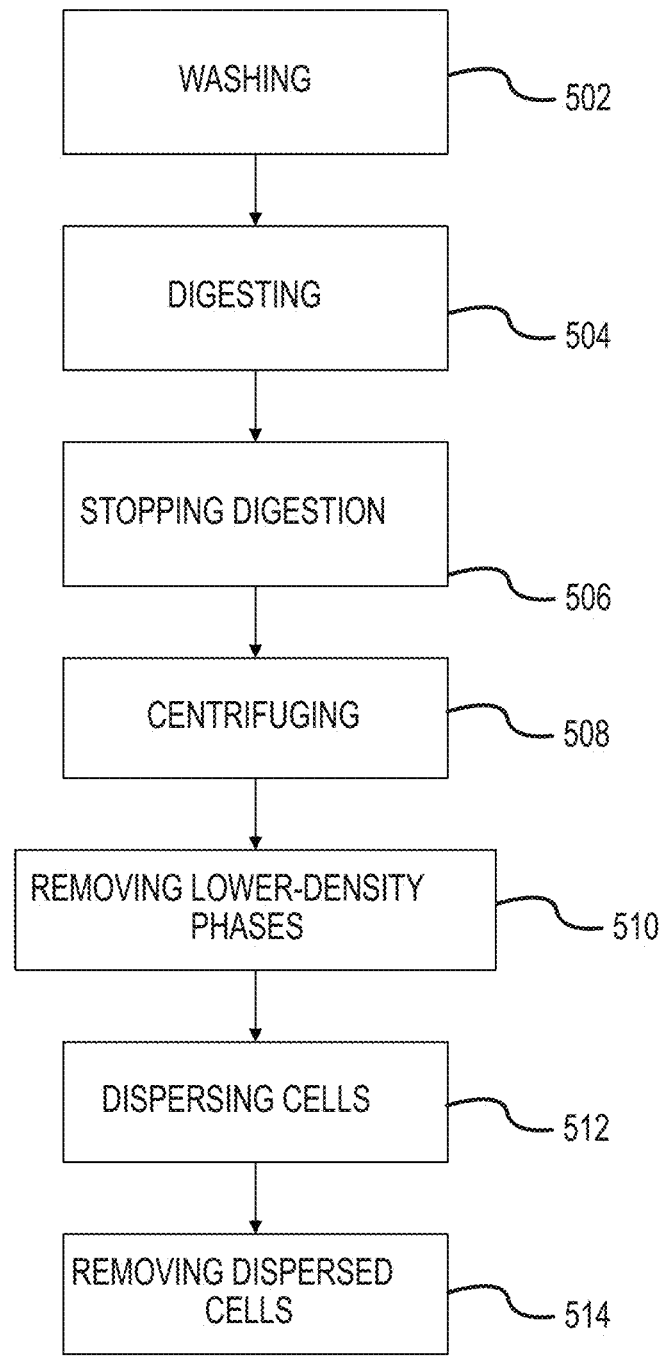
FIG. 26 is a generalized process block diagram of another embodiment of a method of processing adipose tissue.

Referring now to FIG. 26, another embodiment of implementation of a method of the invention is shown. The implementation shown in FIG. 26 includes the washing step 502, the digesting step 504, the stopping digestion step 506, the centrifuging step 508 and the removing of lower-density phases step 510 as discussed with FIG. 25. As shown in FIG.

26, after the removing lower-density phases step 510, the method includes a dispersing cells step 512. During the dispersing cells step 512, aqueous suspension liquid is introduced into the container to mix with the pellet phase and to act as a dispersion medium for dispersing cells of the pellet phase in the suspension liquid. Dispersion of cells from the pellet phase may be aided by tapping the container to dislodge and break up the pellet phase to assist effective dispersion of the leuko stromal vascular cells in the suspension liquid. The dispersing cells step 512 may include any of the feature refinements and additional features as discussed above.

After the dispersing cells step 512, the processing shown in FIG. 26 includes a removing dispersed cells step 514, during which most, and preferably substantially all, of the suspension liquid with the dispersed cells from the pellet phase is removed from the container, thereby recovering the leuko stromal vascular cells from the container. The removing dispersed cells step 514 may include any of the feature refinements and additional features discussed above.

The method of the invention includes multi-step processing in a single portable container, such as for example the container of a tissue collection and processing apparatus as described above. The method is designed to address inherent problems with multi-step processing in a single container. Through careful design of the container (e.g., as described with tissue collection and processing apparatus described above) and combined processing specifics (e.g., washing, digesting, centrifuging, and cell removal specifics), processing in a portable container may be performed efficiently and effectively to process large quantities of collected adipose tissue relative to the total volume of the container and to effectively recover a large number of viable leuko stromal vascular cells released from the processed adipose tissue. This is remarkable given the inherent design deficiencies associated with the use of a single container for performing multiple steps relative to an integrated multi-container processing system with different containers dedicated to different steps of processing.

Reference is now made to FIG. 27, which illustrates portability of the container during implementation of a method of the invention. As shown in FIG. 27, processing may be performed at a facility providing multiple distinct locations where the portable container may be temporarily located to perform different processing operations within the container. FIG. 27 shows three such possible distinct processing locations: a work station, a centrifuge and a temperature controlled environment. As shown by the arrows in FIG. 27, the portable container may be transported between these different locations to perform different process tasks or operations, for example processing tasks and operations associated with the method implementations of FIGS. 25 and 26. The transportation may conveniently be accomplished by a person carrying the portable container between the different locations.

The work station 520 may include a flat work surface, such as a flat surface of a table, bench or counter where the portable container may be stably positioned in an access orientation for convenient access to add material to or remove material from the portable container. In a preferred implementation, when the portable container is in such an access orientation, all access into the container for adding and removing materials is in a downward direction from above the container. Operations that may be performed at such a work station 520 include, for example, one or more of the washing step 502, the stopping digestion step 506, the removing lower-density phases step 510, the dispersing cells step 512, and the removing dispersed cells step 514 shown in FIGS. 25 and 26. Adding digesting medium to the container may also be conveniently performed at such a work station 520. As will be appreciated, an actual facility may include multiple work stations, rather than a single work station as shown in FIG. 27. For example different work stations may be specifically designed and equipped for performing specific processing tasks. Such multiple work stations may be contiguous or at separated locations in a facility.

Enzymatic digestion within the container for a retention time may be performed at the temperature controlled environment 522. The temperature controlled environment may be provided by a warmer-shaker, for example.

Centrifuging (e.g., step 508 of FIGS. 25 and 26) may be performed at the location of the centrifuge 524 shown in FIG. 27.

In a method for processing tissue from a lipoplasty procedure using the apparatus 300, the tissue is collected into and processed within the internal containment volume 330 to prepare within the apparatus 300 a fat graft composition for reintroduction into a patient. For such a process, the barrier member 390 will be present within the apparatus 300 and positioned as shown in FIG. 28. The method may comprise collecting and washing adipose tissue in the internal containment volume 330 in a manner similar to that discussed above with respect to the preparation of the stromal vascular fraction. The washing may or may not include optional centrifuging. In a variation, the apparatus 300 may be specifically configured such that it cannot be centrifuged using the type of centrifuge that the apparatus 300 is typically inserted into. Such incompatibility may be achieved, for example, by adding ribs or extensions to the lid 308 and/or shell 306 such that the apparatus 300 cannot fit into the centrifuge. After washing the present method may include adding an additive to the washed tissue in the tissue retention volume 332. The additive may be added through the additional access port 372 or through the inlet port 304. The additive may comprise an active ingredient for delivery to the patient in a fat graft. The mixing device 316 may be rotated to assist in distributing the additive throughout the tissue within the tissue retention volume 332.

Once the fat graft composition is prepared, it may be removed from the tissue retention volume 332 by applying suction to the proximal end of the lumen 374. Such applied suction will pull the fat graft composition material through the lumen 374 and out of the tissue retention volume 332. During such suction, the barrier member 390, by being interposed between the distal end of the lumen 374 and the filter 312 will prevent the filter 312 from contacting the lumen 374 which could interfere with the contents of the tissue retention volume 332 being drawn into the lumen 374. Moreover, by having the barrier member 390 a fixed predetermined distance from the distal end 386 of the lumen 374, the material within the tissue retention volume 332 must flow through the restricted space between the barrier member 390 and the distal end 386 of the lumen 374. The restricted space and areal extent of the barrier member may serve to limit the flow rate of material moving from the tissue retention volume 332 into the lumen 374.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically compatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, the a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. An apparatus useful for collection of human biological material and for post-collection processing of collected material including enzymatic digestion and post-digestion centrifuging of the apparatus to prepare in the apparatus a concentrate product comprising stromal vascular fraction cells, the apparatus being orientable in a collection orientation for collection of human biological material comprising adipose during a lipoplasty procedure, as oriented in the collection orientation the apparatus comprising:

a filter;
a container having an internal containment volume, the internal containment volume comprising:
 a tissue retention volume and a filtrate volume separated by the filter;
 a collection volume within the filtrate volume and configured to collect the concentrate product during the centrifuging, the collection volume having a bottom elevation corresponding to a bottom elevation of the filtrate volume and a top elevation that is lower than the bottom elevation of the tissue retention volume; and
 a tapered portion that tapers in a downward direction with at least a portion of the tapered portion being located above the collection volume;
an inlet port in fluid communication with the tissue retention volume and configured for introducing human biological material directly into the tissue retention volume;
a suction port in fluid communication with the filtrate volume and providing access to the filtrate volume for suctioning from the filtrate volume components passing through the filter from the tissue retention volume to the filtrate volume; and
an extraction port in fluid communication with the internal containment volume and providing access to the collection volume;
wherein:
the extraction port is configured for access therethrough from above the container into the internal containment volume;
the apparatus is configured for advancing a hollow member through the extraction port to access the collection volume with an advancing tip of the hollow member; and
the extraction port is located above a portion of the filter, so that the advancing tip of the hollow member pierces through the filter when the tip of the hollow member is advanced from the extraction port into the collection volume.

2. An apparatus according to claim 1, wherein the collection volume includes a nadir and the extraction port is positioned above the nadir so that the advancing tip of the hollow member inserted through the extraction port is advanceable vertically downward to the vicinity of the nadir of the collection volume.

3. An apparatus according to claim 1, wherein the container comprises:
a fluid containment shell with an internal cavity portion forming at least a part of the internal containment volume, the internal cavity portion being open to above; and
a lid attached to the shell and disposed to cover from above the internal cavity portion;
wherein, the extraction port passes through the lid.

4. An apparatus according to claim 3, wherein all access into the internal containment volume is through one or more openings passing through the lid.

5. An apparatus according to claim 1, wherein the internal containment volume has an available processing volume in a range of from 75 cubic centimeters to 700 cubic centimeters.

6. An apparatus according to claim 5, wherein the collection volume is in a range of from 2 cubic centimeters to 20 cubic centimeters.

7. An apparatus according to claim 1, wherein the filter is a mesh filter having a separation size in a range of from 150 microns to 450 microns.

8. An apparatus according to claim 1, comprising a said concentrate product disposed within the collection volume of the internal containment volume.

9. An apparatus according to claim 8, wherein the said concentrate product disposed within the collection volume comprises stromal vascular fraction cells from enzymatically-digested adipose tissue.

10. An apparatus according to claim 8, having a said hollow member passing through the extraction port from outside of to inside of the internal containment volume, wherein in the internal containment volume the hollow member passes through the tissue retention volume, pierces the filter and has a tip disposed in the collection volume.

11. An apparatus according to claim 10, wherein the said hollow member is a hypodermic needle.

12. An apparatus according to claim 10, wherein the said hollow member is a cannula.

13. An apparatus according to claim 1, comprising a mixing device disposed at least in part within the tissue retention volume for mixing contents within the tissue retention volume, the mixing device comprising a rotatable shaft extending from outside of the internal containment volume to inside of the internal containment volume, wherein the shaft is rotatable about an axis that extends through the collection volume, the apparatus further comprising:
a lumen extending through the rotatable shaft and having a proximal end located outside of the internal containment volume and a distal end located within the tissue retention volume above the filter, wherein the lumen passes through the extraction port thereby providing access from outside of the internal containment volume to inside of the internal containment volume through the extraction port, so that the advancing tip of the hollow member pierces the filter when the advancing tip of the hollow member exits the distal end of the lumen and is advanced from the distal end of the lumen into the collection volume, and wherein the collection volume includes a nadir and an axis of the lumen is aligned so that the advancing tip of the hollow member exiting the distal end of the lumen is advanceable to the vicinity of the nadir of the collection volume.

14. An apparatus according to claim 13, wherein all access to the internal containment volume is through access ports wherein each said access port is configured for access through the said access port in a vertical direction from above the container.

15. A method for processing human biological material within the internal containment volume of an apparatus according to claim 1, the method comprising:
removing from the collection volume of the apparatus through a said hollow member material of a said concentrate product comprising stromal vascular fraction cells, the removing comprising inserting a said hollow member from outside of to inside of the tissue retention volume through the extraction port, advancing a said advancing tip of the said hollow member within the internal containment volume into the said concentrate product in the collection volume and during the advancing piercing through the filter with the said hollow member.

16. A method according to claim 15, comprising after the advancing, aspirating the material of the concentrate product through the said hollow member to outside of the container.

17. A method according to claim 16, wherein during the aspirating the material of the concentrate product is aspirated into a syringe located outside of the internal containment volume.

18. A method according to claim 16, comprising prior to the aspirating, injecting suspension liquid from the said hollow member into the collection volume to disperse the material of the concentrate product in the suspension liquid in the collection volume.

19. A method according to claim 18, comprising after the injecting, removing from the container at least most of the suspension liquid with the material of the concentrate product.

20. A method according to claim 15, wherein the said concentrate product comprises stromal vascular fraction cells from enzymatically-digested adipose.

21. A method according to claim 15, comprising prior to the removing:
preparing the said concentrate product in the collection volume, the preparing comprising centrifuging the apparatus to form a pellet phase including the stromal vascular fraction cells in the collection volume.

22. A method according to claim 21, comprising prior to the centrifuging:
digesting material within the containment volume, the digesting material comprising adding enzyme to the containment volume to contact at least a portion of washed human biological material within the tissue retention volume, the enzyme being of a type capable of breaking down a portion of the washed human biological material to release the stromal vascular fraction cells in a form capable of passing through the filter.

23. A method according to claim 22, comprising prior to the digesting:
washing human biological material comprising adipose with a wash liquid, the washing comprising adding the wash liquid to the internal containment volume to contact the human biological material within the tissue retention volume and passing through the filter and removing from the filtrate volume at least a portion of the wash liquid along with one or more components washed from the human biological material while retaining the washed human biological material in the tissue retention volume.

24. A method according to claim 21, wherein after the centrifuging and prior to the removing, the stromal vascular fraction cells are contained in a bottom separated layer or layers disposed within the collection volume, and the removing comprises removing from the filtrate volume other separated layers within the filtrate volume disposed above the bottom separated layer or layers after the centrifuging.

25. A method according to claim 24, comprising after the removing from the filtrate volume separated layers within the filtrate volume disposed above the bottom separated layer or layers:
diluting the bottom layer or layers with a diluent fluid to prepare a diluted concentrate product, and removing the diluted concentrate product from the filtrate volume.

26. A method according to claim 24, wherein the other separated layers comprise an aqueous layer, a disaggregated adipose layer and an oil layer.

27. A method according to claim 16, wherein during the aspirating the said hollow member passes through a top of the container through the extraction port.

28. A method according to claim 15, wherein the said hollow member is a hypodermic needle.

29. A method according to claim 15, wherein the said hollow member is a cannula.

30. A method for processing tissue from a lipoplasty procedure within a containment volume of a portable tissue collection and processing apparatus to prepare within the apparatus a concentrated product comprising stromal vascular fraction cells from the tissue, the apparatus having an access orientation and in the access orientation the apparatus comprising:

- a filter and a container having the internal containment volume, wherein the internal containment volume comprises a tissue retention volume and a filtrate volume separated by the filter and the filtrate volume includes a collection volume having a bottom elevation corresponding to a bottom elevation of the filtrate volume and a top elevation that is lower than the bottom elevation of the tissue retention volume;
- an inlet port in fluid communication with the tissue retention volume and configured for introducing human biological material directly into the tissue retention volume;
- a suction port in fluid communication with the filtrate volume and providing access to the filtrate volume for suctioning from the filtrate volume components passing through the filter from the tissue retention volume to the filtrate volume; and
- an extraction port in fluid communication with the internal containment volume and providing access to the collection volume;

the method comprising:

washing the tissue with a wash liquid, the washing comprising adding the wash liquid to the internal containment volume to contact the tissue within the tissue retention volume and passing through the filter and removing from the filtrate volume at least a portion of the wash liquid along with one or more component washed from the tissue while retaining washed tissue in the tissue retention volume;

digesting tissue within the containment volume, the digesting tissue comprising:

adding enzyme to the containment volume to contact at least a portion of the washed tissue within the tissue retention volume, the enzyme being of a type capable of breaking down a portion of the washed tissue to release a target component in a form capable of passing through the filter; and after adding the enzyme, agitating contents of the containment volume for a time and at a temperature sufficient to release the target component in a the form capable of passing through the filter;

centrifuging the apparatus to prepare in the filtrate volume a concentrate product comprising the target component;

selectively removing the concentrate product from the filtrate volume, the selectively removing comprising inserting a hollow member from outside of to inside of the tissue retention volume through the extraction port, advancing a tip of the hollow member within the internal containment volume to pierce through the filter and into the collection volume after piercing through the filter.

* * * * *